US012758638B2

(12) United States Patent
Kim et al.

(10) Patent No.: US 12,758,638 B2
(45) **Date of Patent: *Oct. 13, 2026**

(54) NANOSATELLITE-SUBSTRATE COMPLEX AND METHOD OF REGULATING MACROPHAGE ADHESION AND POLARIZATION USING THE SAME

(71) Applicant: Korea University Research and Business Foundation, Seoul (KR)

(72) Inventors: Young-Keun Kim, Seoul (KR); Heemin Kang, Seoul (KR); Thomas Myeongseok Koo, Seoul (KR); Myeong-Soo Kim, Suwon-si (KR); Yuri Kim, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 1112 days.

This patent is subject to a terminal disclaimer.

(21) Appl. No.: 17/834,314

(22) Filed: Jun. 7, 2022

(65) Prior Publication Data

US 2023/0210996 A1 Jul. 6, 2023

(30) Foreign Application Priority Data

Dec. 31, 2021 (KR) ........................ 10-2021-0194432

(51) Int. Cl.

| | |
|---|---|
| ***A61K 47/52*** | (2017.01) |
| ***A61K 47/69*** | (2017.01) |
| *B82Y 5/00* | (2011.01) |
| *B82Y 30/00* | (2011.01) |
| *B82Y 40/00* | (2011.01) |

(52) U.S. Cl.

CPC .......... *A61K 47/52* (2017.08); *A61K 47/6929* (2017.08); *B82Y 5/00* (2013.01); *B82Y 30/00* (2013.01); *B82Y 40/00* (2013.01)

(58) Field of Classification Search

None

See application file for complete search history.

(56) References Cited

FOREIGN PATENT DOCUMENTS

| | | | |
|---|---|---|---|
| KR | 10-1918817 | B1 | 11/2018 |
| KR | 10-2020-0050357 | A | 9/2021 |
| KR | 10-2021-0110128 | A | 9/2021 |

OTHER PUBLICATIONS

Wong et al (Magnetically Tuning Tether Mobility of Integrin Ligand Regulates Adhesion, Spreading, and Differentiation of Stem Cells. Nano Lett. 2017, 17, 1685-1695) (Year: 2017).*

Salguerino et al (Bifunctional Gold-Coated Magnetic Silica Spheres. Chem. Mater. 2006, 18, 2701-2706) (Year: 2006).*

Patel et al (Synthesis and Cell Adhesive Properties of Linear and Cyclic RGD Functionalized Polynorbornene Thin Films. Biomacromolecules. Aug. 13, 2012; 13(8): 2546-2553). (Year: 2012).*

Wong, Dexter S.H., et al. "Magnetically Tuning Tether Mobility of Integrin Ligand Regulates Adhesion, Spreading, and Differentiation of Stem Cells." Nano letters 17.3 (2017): 1685-1695.

Heuer-Jungemann, Amelie, et al. "The Role of Ligands in the Chemical Synthesis and Applications of Inorganic Nanoparticles." Chemical reviews 119.8 (2019): 4819-4880.

Korean Office Action issued on Sep. 6, 2023, in counterpart Korean Patent Application No. 10-2021-0194432 (8 pages in English and 11 pages in Korean).

Thangam, Ramar, et al. "Remote Switching of Elastic Movement of Decorated Ligand Nanostructures Controls the Adhesion-Regulated Polarization of Host acrophages." *Advanced Functional Materials* vol. 31. Issue 21 (May 21, 2021): 2008698.

Kang, Heemin, et al. "Magnetic manipulation of reversible nanocaging controls in vivo adhesion and polarization of macrophages." *ACS nano* vol. 12. Issue 6 (May 16, 2018): pp. 5978-5994.

Kang, Heemin, et al. "Near-infrared light-controlled regulation of intracellular calcium to modulate macrophage polarization." *Biomaterials* vol. 178 (Sep. 2018): pp. 681-696.

* cited by examiner

*Primary Examiner* — Jake M Vu

(74) *Attorney, Agent, or Firm* — NSIP Law

(57) ABSTRACT

According to the present invention, it is possible to provide a nanosatellite-substrate complex capable of regulating macrophage adhesion and polarization. In addition, according to the present invention, it is possible to provide a method for preparing a nanosatellite-substrate complex capable of regulating macrophage adhesion and polarization. In addition, according to the present invention, it is possible to provide a method of regulating macrophage adhesion and polarization using the nanosatellite-substrate complex.

19 Claims, 57 Drawing Sheets
(38 of 57 Drawing Sheet(s) Filed in Color)

NANOSATELLITE-SUBSTRATE COMPLEX AND METHOD OF REGULATING MACROPHAGE ADHESION AND POLARIZATION USING THE SAME

CROSS-REFERENCE TO RELATED APPLICATIONS

This application claims priority to and the benefit of Korean Patent Application No. 10-2021-0194432 filed in the Korean Intellectual Property Office on Dec. 31, 2021, the entire contents of which are incorporated herein by reference.

BACKGROUND OF THE INVENTION

Field of the Invention

The present invention relates to a nanosatellite-substrate complex, a method for preparing the same, and a method of regulating macrophage adhesion and polarization using the same, and more particularly, to a nanosatellite-substrate complex capable of regulating macrophage adhesion and polarization, and a method of regulating macrophage adhesion and polarization using the same.

Description of the Prior Art

Physical screens, which occur in the extracellular matrix (ECM), separate various tissue compartments to help modulate homeostasis and tissue regeneration by controlling biomolecular transport and cellular infiltration. Certain tissues can act as physical screens to modulate tissue repair mechanisms that involve the interactions of diverse cells. However, ECM-mimicking artificial materials that can dispersively and dynamically control bioactive surfaces are rare.

Integrin dynamically forms links with the bioactive-ligand-displaying-ECM, of which the RGD ligands mediate focal adhesion and intracellular mechanotransduction of cells. Remote manipulation of unscreening the ligands by light or magnetic fields can dynamically modulate cell adhesion. Conventionally, light such as ultraviolet (UV), visible, and near infrared (NIR) light has been used for photochemical manipulation of screening and unscreening of the ligands. For example, UV light has been applied to chemically cleave photosensitive polyethylene glycol-based brushes to unscreen ligand-grafted gold nanoparticles for facilitating cell adhesion. Using photoisomers such as azobenzene derivatives, screening and unscreening of the ligands via self-assembled brushes can be manipulated by illuminating UV light and visible light or single wavelengths having the ability to stimulate intracellular mechanotransduction. However, manipulation of screening and unscreening of the ligands by light in vivo has rarely been reported.

In addition, magnetic field can easily penetrate tissues in vivo to enable noninvasive control of physical screens. For example, cell adhesion can be remotely controlled by controlling screening and unscreening of the ligands through modulation of nanoparticles having magnetic properties.

SUMMARY OF THE INVENTION

An object of the present invention is to provide a nanosatellite-substrate complex which has magnetic properties and is capable of regulating macrophage adhesion and polarization.

Another object of the present invention is to provide a method for preparing the nanosatellite-substrate complex.

Still another object of the present invention is to provide a method of regulating macrophage adhesion and polarization using the nanosatellite-substrate complex.

According to one aspect of the present invention, embodiments of the present invention may include a nanosatellite-substrate complex for regulating macrophage adhesion and polarization comprising: a substrate; a core-shell-type magnetic nanoparticle provided to be spaced apart from at least one side of the substrate; a gold nanoparticle connected to one side of the magnetic nanoparticle; a first linker connecting between the substrate and the gold nanoparticle; a second linker connecting between the gold nanoparticle and a ligand; and the ligand connected to the gold nanoparticle via the second linker, wherein the gold nanoparticle is connected to the ligand via the second linker to form a nanoassembly, the magnetic nanoparticle is conjugated to the nanoassembly to form a nanosatellite structure, the nanoassembly comprises one or more gold nanoparticles, one or more second linkers connected to at least one of the one or more gold nanoparticles, and the ligand connected to the second linker, and one or more nanoassemblies are comprised in the nanosatellite structure.

The magnetic nanoparticle may be composed of: a core composed of iron oxide; and a shell provided to cover the outer surface of the core and comprising silica.

The diameter of the gold nanoparticles may include at least one of a first average diameter, a second average diameter, and a third average diameter, wherein the first average diameter may be 3.5 nm to 10.5 nm, the second average diameter may be 12 nm to 14 nm, and the third average diameter may be 15 nm to 25 nm.

A plurality of the nanoassemblies may be provided adjacent to each other, and the distance between the gold nanoparticles in the nanoassemblies provided adjacent to each other may include at least one of a first distance, a second distance and a third distance, wherein the first distance may be 2 nm to 4 nm, the second distance may be 15 nm to 20 nm, and the third distance may be 18 nm to 22 nm.

The nanoassembly may be provided to completely cover the outer surface of the magnetic nanoparticle.

The magnetic nanoparticle may have an average diameter of 150 nm to 250 nm, and the magnetic nanoparticle may have at least one of an amino group (—$HN_2$) and a thiol group (—SH) on a surface thereof.

The first linker and the second linker may have a structure of the following Formula 1:

[Formula 1]

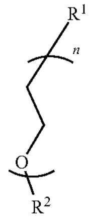

wherein $R^1$ is one of a thiol group (—SH) and an amino group (—$NH_2$), $R^2$ is one of a carboxyl group (—COOH), an amino group (—$NH_2$) and a succinimidyl ester group, and n is a number ranging from 113 to 450.

The ligand may be a cyclic RGD ligand.

A surface of the nanosatellite structure, which faces the substrate, may be spaced apart from the substrate with the first linker interposed therebetween, and the first linker may be elastic and the length thereof may be reversibly changed by application of a magnetic field.

The nanosatellite structure may be provided to be spaced apart from one side of the substrate, and the first linker may be compressed by applying a magnetic field to the other side of the substrate, and the nanosatellite structure may move in a direction toward the substrate to promote macrophage adhesion and M2 polarization.

The nanosatellite structure may be provided to be spaced apart from one side of the substrate, and the first linker may be stretched by applying a magnetic field to the upper side of the nanosatellite structure, which is one side of the substrate, and the nanosatellite structure may move in a direction away from the substrate to inhibit macrophage adhesion and promote macrophage M1 polarization.

The density of the nanosatellite structure provided on the substrate may be 1.0 nanosatellite structure/$\mu m^2$ to 6 nanosatellite structures/$\mu m^2$.

One embodiment of the present invention may include a method for preparing a nanosatellite-substrate complex for regulating macrophage adhesion and polarization, the method comprising: coating the surface of iron oxide with a silica having at least one of an amino group and a thiol group to form magnetic nanoparticles; providing gold nanoparticles on the surfaces of the magnetic nanoparticles; adding and dispersing the magnetic nanoparticles having the gold nanoparticles provided thereon in a solution containing a polymer linker to form a first linker and a second linker; reacting the first linker with a substrate having amine groups formed thereon, so that the first linker is bound to at least a portion of the amine groups formed on the substrate and the magnetic nanoparticles having the gold nanoparticles provided thereon are conjugated to the substrate; deactivating amine groups, which remain unbound to the first linker on the substrate, by treatment with a deactivating group; and conjugating a ligand to the second linker.

The diameter of the gold nanoparticles may be any one of a first average diameter, a second average diameter and a third average diameter. The first average diameter of the gold nanoparticles may be 3.5 nm to 10.5 nm, and the gold nanoparticles having the first average diameter may be formed by reacting first gold seed particles with a functional group on the surfaces of the magnetic nanoparticles to provide the gold seed particles on the magnetic nanoparticles, and adding and stirring the magnetic nanoparticles having the gold seed particles provided thereon in a gold-containing solution to grow the gold seed particles.

Alternatively, the second average diameter of the gold nanoparticles may be 12 nm to 14 nm, the third average diameter thereof may be 15 nm to 25 nm, and the gold nanoparticles having the second or third average diameter may be provided on the magnetic nanoparticles by adding and stirring second gold seed particles in a gold-containing solution to grow the second gold seed particles, thereby forming gold nanoparticles, and reacting the gold nanoparticles, formed by growing the second gold seed particles, with a functional group on the surfaces of the magnetic nanoparticles.

The gold-containing solution may include a first solution containing sodium citrate and a second solution containing chloroauric acid, wherein the first solution and the second solution may be sequentially added, and the average diameter of the gold nanoparticles may be controlled by controlling the number of times the first solution and the second solution are added.

One embodiment of the present invention may include a method of regulating macrophage adhesion and polarization using the nanosatellite-substrate complex, the method comprising regulating macrophage adhesion and polarization by applying a magnetic field to the nanosatellite-substrate complex having the above-described characteristics.

The magnetic field may be applied from outside the body to remotely control the nanosatellite-substrate complex in the body.

The magnetic field may have a strength of 100 mT to 500 mT.

The nanosatellite structure may be provided to be spaced apart from one side of the substrate, and a plurality of the nanoassemblies may be provided adjacent to each other in the nanosatellite structure. The gold nanoparticles may have an average diameter of 3.5 nm to 10.5 nm, and the distance between the gold nanoparticles in the nanoassemblies provided adjacent to each other may be 2 nm to 4 nm. The first linker may be stretched by applying the magnetic field to the upper side of the nanosatellite structure, which is one side of the substrate, and the nanosatellite structure may move in a direction away from the substrate to inhibit macrophage adhesion and promote macrophage M1 polarization.

The nanosatellite structure may be provided to be spaced apart from one side of the substrate, and a plurality of the nanoassemblies may be provided adjacent to each other in the nanosatellite structure. The gold nanoparticles may have an average diameter of 12 nm to 14 nm, and the distance between the gold nanoparticles in the nanoassemblies provided adjacent to each other may be 15 nm to 20 nm. The first linker may be compressed by applying the magnetic field to the other side of the substrate, and the nanosatellite structure may move in a direction toward the substrate to promote macrophage adhesion and M2 polarization.

BRIEF DESCRIPTION OF THE DRAWINGS

The patent or application file contains a least one drawing executed in color. Copies of this patent or patent application publication with color drawing(s) will be provided by the Office upon request and payment of the necessary fee.

DETAILED DESCRIPTION OF THE INVENTION

The details of other embodiments are included in the detailed description and the accompanying drawings.

The advantages and features of the present invention, and the way of attaining them, will become apparent with reference to the embodiments described below in conjunction with the accompanying drawings. However, the present disclosure is not limited to the embodiments disclosed below and may be embodied in a variety of different forms. Since all numbers, values and/or expressions referring to quantities of components, reaction conditions, etc., used in the present specification, are subject to the various uncertainties of measurement encountered in obtaining such values, unless otherwise indicated, all are to be understood as modified in all instances by the term “about.” Where a numerical range is disclosed herein, such a range is continuous, inclusive of both the minimum and maximum values of the range as well as every value between such minimum and maximum values, unless otherwise indicated. Still further, where such a range refers to integers, every integer between the minimum and maximum values of such a range is included, unless otherwise indicated.

In the present specification, where a range is stated for a parameter, it will be understood that the parameter includes all values within the stated range, inclusive of the stated endpoints of the range. For example, a range of 5 to 10 will be understood to include the values 5, 6, 7, 8, 9, and 10, as well as any sub-range such as 6 to 10, 7 to 10, 6 to 9, and 7 to 9, and also include any value and range between the integers which are reasonable in the context of the range stated, such as 5.5, 6.5, 7.5, 5.5 to 8.5 and 6.5 to 9. For example, a range of “10% to 30%” will be understood to include the values 10%, 11%, 12%, 13%, etc., and all integers up to and including 30%, as well as any sub-range such as 10% to 15%, 12% to 18%, 20% to 30%, etc., and also include any value between the integers which are reasonable in the context of the range stated, such as 10.5%, 15.5%, 25.5%, etc.

In the present specification, the term “nanoassembly” may refer to a structure in which a gold nanoparticle and a ligand are connected to each other via a second linker. The term “nanosatellite structure” may refer to a structure in which the nanoassembly is conjugated to a magnetic nanoparticle.

The term "nanosatellite-substrate complex" refers to a structure in which the nanosatellite structure is conjugated to a substrate via a first linker.

Figure 1:
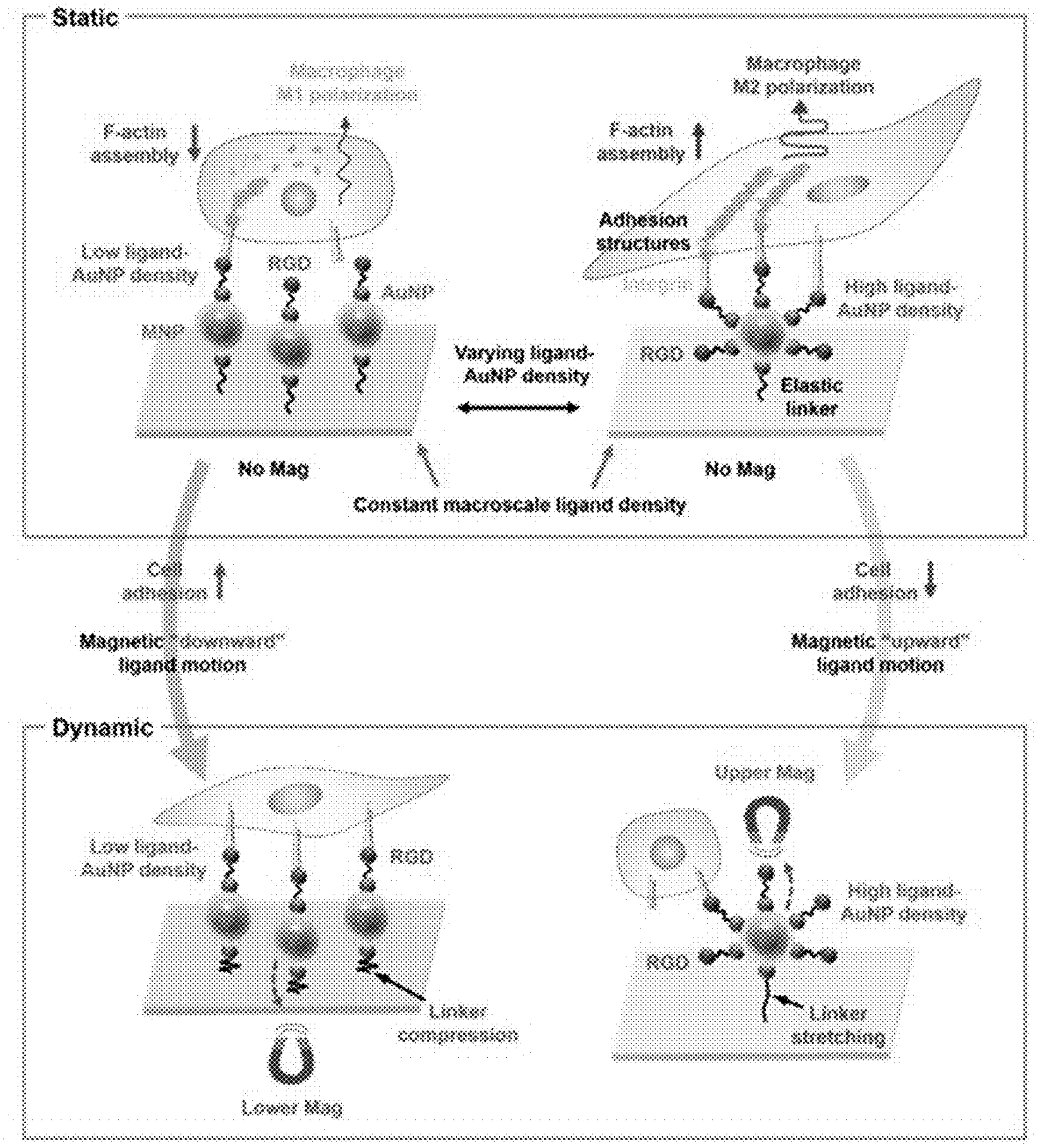
FIGS. 1 and 2 schematically show a process of regulating macrophage adhesion and polarization by applying a magnetic field to a nanosatellite-substrate complex according to one embodiment of the present invention.
Figure 2:
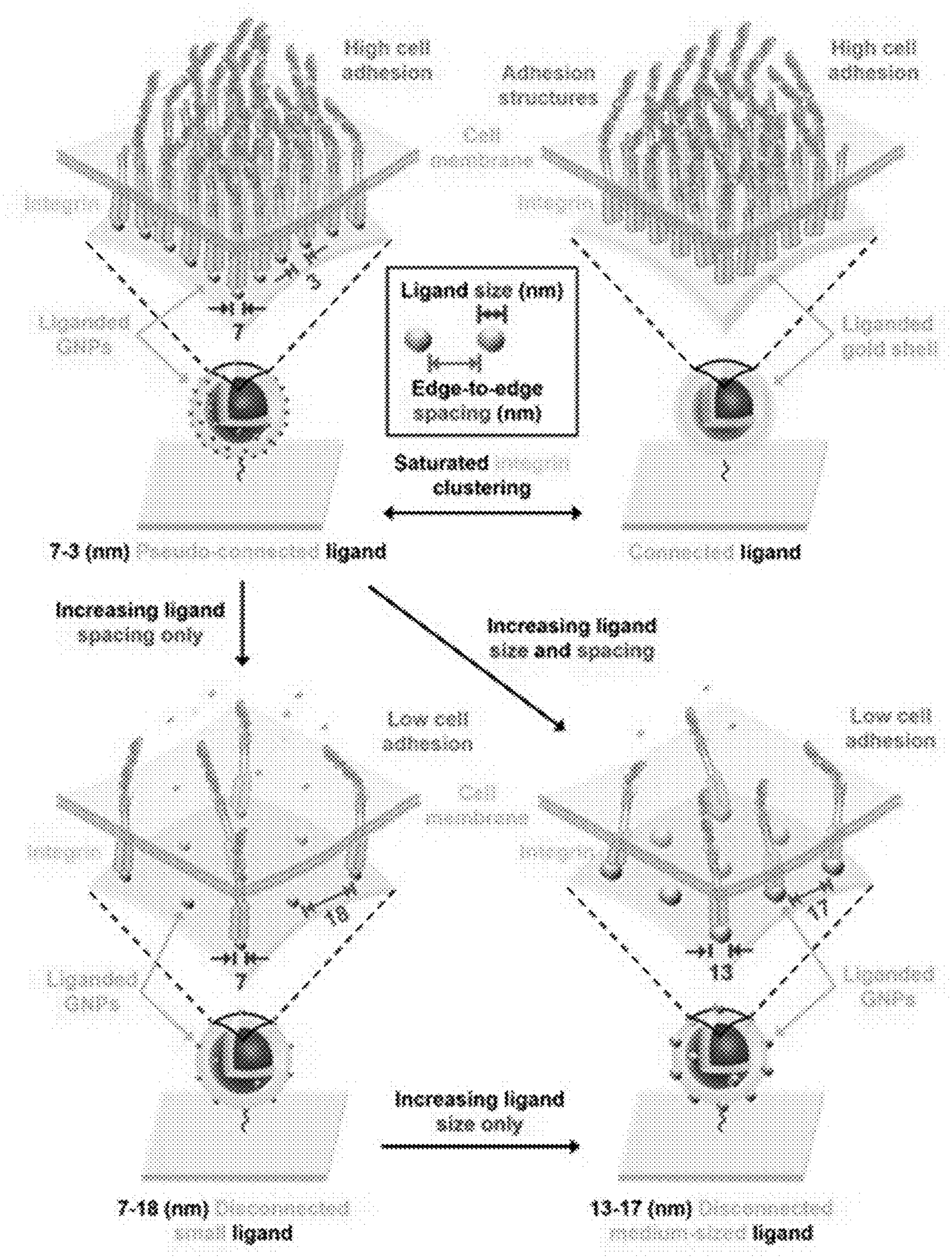

FIGS. 1 and 2 schematically show a process of regulating macrophage adhesion and polarization by applying a magnetic field to a nanosatellite-substrate complex according to one embodiment of the present invention.

In accordance with one aspect of the present invention, embodiments of the present invention may include a nanosatellite-substrate complex for regulating macrophage adhesion and polarization comprising: a substrate; a core-shell-type magnetic nanoparticle provided to be spaced apart from at least one side of the substrate; a gold nanoparticle connected to one side of the magnetic nanoparticle; a first linker connecting between the substrate and the gold nanoparticle; a second linker connecting between the gold nanoparticle and a ligand; and the ligand connected to the gold nanoparticle via the second linker, wherein the gold nanoparticle is connected to the ligand via the second linker to form a nanoassembly, the magnetic nanoparticle is conjugated to the nanoassembly to form a nanosatellite structure, the nanoassembly comprises one or more gold nanoparticles, one or more second linkers connected to at least one of the one or more gold nanoparticles, and the ligand connected to the second linker, and one or more nanoassemblies are comprised in the nanosatellite structure.

The substrate may have an amino group (—$NH_2$) on the surface thereof, and the first linker connected to one side of the magnetic nanoparticle may be conjugated thereto.

Since the magnetic nanoparticle has magnetic properties, movement of the magnetic nanoparticle may be induced when a magnetic field is applied to the magnetic nanoparticle. Thus, it is possible to regulate macrophage adhesion and polarization by moving the nanosatellite structure comprising the magnetic nanoparticle.

The magnetic nanoparticle may have a core-shell structure, and the core may be composed of a magnetic material, preferably iron oxide. The shell may be provided to cover the outer surface of the core and may be composed of a shell comprising silica. The surface of the shell has a functional group capable of binding to the gold nanoparticles, and thus the gold nanoparticles may be conjugated to the magnetic nanoparticle. The functional group capable of binding to the gold nanoparticles may be, for example, at least one of an amino group (—$NH_2$) and a thiol group (—SH).

The magnetic nanoparticle may have a diameter sufficient to allow the gold nanoparticles to be conjugated thereto. The average diameter of the magnetic nanoparticle may be 150 nm to 250 nm.

Gold nanoparticles may be provided on one side of the magnetic nanoparticle.

When the functional group on the surface of the magnetic nanoparticle is an amino group, the gold nanoparticles may be provided by Au-amino bonding with the amino group on the surface of the magnetic nanoparticle. The gold nanoparticles provided on the surface of the magnetic nanoparticle may be one or more in number.

The diameter of the gold nanoparticles may include at least one of a first average diameter, a second average diameter, and a third average diameter, wherein the first average diameter may be 3.5 nm to 10.5 nm, the second average diameter may be 12 nm to 14 nm, and the third average diameter may be 15 nm to 25 nm.

The diameter of the gold nanoparticles may be a diameter sufficient to allow a ligand to be conjugated thereto. The diameter of the gold nanoparticles may be a diameter sufficient to allow a ligand to be conjugated thereto.

When the diameter of the gold nanoparticles is the first average diameter, the gold nanoparticles may be formed by conjugating gold seed particles smaller than the first average diameter to the magnetic nanoparticle and then growing the gold seed particles on the magnetic nanoparticle. In addition, when the diameter of the gold nanoparticles is any one of the second average diameter and the third average diameter, gold nanoparticles having the second average diameter or the third average diameter may be formed and then conjugated to the magnetic nanoparticle.

A polymer linker may be conjugated to the gold nanoparticles connected to one side of the magnetic nanoparticle. The polymer linker may have a structure of Formula 1 below. The first binding site of the polymer linker may include at least any one of an amino group (—$NH_2$) and a thiol group (—SH), and may be represented by $R^1$ in Formula 1. The second binding site of the polymer linker may have at least any one of a carboxyl group (—COOH), an amino group (—$NH_2$) and a succinimidyl ester group, and may be represented by $R^2$ in Formula 1.

In addition, n in Formula 1 may be a number ranging from 113 to 450, preferably from 113 to 225.

[Formula 1]

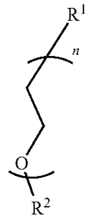

The polymeric linker may include a first linker and a second linker.

The first binding site of the first linker may bind to the gold nanoparticle, and the second binding site thereof may bind to the substrate and connect between the gold nanoparticle and the substrate. The second binding site may be connected by chemical bonding with an amino group on the substrate.

The first binding site of the second linker may bind to the gold nanoparticle, and the second binding site thereof may bind to the ligand and connect between the gold nanoparticle and the ligand.

One or more first linkers and one or more second linkers may be conjugated to each of the gold nanoparticles.

The ligand may be a site which is connected to the gold nanoparticle via the second linker and to which macrophage integrin binds.

The ligand may be a cyclic RGD ligand. The RGD may be a ligand having a tripeptide structure consisting of arginine-glycine-aspartame (Arg-Gly-Asp).

The ligand may be a ligand having an amino group (—$NH_2$).

The ligand may be a ligand having a lysine residue bound thereto.

One or more ligands may be conjugated to each of the gold nanoparticles.

The gold nanoparticle and the ligand may be connected to each other via the second linker to form a nanoassembly. One or more nanoassemblies may be connected to one side of the magnetic nanoparticle.

When a plurality of the nanoassemblies are comprised in the nanosatellite structure, the nanoassemblies may be provided adjacent to each other. The distance between the nanoassemblies provided adjacent to each other may be determined by the distance between the gold nanoparticles included in the nanoassemblies.

The distance between the gold nanoparticles in the adjacent nanoassemblies may include at least one of a first distance, a second distance, and a third distance. Here, the first distance may be 2 nm to 4 nm, the second distance may be 15 nm to 20 nm, and the third distance may be 18 nm to 22 nm.

In addition, the nanoassemblies may be provided to completely cover the outer surface of the magnetic nanoparticle.

The nanoassembly may be conjugated to the magnetic nanoparticle to form a nanosatellite structure.

As the distance between the adjacent gold nanoparticles decreases, the distance between the ligands connected to the gold nanoparticles may decrease, and as the distance between the ligands decreases, macrophages can recognize the gold nanoparticle-conjugated ligands as connected ligands. Thus, as the distance between the adjacent gold nanoparticles decreases, the density of macrophage integrin that binds to the ligands may increase, whereby integrin clustering may occur and macrophage M2 polarization may be promoted.

For example, when the adjacent gold nanoparticles have the first distance, macrophages can recognize the ligands in the same way as when the nanoassemblies are provided to completely cover the outer surface of the magnetic nanoparticle, and macrophage M2 polarization may be promoted.

When the adjacent gold nanoparticles have the first distance, the gold nanoparticles may be formed by a method of growing the gold seed particles on the surface of the magnetic nanoparticle to form gold nanoparticles. In this case, the distance between the adjacent gold seed particles may be similar to or larger than the Debye length, but the distance between the adjacent gold nanoparticles formed by growth of the gold seed particles may be similar to or smaller than the Debye length. Accordingly, when the distance between the adjacent gold nanoparticles has the first distance, the ligand conjugated to each of the gold nanoparticles may bind to a cell to form a quasi-connection, and macrophages may recognize the ligands in the same way as when the nanoassemblies are provided to completely cover the outer surface of the magnetic nanoparticle. Thus, macrophage adhesion and M2 polarization may be promoted.

On the other hand, as the distance between the adjacent gold nanoparticles increases, the distance between the ligands connected to the gold nanoparticles may increase, so that the density of macrophage integrin that binds to the ligands may decrease and macrophage differentiation may be inhibited. For example, when the adjacent gold nanoparticles have the third distance, macrophage adhesion may be inhibited and macrophage M1 polarization may be promoted.

However, when the size of the gold nanoparticles is very large, even if the distance between the gold nanoparticles is long, a plurality of integrin molecules may bind to one gold nanoparticle, so that integrin clustering may occur and macrophage adhesion may slightly increase.

The density of the nanosatellite structures provided on the substrate may be kept constant, and the density may be 1.0 nanosatellite structure/$\mu m^2$ to 6.0 nanosatellite structures/$\mu m^2$.

A surface of the nanosatellite structure, which faces the substrate, may be spaced apart from the substrate with the first linker therebetween, and the first linker may be elastic and the length thereof may be reversibly changed by application of a magnetic field.

When the nanosatellite structure is moved by applying a magnetic field to the nanosatellite-substrate complex, macrophage adhesion and polarization may be regulated.

For example, when the first linker is compressed by applying a magnetic field and the nanosatellite structure moves in a direction toward the substrate, the nanosatellite structure may be fastened closely to the substrate, and macrophage adhesion and M2 polarization may be promoted. In addition, for example, when the first linker is stretched by applying a magnetic field and the nanosatellite structure moves in a direction away from the substrate, the nanosatellite structure may move away from the substrate, macrophage adhesion may be inhibited, and M1 polarization may be promoted.

Specifically, the nanosatellite structure may be provided to be spaced apart from one side of the substrate, the first linker may be compressed by applying a magnetic field to the other side of the substrate, and the nanosatellite structure may move in a direction toward the substrate. In this case, the nanosatellite structure may be fastened closely to the substrate, and macrophage adhesion and M2 polarization may be promoted.

In addition, specifically, the nanosatellite structure may be provided to be spaced apart from one side of the substrate, the first linker may be stretched by applying a magnetic field to the upper side of the nanosatellite structure, which is one side of the substrate, and the nanosatellite structure may move in a direction away from the substrate. In this case, the nanosatellite structure may move away from the substrate, macrophage adhesion may be inhibited, and macrophage M1 polarization may be promoted.

The magnetic field may be applied from outside the body to remotely control the nanosatellite-substrate complex in the body.

The magnetic field may be applied at a strength of 100 mT to 500 mT.

According to another aspect of the present invention, one embodiment of the present invention may include a method for preparing a nanosatellite-substrate complex for regulating macrophage adhesion and polarization, the method comprising: coating the surface of iron oxide with a silica having at least one of an amino group and a thiol group to form magnetic nanoparticles; providing gold nanoparticles on the surfaces of the magnetic nanoparticles; adding and dispersing the magnetic nanoparticles having the gold nanoparticles provided thereon in a solution containing a polymer linker to form a first linker and a second linker; reacting the first linker with a substrate having amine groups formed thereon, so that the first linker is bound to at least a portion of the amine groups formed on the substrate and the magnetic nanoparticles having the gold nanoparticles provided thereon are conjugated to the substrate; deactivating amine groups, which remain unbound to the first linker on the substrate, by treatment with a deactivating group; and conjugating a ligand to the second linker.

For preparation of the magnetic nanoparticles, iron chloride hydrate, sodium acetate and DI water may be mixed and stirred with ethylene glycol and washed to form a core composed of iron oxide, and the core may be coated with a shell comprising silica by adding 3-aminopropyl triethoxysilane (APTES) thereto. The surface of the magnetic nanoparticle may comprise at least one of an amino group ($—NH_2$) and a thiol group (—SH).

The surface of the magnetic nanoparticle may have gold nanoparticles provided thereon.

The gold nanoparticles may have any one of a first average diameter, a second average diameter, and a third average diameter. The first average diameter of the gold nanoparticles may be 3.5 nm to 10.5 nm, the second average diameter may be 12 nm to 14 nm, and the third average diameter may be 15 nm to 25 nm.

When the gold nanoparticles have the first average diameter, first gold seed particles may be provided on the surfaces of the magnetic nanoparticles and then grown into first gold nanoparticles on the surfaces of the magnetic nanoparticles. The first gold seed particles may be provided on the surfaces of the magnetic nanoparticles by reaction with a functional group on the surfaces of the magnetic nanoparticles, and the magnetic nanoparticles having the first gold seed particles provided thereon may be added to and stirred in a gold-containing solution to grow the first gold seed particles into gold nanoparticles.

In order to form gold nanoparticles having a spacing smaller than the Debye length, the first gold seed particles may be conjugated to the surfaces of the magnetic nanoparticles so that the distance between the first gold seed particles may be larger than the Debye length, and the conjugated first gold seed particles may be grown into gold nanoparticles having a spacing smaller than the Debye length.

The first gold seed particles may be 2.0 nm to 5.0 nm in average diameter.

In addition, when the gold nanoparticles have any one of the second average diameter and the third average diameter, second gold seed particles may be grown and then conjugated to the magnetic nanoparticles. The second gold seed particles may be added to a gold-containing solution and grown into second gold nanoparticles by heating and stirring. Then, the second gold nanoparticles may be provided on the surfaces of the magnetic nanoparticles by reaction with any one of an amino group and a thiol group on the surfaces of the magnetic nanoparticles.

The second gold seed particles may have an average diameter of 3.0 nm to 15 nm.

The gold-containing solution may comprise a first solution containing sodium citrate ($Na_3Cit$) and a second solution containing chloroauric acid ($HAuCl_4$). The first solution and the second solution may be sequentially added, and the size of the gold nanoparticles may be controlled by controlling the number of times the first solution and the second solution are added. Specifically, as the number of times the first solution and the second solution are added increases, the size of the gold nanoparticles formed may increase.

The concentration of the first solution may be 40 mM to 80 mM, and the concentration of the second solution may be 5 mM to 30 mM.

The deactivating group for deactivating the substrate may have a structure of Formula 2. n in Formula 2 may be a number ranging from 113 to 450, preferably from 113 to 225.

[Formula 2]

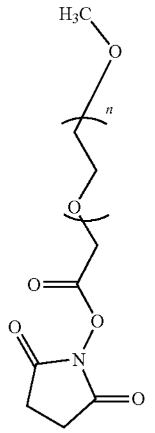

In addition, the present invention may include a method of regulating macrophage adhesion and polarization using the nanosatellite-substrate complex, the method comprising regulating macrophage adhesion and polarization by applying a magnetic field to the nanosatellite-substrate complex having the above-described characteristics.

The magnetic field may be applied from outside the body to remotely control the nanosatellite-substrate complex in the body.

The magnetic field may be applied at a strength of 100 mT to 500 mT.

The nanosatellite structure may be provided to be spaced apart from one side of the substrate, and a plurality of the nanoassemblies may be provided adjacent to each other on the surface of the magnetic nanoparticle. For example, when the gold nanoparticles have an average diameter of 3.5 nm to 10.5 nm (first average diameter) and the distance between the gold nanoparticles in the nanoassemblies provided adjacent to each other is 2 nm to 4 nm (first distance), the first linker may be stretched by applying the magnetic field to the upper side of the nanosatellite structure, which is one side of the substrate, and the nanosatellite structure may move in a direction away from the substrate to inhibit macrophage adhesion and promote macrophage M1 polarization. When the average diameter of the gold nanoparticles is the first average diameter and the distance between the adjacent gold nanoparticles is the first distance, macrophage adhesion and M2 polarization may be promoted before application of the magnetic field, but macrophage adhesion may be inhibited and macrophage M1 polarization may be promoted after application of the magnetic field.

The nanosatellite structure may be provided to be spaced apart from one side of the substrate, and a plurality of the nanoassemblies may be provided adjacent to each other on the surface of the magnetic nanoparticle. For example, when the average diameter of the gold nanoparticles is 12 nm to 14 nm (second average diameter) and the distance between the gold nanoparticles in the nanoassemblies provided adjacent to each other is 15 nm to 20 nm (second distance), the first linker may be compressed by applying the magnetic field to the other side of the substrate, and the nanosatellite structure may move in a direction toward the substrate to promote macrophage adhesion and M2 differentiation. When the average diameter of the gold nanoparticles is the second average diameter and the distance between the adjacent gold nanoparticles is the second distance, macrophage adhesion may be inhibited and macrophage M1 polarization may be promoted before application of the magnetic field, but macrophage adhesion and M2 polarization may be promoted after application of the magnetic field.

However, when the size of the gold nanoparticles is very large, even if the distance between the gold nanoparticles is large, a plurality of integrin molecules may bind to one gold nanoparticle, and thus integrin clustering may occur and macrophage adhesion may slightly increase.

For example, when the size of the gold nanoparticles is 15 nm to 25 nm (third average diameter) and the distance between the gold nanoparticles in the adjacent nanoassemblies is 18 nm to 22 nm, macrophage adhesion may slightly increase compared to when the size of the gold nanoparticles is 12 nm to 14 nm (second average diameter) and the distance between the gold nanoparticles in the adjacent nanoassemblies is 15 nm to 20 nm (second distance) Thus, in this case, macrophage M2 polarization may be slightly promoted.

Hereinafter, examples of the present invention and comparative examples will be described. However, the following examples are only preferred examples of the present invention, and the scope of the present invention is not limited by the following examples.

Figure 3:
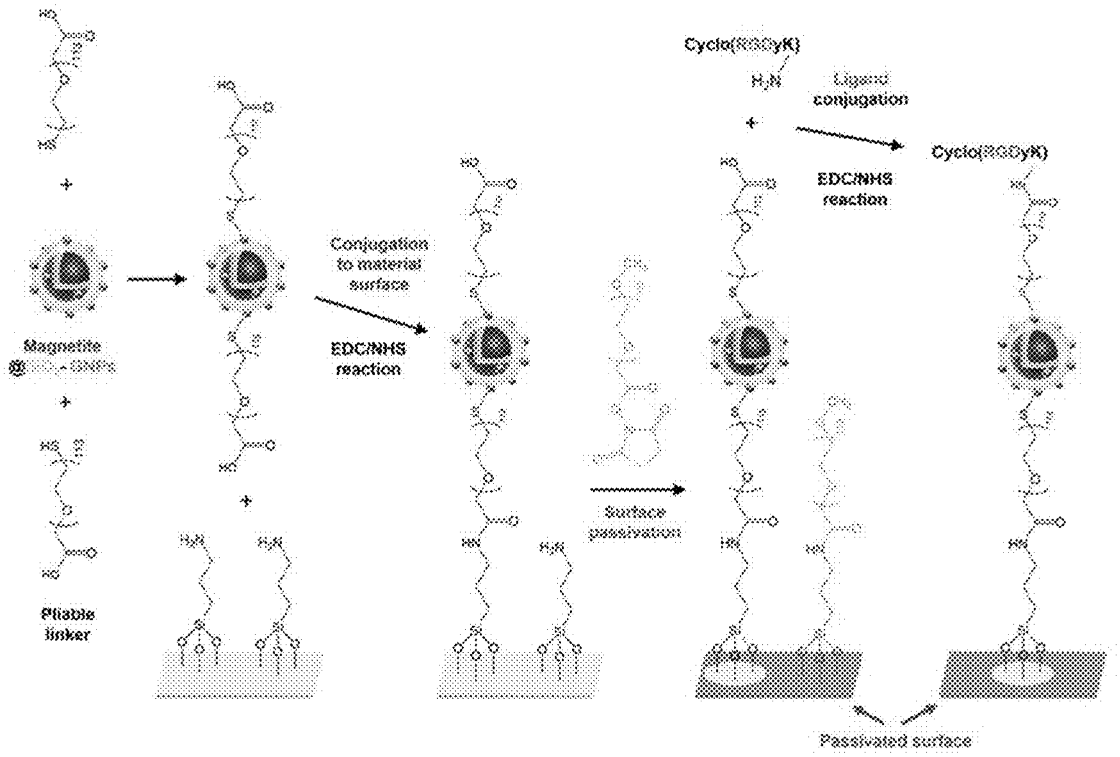
FIG. 3 schematically shows a process for preparing a nanosatellite-substrate complex according to one embodiment of the present invention.

FIG. 3 schematically shows a process of preparing a nanosatellite-substrate complex according to one embodiment of the present invention.

Example 1

Modulation of Only Density of Gold Nanoparticles

1. Preparation of Magnetic Nanoparticles 0.5406 g (2 mmol) of FeCl3-6$H_2$0, 0.4922 g (6 mmol) of sodium acetate, and 2.703 mL of deionized (DI) water were mixed with 50 mL of ethylene glycol. The mixture was mechanically stirred for 3.5 hours at 200° C., washed with ethanol, and then centrifuged three times and suspended in ethanol.

To form an amino functional group on the surfaces of magnetic cores, the surfaces were cored with amino-$SiO_2$. Specifically, 30 mg of magnetic cores were suspended in 60 mL of ethanol. To this suspension, 3 mL of ammonia solution and 9 mL of DI water were serially added. After vigorous shaking of the suspension for 15 minutes, 60 μL of tetraethyl orthosilicate (TEOS) was added thereto. The suspension was then stirred for 1.5 hours, followed by washing with ethanol and centrifugation three times. Then, 0.1 mL of (3-aminopropyl)triethoxysilane (APTES) was added to the suspension, followed by stirring at 80° C. for 3 hours. As a result, the magnetic cores were coated with amino-functionalized silica, thereby preparing magnetic nanoparticles (MNP@amino-$SiO_2$).

Then, the magnetic nanoparticles were washed three times with ethanol and then washed three times with DI water and resuspended in 12 mL of DI water.

2. Preparation of Gold Nanoparticles

Gold nanoparticles to be conjugated to the surfaces of the magnetic nanoparticles were prepared. Specifically, 100 mL of DI water containing 1 mM $HAuCl_4 \cdot 3H_2O$ was stirred at 100° C. for 20 min. 10 mL of DI water containing 38.8 mM sodium citrate tribasic dihydrate water was rapidly added to this boiling solution, followed by stirring for 10 min, which exhibited a yellow to burgundy red color. As a result, gold nanoparticles were prepared.

Then, the gold nanoparticles were in sodium citrate solution prior to their conjugation to the magnetic nanoparticles prepared in 1 above.

3. Conjugation of Gold Nanoparticles to Surfaces of Magnetic Nanoparticles

The suspension containing the gold nanoparticles prepared in 2 above was mixed with 4 mL of the solution containing the magnetic nanoparticles prepared in 1 above, and the mixture was stirred at room temperature overnight to conjugate the gold nanoparticles to the surfaces of the magnetic nanoparticles. The density of the gold nanoparticles conjugated to the surfaces of the magnetic nanoparticles was modulated by controlling the amount of the suspension containing the gold nanoparticles. The amount of each suspension containing the gold nanoparticles is shown in Table 1 below. Thereafter, the reacted suspension was washed twice with DI water and collected using a permanent magnet. The magnetic nanoparticles conjugated with the gold nanoparticles were stabilized in DI water containing 1 wt % polyvinylpyrrolidone (PVP, molecular weight: 55 kDa), and then dispersed in 10 mL of DI water.

4. Conjugation of Polymer Linker 1 mL of DI water containing the magnetic nanoparticles conjugated with the gold nanoparticles was dispersed in 1 mL of 0.01% sodium dodecyl sulfate solution, and then coated with a poly(ethylene glycol) (PEG) linker. As the linker, carboxymethyl-PEG-thiol (molecular weight: 5 kDa; Laysan Bio, Inc.; catalog number: CM-PEG-SH-5000-5g) was used. The linker in an amount determined depending on the density of the gold nanoparticles prepared in 3 above was mixed with 1 mL of the dispersion, and the mixture was stirred for 3 hour to facilitate the Au—S bonding reaction between the linker and the gold nanoparticles. The mixture was washed three times with DI water and then dispersed in 50 mM of 2-ethanesulfonic acid buffer. The amount of the linker is shown in Table 1 below.

5. Conjugation to Substrate

As a substrate, a cell culture-grade glass coverslip having a size of 22 mm×22 mm was used. The substrate was incubated in a mixture of APTES and ethanol (1:19) for 12 hours, followed by washing with ethanol and then with DI water. As a result, the substrate was aminated.

1 mL of the product prepared in 4 above was activated by mixing with 0.05 mL of 20 mM N-(3-dimethylaminopropyl)-N'-ethylcarbodiimide hydrochloride (EDC) solution and 0.05 mL of 20 mM N-hydroxysulfosuccinimide (NHS) solution, followed by stirring for 1 hour. The EDC/NHS-activated material was dispersed in 5 mL of DI water and then reacted with the aminated substrate through optimization of the reaction time. The substrate coated with the MNPs decorated with AuNPs was washed with DI water and then with phosphate-buffered saline (PBS). The reaction time was set differently depending on the density of the gold nanoparticles and is shown in Table 1 below. The substrate conjugated with the PEGylated gold nanoparticles was washed with DI water and then with phosphate-buffered saline (PBS).

6. Conjugation of Ligand

To minimize non-RGD ligand-specific macrophage adhesion, the remaining area of the substrate, which was not covered by the PEGylated gold nanoparticles, was deactivated with 2 mL of DI water containing 0.1 mM methoxy-PEG-succinimidyl-carboxymethyl-ester (molecular weight: 5 kDa; Laysan Bio, Inc.; catalog number: M-SCM-5000) and 4 μL of N,N-Diisopropylethylamine (DIPEA) for 2 hours in the dark, followed by washing with DI water. The substrate was shaken in 0.1 mL of PBS containing 1 mM amine group-bearing RGD peptides (Cyclo-(RGDyK); AS-61183-5; AnaSpec, Inc.) in the dark overnight, and then washed with DI water, thereby conjugating the RGD ligand.

TABLE 1

| | Amount of gold nanoparticles added | Amount of linker added | Time of reaction between PEGylated gold nanoparticles and substrate | Gold nanoparticle density (number of gold nanoparticles per magnetic nanoparticle) | Expressions in figures |
|---|---|---|---|---|---|
| Example 1-1 | 2.5 mL | 0.05 mL | 90분 | 39 ± 6 | Low AuNP density |
| Example 1-2 | 8.3 mL | 0.1 mL | 40분 | 108 ± 11 | Moderate AuNP density |
| Example 1-3 | 25 mL | 0.15 mL | 20분 | 171 ± 24 | High AuNP density |

Example 2

A nanosatellite-substrate complex was prepared in which the average diameter of gold nanoparticles was 7 nm and the distance between adjacent gold nanoparticles was 3 nm.

1. Preparation of Magnetic Nanoparticles 2.70 of deionized (DI) water containing 0.54 g (2 mmol) of iron (III) chloride hexahydrate ($FeCl_3 \cdot 6H_2O$) and 0.49 g (6 mmol) of sodium acetate (NaOAc) was mixed with 50 mL of ethylene glycol.

The mixture was heated to 200° C. and mechanically stirred for 3.5 hours. Then, the mixture was washed with ethanol and centrifuged. In this process, iron oxide cores were formed. The iron oxide cores were suspended in ethanol.

To 60 mL of ethanol containing 30 mg of the iron oxide core suspension, 3 mL of ammonia solution and 9 mL of DI water were added. After vigorous shaking of the solution, 60 μL of tetraethyl orthosilicate (TEOS) was added thereto. The solution was stirred for 1.5 hours, washed with ethanol, centrifuged, and then suspended in 12 mL of ethanol. 10 mL of 2-propanol was added to the suspension which was then sonicated for 10 minutes. To the suspension, 0.1 mL of (3-aminopropyl)triethoxysilane (APTES) was added, followed by mechanical stirring at 80° C. for 3 hours. In this process, the iron oxide cores were coated with silica having an amino group to form magnetic nanoparticles having a core-shell structure. The magnetic nanoparticles were washed with ethanol and DI water, and then suspended in 4 mL of DI water.

2. Preparation of Gold Nanoparticles (1) Preparation of Gold Seed Particles 2.5 mL of DI water containing 5 mM of gold (III) chloride hydrate ($HAuCl_4 \cdot 3H_2O$), 2.5 mL of DI water containing 2.5 mM of trisodium citrate dihydrate ($Na_3Cit$), and 45 mL of DI water were mixed together at room temperature and stirred vigorously for 10 minutes. 1.5 mL of DI water containing 0.1 M sodium borohydride ($NaBH_4$), which is a strong reducing agent, was added to the mixture which was then vigorously stirred for 10 minutes. When the solution changed from yellow to orange-red color, indicating that gold nanoparticles having a diameter of 3 nm were formed, the suspension was stabilized for 6 hours and then stored at 4° C.

(2) Growth of Gold Seed Particles

Gold seed particles were conjugated to magnetic nanoparticles and then grown, thus preparing gold nanoparticles.

25 mL of a suspension containing gold seed particles having a diameter of 3 nm, and 4 mL of a suspension containing magnetic nanoparticles were mixed together and stirred at room temperature for 16 hours, so that the gold seed particles were bound to the amino groups on the surfaces of the magnetic nanoparticles. The resulting suspension was washed with DI water and collected using a permanent magnet. The magnetic nanoparticles conjugated with the 3-nm-diameter gold seed particles were stabilized with 10 mL of DI water containing 1 wt % of polyvinylpyrrolidone (PVP, molecular weight: 55,000 Da) for 3 hours, and then dispersed in 20 mL of DI water.

In order to grow the gold seed particles, 4 mL of DI water containing L-ascorbic acid (LAA, 20 mM) as a reducing agent is added to the dispersion which was then mixed with 200 mL of DI water containing 1 wt % of PVP and stirred for 5 minutes. 1 mL of DI water containing 5 mM $HAuCl_4 \cdot 3H_2O$ was added to the suspension with vigorous stirring, followed by stirring for 10 minutes. The process of adding 1 mL of DI water containing 5 mM of $HAuCl_4 \cdot 3H_2O$ was performed once to grow the gold seed particles into gold nanoparticles having a diameter of 7 nm, and the gold nanoparticles were washed and then suspended in 10 mL of DI water.

3. Conjugation to Substrate

As a substrate, a cell culture-grade glass coverslip having a size of 6 mm×6 mm was prepared. The surface of the substrate was aminated with treatment with a mixture of 3-aminopropyltriethoxysilane (APTES) and ethanol (1:19) for 12 hours in the dark, followed by washing with ethanol and DI water.

2 mL of DI water containing the magnetic nanoparticles conjugated with the gold nanoparticles was suspended in 2 mL of 0.01% sodium dodecyl sulfate solution, and then the surfaces of the gold nanoparticles were coated using 0.1 mL of DI water containing a polymer linker (carboxymethyl-PEG-thiol; 1 mM, molecular weight: 5,000 Da; Laysan Bio, Inc.; catalog #:CM-PEG-SH-5000). In the coating process, the solution was vigorously stirred for 3 hours to form bonds between the gold nanoparticles and the thiol groups of the polymer linker. Thereafter, the suspension was washed with DI water and added to 1 mL of 2-ethanesulfonic acid buffer (50 mM). In this process, the polymer linker was conjugated to the gold nanoparticles.

0.05 mL of DI water containing 20 mM N-(3-dimethylamiropropyl)-N'-ethylcarbodiimide hydrochloride (EDC) and 20 mM N-hydrosulfosuccinimide solution (NHS) was added to the gold nanoparticles, followed by vigorous stirring at room temperature for 1 hour.

Thereafter, the product composed of the gold nanoparticles conjugated with the polymer linker was conjugated to the aminated substrate by 70 minutes of incubation. Next, the substrate was washed with DI water and then with phosphate-buffered saline (PBS)

4. Conjugation of Ligand

The remaining area of the aminated substrate, which was not conjugated with the polymer linker on gold nanoparticles, was deactivated with 0.1 mM methoxy-PEG-succinimidyl-carboxymethyl-ester (JenKem, catalog #: M-SCM- 5000, 0.1 mM) in the dark for 2 hours, followed by washing with DI water. Thereafter, the substrate was incubated with PBS containing an RGD ligand (Cyclo(-RGDyK), AnaSpec, Inc., catalog #: AS-61183-5, 1 mM) having an amino group (lysine residue) under shaking for 16 hours in the dark, followed by washing with DI water. In this process, a nanosatellite-substrate complex was formed.

Example 3

A nanosatellite structure was prepared by modulating the diameter of gold nanoparticles to 13 nm and the distance between adjacent gold nanoparticles to 17 nm, which differ from those in Example 2. The nanosatellite structure was prepared in the same manner as in Example 2, except for the preparation process described below.

1. Preparation of Gold Nanoparticles 1 mM $HAuCl_4 \cdot 3H_2O$ was dissolved in 100 mL of DI water, heated to 100° C., and then stirred for 20 minutes. 10 mL of DI water containing 39 mM $Na_3Cit$ was added to the solution, followed by stirring for 10 minutes. When the color of the solution changed from yellow to burgundy red color, indicating that gold nanoparticles having a diameter of 13 nm were formed, the suspension was stabilized in 100 mL of DI water containing 1 mM $Na_3Cit$.

8 mL of the suspension containing the gold nanoparticles having a diameter of 13 nm was mixed with 4 mL of a suspension containing magnetic nanoparticles, and the mixture was stirred at room temperature for 16 hours, thereby conjugating the gold nanoparticles to the amino groups on the surfaces of the magnetic nanoparticles. Next, the suspension was washed with DI water and collected using a permanent magnet. Next, the magnetic nanoparticles conjugated with the gold nanoparticles were stabilized in 10 mL of DI water containing 1 wt % of PVP for 3 hours, and then dispersed in 10 mL of DI water.

2. Conjugation to Substrate

The product composed of the gold nanoparticles conjugated with the polymer linker was conjugated to the aminated substrate by 55 minutes of incubation.

Example 4

A nanosatellite structure was prepared by modulating the diameter of gold nanoparticles to 20 nm and the distance between adjacent gold nanoparticles to 20 nm, which differ from those in Example 2. The nanosatellite structure was prepared in the same manner as in Example 2, except for the preparation process described below.

1. Preparation of Gold Nanoparticles 4 mL of a suspension containing gold nanoparticles having a diameter of 13 nm was mixed with 88 mL of DI water, and the mixture was stirred at 90° C. for 20 minutes. To this suspension, 0.8 mL of DI water containing 60 mM $Na_3Cit$ and 0.4 mL of DI water containing 25 mM $HAuC1_4 \cdot 3H_2O$ were added, followed by stirring for 30 minutes. When the color of the solution changed from purple to burgundy red, indicating that gold nanoparticles have grown, and gold nanoparticles having a diameter of 20 nm were formed. The solution containing the gold nanoparticles was resuspended in 100 mL of DI water containing 1 mM $Na_3Cit$.

88 mL of the suspension containing the gold nanoparticles having a diameter of 20 nm was mixed with 4 mL of magnetic nanoparticles, and the mixture was stirred at room temperature for 16 hours, thereby conjugating the gold nanoparticles to the amino groups on the surfaces of the magnetic nanoparticles. The suspension was washed with DI water and collected using a permanent magnet. The magnetic nanoparticles conjugated with the gold nanoparticles having a diameter of 20 nm were stabilized in 10 mL of DI water containing 1 wt % of PVP for 3 hours, and then dispersed in 10 mL of DI water.

2. Conjugation to Substrate

The product composed of the gold nanoparticles conjugated with the polymer linker was conjugated to the aminated substrate by 40 minutes of incubation.

Example 5

Gold Shells

A nanosatellite-substrate complex was prepared in which the entire surfaces of magnetic nanoparticles were coated with gold nanoparticles (gold shells).

As described in Example 2, gold seed particles having a diameter of 3 nm were conjugated to the surfaces of magnetic nanoparticles and the suspension was stabilized with PVP.

3 mL of DI water containing 5 mM $HAuCl_4 \cdot 3H_2O$ was mixed with 197 mL of DI water containing 50 mg of potassium carbonate ($K_2CO_3$, 0.36 mmol), followed by stirring at room temperature for 12 hours. The solution was mixed with 0.125 mL of DI water containing 3.7 wt % of formaldehyde, and the mixture was added to the suspension containing the magnetic nanoparticles conjugated with the gold seed particles having a diameter of 3 nm, 10 times at intervals of 2 minutes. The resulting suspension was shaken for 1 hour, washed with DI water, and then dispersed in 1 mL of DI water. The solution changed from transparent orange-red color to purple-blue color, indicating that gold shells were formed.

In addition, the product composed of the gold nanoparticles conjugated with the polymer linker was conjugated to the aminated substrate by 25 minutes of incubation.

Other procedures were performed in the same manner as in Example 2.

Comparative Examples

1. Comparative Example 1

A nanosatellite structure was prepared in the same manner as in Example 1, except that 1 mM RAD peptide (amine group-bearing RAD peptide, Cyclo(-RADyK); AS-62351; AnaSpec, Inc.) was used instead of the RGD ligand.

2. Comparative Example 2

For comparison, a nanosatellite-substrate complex, in which gold nanoparticles had a diameter of 7 nm and the distance between adjacent gold nanoparticles was 18 nm, was prepared in the same manner as Example 2.

In the same manner as in Example 2, a suspension was prepared by conjugating gold seed particles having a diameter of 3 nm to magnetic nanoparticles. Briefly, 0.5 mL of DI water containing 5 mM $HAuCl_4 \cdot 3H_2O$, 0.5 mL of DI water containing 200 mM potassium iodide (KI), 3 mL of DI water containing 20 mM LAA, and 40 mL of DI water containing 1 wt % PVP were mixed together and stirred at room temperature for 30 minutes. To this solution containing gold seed particles having a diameter of 3 nm, 20 mL of a suspension containing magnetic nanoparticles was added, and the resulting suspension was shaken for 1 hour, washed with DI water, and then dispersed in 10 mL of DI water.

In addition, the product composed of the gold nanoparticles conjugated with the polymer linker was conjugated to the aminated substrate by 90 minutes of incubation.

3. Comparative Example 3

A nanosatellite-substrate complex was prepared in the same manner as in Example 1, except that a scrambled RAD ligand (amine group-exhibiting scrambled ligand [Cyclo(-RADyK), AnaSpec, Inc., catalog #: AS-62351, 1 mM]) was used instead of the RGD ligand.

4. Comparative Example 4

A nanosatellite-substrate complex without a ligand was prepared in the same manner as in Example 2, except that the RGD ligand was not used.

The characteristics of the nanosatellite-substrate complexes prepared in the Examples and the Comparative Examples were evaluated.

In experiments on the nanosatellite-substrate complex of the present invention and the drawings for the experiments, the expressions for each case are as follows.

In the cases in which the nanosatellite-substrate complexes having a difference only in the density of the gold nanoparticles conjugated to the surfaces of the magnetic nanoparticles were prepared (Example 1), the cases were classified based on the density of the gold nanoparticles. The density of the gold nanoparticles was calculated as the number of gold nanoparticles per magnetic nanoparticle, and the case in which the density of the gold nanoparticles was 39±6 was expressed as "Low AuNP density" or "Low". Moreover, the case in which the density of the gold nanoparticles was 108±11 was expressed as "Moderate AuNP density" or "Moderate", and the case in which the density of the gold nanoparticles was 171±24 was expressed as "High AuNP density" or "High".

In addition, In the cases in which the nanosatellite-substrate complexes were prepared by modulating the diameter of gold nanoparticles and the distance between adjacent gold nanoparticles (Examples 2 to 4), the cases were expressed as the diameter of and distance between the gold nanoparticles. For example, the case, in which the diameter of gold nanoparticles was 7 nm and the distance between adjacent gold nanoparticles was 3 nm, was expressed as 7-3 (nm); the case, in which the diameter of gold nanoparticles was 7 nm and the distance between adjacent gold nanoparticles was 18 nm, was expressed as 7-18 (nm); the case, in which the diameter of gold nanoparticles was 13 nm and the distance between adjacent gold nanoparticles was 17 nm, was expressed as 13-17 (nm); and the case, in which the diameter of gold nanoparticles was 20 nm and the distance between adjacent gold nanoparticles was 20 nm, was expressed as 20-20 (nm). Other values were also expressed in the same manner as above. In addition, the case the diameter of gold nanoparticles was 7 nm was expressed as "small" or "small ligands"; the case in which the diameter of gold nanoparticles was 13 nm was expressed as "medium" or "medium-sized ligands"; and the case in which the diameter of gold nanoparticles was 20 nm was expressed as "large" or "large ligands". In addition, the case in which the distance between adjacent gold nanoparticles was 3 nm was expressed as "pseudo-connected", and the case in which the distance was greater than 3 nm was expressed as "disconnected".

The case in which a magnetic field was applied to the nanosatellite-substrate complex to compress the first linker and pull the nanosatellite structure toward the substrate was expressed as "Linker compression", "Linker squeezing", "Ligand anchoring", "+Anchor", "anchoring", "Lower Mag", "Magnetic "downward" ligand Motion", or "nanosatellite structure was fastened to the substrate". On the other hand, the case in which a magnetic field was applied to the nanosatellite-substrate complex to stretch the first linker and pull the nanosatellite structure in a direction away from the substrate was expressed as "Linker stretching", "Pliable linker", "Upper Mag", "Magnetic "upward" ligand motion", or "nanosatellite structure was not fastened". The case in which no magnetic field was applied was not expressed or was expressed as "No Mag" or "−Anchor".

Experimental Methods

1. Vibrating Sample Magnetometry (VSM) Analysis

The magnetic moments of the magnetic nanoparticles and the nanosatellite structures were analyzed via VSM (EV9-380, Microsense) measurements. VSM measurements were carried out at room temperature under an application of magnetic field strength (H) from −19,000 to 19,000 Oe to obtain hysteresis loops. After normalization to the dry weight of each sample, the resulting magnetic moment was presented.

2. X-Ray Diffraction (XRD) Analysis

The crystalline phases of co-present $Fe_3O_4$ and Au in the magnetic nanoparticles and the nanosatellite structures were characterized by performing XRD (D/MAX-2500V/PC, Rigaku) analysis. XRD measurements were performed with Cu Kα radiation in the diffraction spectrum of $20° < 2\theta < 70°$. Diffraction peaks were indexed via comparison with reference data of the $Fe_3O_4$ and Au phases[1].

3. Dynamic Light Scattering (DLS) Analysis

The sizes of and distances between the magnetic nanoparticles, the gold nanoparticles, the gold nanoparticle-conjugated magnetic nanoparticles and the nanoassemblies conjugated to the magnetic nanoparticle surface were analyzed via DLS (Zetasizer Nano ZS90 Malvern Panalytical) measurements at room temperature.

4. Energy-Dispersive X-ray Spectroscopy (EDS) Mapping

In order to identify iron (Fe), silicon (Si) and gold (Au) elements present in the nanosatellite structure, EDS mapping was performed using two SDD detectors.

5. High-Angle Annular Dark-Field Scanning Transmission Electron Microscopy (HAADF-STEM)

The nanosatellite structures were imaged by using HAADF-STEM (a probe Cs-corrected JEM ARM200CF, JEOL Ltd.). The measurement conditions were 200 kV, a measured phase of 27 to 28 mrad, a convergence semi-angle of 21 mrad, a collection semi-angle of 90 to 370 mrad, a spherical aberration (C3) of 0.5 to 1 μm, electron probe sizes of 8C (1.28 Å) and 9C (1.2 Å), a pixel area of 2,048×2,048, an emission current of 8 to 13 μA, a probe current range of 10 to 20 μA, and a pixel dwell time of 10 to 15 μs. The darker and brighter shades of the acquired HAADF-STEM images indicate magnetic nanoparticles and homogeneously distributed nanoassemblies, respectively. The diameter of gold nanoparticles, the edge-to-edge spacing of adjacent gold nanoparticles, the number of nanoassemblies per magnetic nanoparticle, and the total area of nanoassemblies per magnetic nanoparticle were all computed via ImageJ software on the acquired HAADF-STEM images.

6. High Resolution-Transmission Electron Microscopy (HR-TEM)

HR-TEM imaging was performed at 200 kV using a Cs-corrected JEM ARM200C probe with 2.5-5 million magnifications to characterize the atomic arrangements of crystalline magnetic nanoparticles and gold nanoparticles. Other settings were identical to those of HAADDF-STEM imaging.

7. UV-Vis Spectroscopy Analysis

The UV-Vis spectra (Shimadzu UV-1800) for gold nanoparticles and nanoassemblies conjugated to magnetic nanoparticles were measured in a wavelength range of 350 to 800 nm.

8. Fourier Transform Infrared Spectroscopy (FTIR)

Sequential changes in chemical bonds following PVP stabilization of the gold nanoparticle-conjugated magnetic nanoparticles, PEGylation of gold nanoparticles, and RGD ligand conjugation were confirmed from acquired FTIR (Nicolet iS10; Thermo Fisher Scientific) spectroscopy measurements. The samples in suspension were dried and densely packed into potassium bromide (KBr) pellets prior to taking measurements. The absorption peaks were indexed with the corresponding chemical bonds after their sequential changes.

9. Scanning Electron Microscopy (SEM) Imaging

The distance between adjacent nanoassemblies conjugated to magnetic nanoparticles, the density distribution and the diameter of gold nanoparticles were verified via SEM imaging (FEI from Quanta 250 FEG). The dried samples were subjected to platinum sputter coating for 90 seconds prior to SEM imaging. The number of magnetic nanoparticle surface-conjugated nanoassemblies per $\mu m^2$ was determined from four different SEM images. The density of the nanoassemblies was computed by calculating the total area of the nanoassemblies per magnetic nanoparticle and multiplying it by the number of magnetic nanoparticle-conjugated nanoassemblies per $\mu m^2$.

10. Transmission Electron Microscopy (TEM)

The precise control of gold nanoparticle growth based on gold seed particles, the size of magnetic nanoparticles, and the distance between adjacent gold nanoparticles were investigated by using TEM imaging (Tecnai 20, FEI). These were computed from eight different TEM images using ImageJ software.

11. In Situ Atomic Force Microscopy (AFM) Imaging

In order to analyze the movement of the nanosatellite structure by the application of a magnetic field, in situ magnetic AFM imaging (Asylum Research, XE-100 Systems) was performed. Each sample was imaged in AC in air mode at room temperature using an SSS-SEIHR-20 AFM cantilever (Nanosensors) with a force constant of 5 to 37 N/m and a resonance frequency of 96 to 175 kHz. For this imaging, a permanent magnet (300 mT) was placed at the lower side of the substrate or the upper side of the nanosatellite structure, and the movement of the nanosatellite structure was monitored. Igor Pro 6.12A and ImageJ software were used to analyze images showing contrast changes corresponding to quantification of height changes.

12. Confocal Immunofluorescence Microscopy Analysis

In order to evaluate the effect of the nanoassembly density and the application of a magnetic field on macrophage adhesion and polarization, macrophage cultures were fixed in 4% paraformaldehyde for 15 min, followed by washing with PBS. The fixed cells were blocked using a blocking buffer solution (PBS containing 3% bovine serum albumin and 0.1% Triton-X-100) at 37° C. for 1 hour and treated with primary antibodies in the blocking buffer solution at 4° C. overnight, followed by washing with PBS. The primary antibody-treated cells were incubated with a blocking buffer solution containing fluorophore-tagged secondary antibodies, phalloidin, and DAPI at room temperature for 40 min in the dark, followed by washing with PBS. Cells were imaged under a confocal microscope (LSM700, Carl Zeiss) by applying similar exposure conditions to all of the compared groups. The acquired images were quantified with ImageJ software.

Macrophage adhesion was determined by DAPI-positive cell numbers as well as the adherent cell area and the elongation factor of the F-actin-stained cells whereas macrophage polarization, paxillin expression, and F-actin assembly were quantified by calculating fluorescence intensities. The actin-stained cell was used to draw line of the cell boundary and the identical line was then applied to the cell stained with specific antibodies of M1 (iNOS) and M2 (Arg-1) polarization markers or paxillin. In addition, histogram function was used to determine fluorescence intensities within the line of cell boundary to estimate the degree of macrophage polarization or paxillin expression.

13. Integrin Binding to Nanosatellite-Substrate Complex

The binding and clustering efficiencies of integrin β1 to the ligand on the nanosatellite-substrate complex were obtained by immersing them in integrin β1 (50 μg/mL) in PBS at 4° C. for 16 hours. Following this, the substrate surface was treated with 4% paraformaldehyde at room temperature for 10 min to fix the ligand-bound and clustered integrin β1, which was subsequently immunofluorescently stained. The fluorescence intensities of integrin β1 were computed using five different immunofluorescently stained images.

14. Immunolabeling of Integrin Binding and Clustering

In order to examine whether integrin β1 binding and clustering to the ligand of the nanosatellite-substrate complex, immunogold labeling analysis was performed through SEM imaging. 40 nm-sized gold nanoparticles were used for immunogold labeling to distinguish them from the gold nanoparticles used on the nanosatellite-substrate complex.

First, 50 mL of DI water containing $HAuCl_4 \cdot 3H_2O$ in (1 mM) was stirred intensely for 15 min while boiling, mixed with 5 mL of DI water containing 1% sodium citrate solution, and then boiled for another 15 min. The solution was then cooled to room temperature to obtain 40 nm-sized gold nanoparticles (hereinafter referred to as 40-gold nanoparticles), which were then coated with secondary antibody through an incubation in a blocking solution containing the secondary antibody (Abcam, goat anti-mouse, (H+L) IgG, 1:100) under mild shaking at 37° C. for 16 hours, followed by rinsing with DI water. The blocking solution used here was 1,4 piperazine bis(2-ethanosulfonic acid) buffer (PIPES) buffer (0.1 M, pH 7.4) supplemented with 1% bovine serum albumin (BSA) and 0.1% Tween 20.

Prior to labeling with the secondary antibody-coated 40 nm gold nanoparticles, macrophages after culturing were rinsed with PIPES (0.1 M, pH 7.4) and then treated with 4% PFA for 12 min to fix the cells. These were rinsed with PBS and then permeabilized with a blocking solution containing Triton X-100 (0.5%) for 1 min, followed by treatment in the blocking solution for another 1 hour, and then rinsed with 1% BSA solution for subsequent incubation in 5% goat serum solution for 12 min. The blocking solution used here was a solution supplemented with magnesium chloride ($MgCl_2$), sodium chloride (NaCl), sucrose, and HEPES (pH 7.2).

The macrophages were placed in PIPES buffer containing the secondary buffer-coated 40-gold nanoparticles for 14 hours and labeled with the 40-gold nanoparticles. The macrophages having integrin β1 immunogold-labeled with the 40-gold nanoparticles were rinsed with PIPES buffer and then completely fixed with 2.5% glutaraldehyde for 5 min. After rinsing again with PIPES buffer, they were placed in PIPES buffer containing 1% osmium tetroxide for 1 hour to elevate the contrast of the macrophages in the SEM images. After serial rinsing with PIPES buffer and DI water, they were dried for SEM imaging. In the SEM images, pseudo-colors of red and green were used for macrophages and 40-gold nanoparticle-labeled integrin β1, respectively. The number of 40-gold nanoparticle-labeled integrin β1 clusters per nanosatellite structure was counted in four different SEM images.

15. Macrophage Culture with Nanosatellite-Substrate Complex

To evaluate the effect of magnetic field application to the nanosatellite-substrate complex on the adhesion and polarization of macrophages, macrophages (RAW 264.7, passage 5, ATCC) were cultured. Sterilization of the nanosatellite-substrate complex was conducted under ultraviolet irradiation for 1 hour prior to the culture. Macrophages were cultured on the nanosatellite-substrate complex at a density of $1\times10^5$ cells/$cm^2$ under basal growth medium with DMEM containing 10% heat-inactivated fetal bovine serum and 50 U/mL of penicillin and streptomycin antibiotics at 37° C. under 5% $CO_2$.

The adhesion of macrophages was investigated in a state in which no magnetic field was applied and in a state after the nanosatellite structure was moved by applying a magnetic field (270 mT). The adhesion of macrophages was investigated for the case in which the RGD ligand was conjugated, the case in which the scrambled RAD sequence was conjugated, the case in which there was no ligand, and the case in which the diameter of and distance between gold nanoparticles were varied.

As the polarization medium, the M1-inducing medium was basal growth medium containing M1-inducing stimulators of 10 ng/mL each of lipopolysaccharide (LPS) and recombinant interferon-gamma (IFN-γ), and the M2-inducing medium was basal growth medium containing M2-inducing stimulators of 20 ng/mL each of interleukin (IL)-4 and IL-13.

In addition, the adhesion-aided M2 polarization of macrophages promoted was investigated with specific inhibitors of actin polymerization (2 μg/mL of cytochalasin D), myosin II (10 μM blebbistatin), or ROCK (50 μM Y27632).

16. Reverse Transcription-Quantitative Polymerase Chain Reaction (RT-qPCR)

In order to examine the effect of the nanoassembly density and the application of a magnetic field on macrophage polarization, macrophage cultures were lysed with Trizol (1 mL per sample) following M1 or M2 polarization stimulation. RNA (900 ng per sample) was reverse-transcribed to obtain cDNA using a High Capacity RNA-to-cDNA kit. The StepOne Plus Real-Time PCR System (Applied Biosystems) was used to run real-time PCR cycles with Sybr Green assays and primer sequences against M1-specific (iNOS and TNF-α) and M2-specific (Arg-1 and Ymi) genes. The gene expression profiles were presented as the relative fold expression following their normalization to that of the GAPDH housekeeping gene.

17. Polarization of Human Primary Macrophages by Application of Magnetic Field

To explore the effect of magnetic field application on the polarization of human primary macrophages via relevant mRNA expression levels, qRT-PCR gene array profiling was performed using macrophage (M1 and M2) polarization-specific markers. Briefly, the present inventors collected human buffy coat fraction after the removal of red blood cells (RBCs) by RBC lysis buffer and the following Ficoll density gradient centrifugation. Next, the purified human peripheral blood mononuclear cells (hPBMCs; CD45+ hPBMCs confirmed by PerCP anti-human CD45 antibody (Biolegend, USA)-based flow cytometry analysis) were used for the isolation of CD14+ monocytes. The monocytes (CD14+ cells) were purified using Miltenyi CD14-MicroBead+Fc Ab isolation kit following the manufacturer's protocol. Briefly, the cells were captured to the magnetic column using magnetic microbead conjugated CD14 antibody and the purified cells were washed three times using RB buffer, which was analyzed by flow cytometry. Cells were then cultured in a growth media supplemented with granulocyte macrophage-colony stimulating factor (GM-CSF, 25 ng/mL) for 6 days. The differentiated macrophage-like monocytes were polarized by culturing them in M1 (GM-CSF-with 10 ng/mL each of LPS and IFN-γ)- and M2 (GM-CSF with 20 ng/mL each of IL-4 and IL-10)-specific medium in a state in which no magnetic field was applied and in a state in which a magnetic field was applied for 36 hours.

The cultured macrophages were analyzed to identify the gene expression related to polarization specific macrophage markers (40 genes). Briefly, the cultured macrophages were retrieved for RNA extraction using mirVana-RNA extraction kit (ThermoFisher, USA) according to the total RNA extraction protocol. The extracted RNA was used for cDNA synthesis using QuantaBio cDNA Synthesis Kit (QuantaBio, Beverly, USA) according to the manufacturer's protocol. The cDNA was then used for qPCR-based gene expression analysis for the human macrophage polarization markers using GeneQuery™ Human Macrophage Polarization Markers qPCR Array Kit (ScienCell, Carlsbad, USA) using EvaGreen PCR Reagent (CHAI, Santa Clara, USA) according to the manufacturers' protocols. The present inventors analyzed the gene expression patterns (M1, M2, and other activation/resting markers) as heat maps according to the manufacturer's protocol.

18. Cytokine Secretion Analysis via Enzyme-Linked Immunosorbent Assay (ELISA)

To quantify the levels of cytokines secreted by macrophages cultured in M1 or M2 polarization medium using the nanosatellite-substrate complex, ELISA was performed. Briefly, macrophages were cultured with the nanosatellite-substrate complex in M1- or M2-inducing medium, and then the culture media were collected to measure the secreted amounts of cytokines (TNF-α and IL-10) using ELISA kit (abcam, SimpleStep ELISA Kits). An absorbance reading at 450 nm was recorded to quantify the secreted levels of cytokines.

19. Macrophage Polarization Analysis Using Western Blotting and Protein Quantitation The effect of the diameter of gold nanoparticles and the distance between adjacent gold nanoparticles in the nanosatellite-substrate complex on the polarization of macrophages was analyzed via western blotting and protein quantitation. After the nanosatellite-substrate complexes under different conditions were incubated with macrophages in basal medium supplemented with M1 or M2 polarization stimulators, macrophage proteins were extracted using a mixture of PRO-PREP™ protein extraction buffer (iNtRON biotechnology, 400 μL) and a protease inhibitor cocktail (10 μL) for 20 min and then centrifuged at 4° C. Quantitation of the total protein concentration was carried out using a Thermo Scientific™ Pierce™ BCA Protein Assay Kit. The protein samples were mixed with loading dye and subjected to boiling at 100° C. for 8 min to denature them. The denatured proteins were separated by running 10% sodium dodecyl sulfate (SDS)-polyacrylamide gel electrophoresis (PAGE) at 110 V for 55 min, and then the proteins in the gels were transferred to polyvinylidene fluoride (PVDF) membranes via electroblotting. The transferred proteins were further subjected to electrophoresis at 120 V for 90 min and then blocked using blocking buffer [tris-buffered saline with 0.1% Tween 20 (TBST) and 5% skimmed milk] at 4° C. for 16 hours, followed by rinsing with TBST buffer. The blocked membranes were placed in a blocking buffer containing primary antibodies for iNOS (M1 polarization marker, 135 kDa), Arg-1 (M2 polarization marker, 37 kDa), and GAPDH (36 kDa) at room temperature for 1 hour, followed by rinsing with TBST buffer. The treated membranes were placed in a blocking buffer containing anti-horseradish peroxidase (HRP)-conjugated secondary antibodies at room temperature for 1 hour, followed by rinsing with TBST buffer. The membranes were then placed in ECL western blotting reagent (Immobilon Western Chemiluminescent HRP Substrate, MERCK-Millipore) and visualized via a Linear Image Quant LAS 4000 mini chemiluminescent imaging system. The relative expression levels of the target proteins were computed after normalization to GAPDH expression.

20. Flow Cytometry Analysis of Host Cells

For flow cytometry analysis of host macrophage regulation, recruited host macrophages that had adhered to the ligands were trypsinized and rinsed with ice-cold PBS supplemented with 10% FBS. The suspended host cells were centrifuged and fixed in the suspension with 4% PFA for 10 min. They were then immersed in a blocking solution of PBS supplemented with 3% BSA at room temperature for 1 hour. The blocked host cells were immersed in a blocking solution containing primary antibodies of CD68 to estimate the inflammatory response, CD163 to estimate anti-inflammatory/pro-healing M2 phenotype-specific response, or isotype control at room temperature for 1 hour. Following this, the treated host cells were rinsed with PBS and centrifuged.

They were then immersed in fluorochrome-labeled secondary antibodies in the buffer solution at room temperature for 30 min in the dark. The fluorochrome-labeled host cells were rinsed with a solution of PBS supplemented with 3% BSA and 1% sodium azide and then subjected to fluorescence-activated single cell sorting (FACS) Calibur measurements by using BD CellQuest Pro software (BD Biosciences). The calculated data were presented in histograms using FlowJo software and the measured fluorescence signals were quantified to present the mean fluorescence intensity respective to the isotype control.

21. In Vivo Experiment on Nanosatellite-Substrate Complex

An experiment was conducted to examine whether the results of the in vitro experiment on the effect of the nanosatellite-substrate complex on the adhesion and polarization of macrophages was identical to those in cells. The experiment was conducted on two-month-old balb/c mice after obtaining approval from the Institutional Animal Care and Use Committee at Korea University. The mice were anesthetized through an intraperitoneal injection of a mixture of 75 μL of alfaxan and 25 μL of rompun. An incision approximately 1.5 cm long was made on the backs of the mice. The substrate-substrate complex was subcutaneously implanted and the incision was sutured. Each 40 ng of interleukin (IL)-4 and IL-13 were then injected onto the implanted substrate-substrate complex.

The adhesion and polarization of the recruited macrophages were assessed by attaching the permanent magnet (270 mT) to the skin on the backs of the mice or to the skin on the abdomens of the mice (i.e. at the lower side of the substrate) to induce movement of the nanosatellite structure. The present inventors used five mice per group for four groups, which were repeated twice. Therefore, a total of 40 mice were used.

At 24 hours after implantation, the nanosatellite-substrate complex was retrieved for confocal imaging of the immunofluorescence and gene expression analysis to explore the adhesion and polarization of the recruited macrophages. The effect of implantation of the nanosatellite-substrate complex on the tissues was examined via histological analyses on the paraffin-embedded sections of H&E staining and immunohistological staining for iNOS for subcutaneous tissue as well as heart, liver, and spleen. In vivo stability of the implanted nanosatellite-substrate complex was examined using SEM imaging.

22. Statistical Analysis

All of the experiments conducted in the present invention were repeated independently at least twice. Graphpad Prism 5.00 software or Graphpad Prism 8 software was exploited to perform all statistical treatments of the quantitative results. Different alphabets in the graphs denote statistically significant differences between the compared groups at $p<0.05$. Two groups were compared via statistical assessments with two-tailed Student's t-tests.

Multiple groups were compared via statistical assessments with one-way analysis of variance (ANOVA) and Tukey-Kramer post-hoc tests.

Experimental Example 1

Modulation of Only Density

In Example 1, nanosatellite-substrate complexes were prepared by varying the density of gold nanoparticles on the surfaces of magnetic nanoparticles, and the properties thereof were analyzed.

1. Analysis of Magnetic Nanoparticles

Figure 4:
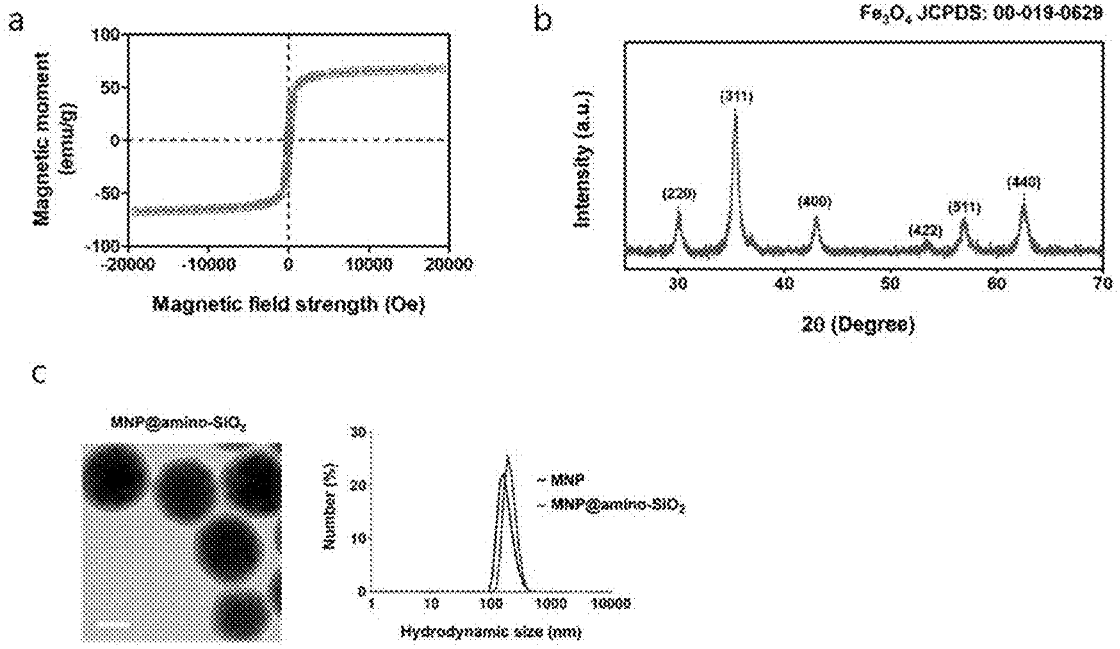
FIG. 4 shows the results of analyzing magnetic nanoparticles in a process of preparing a nanosatellite-substrate complex by modulating only the density of gold nanoparticles.

First, magnetic nanoparticles were synthesized and the properties thereof were evaluated. FIG. 4 shows the results of analyzing the reversible magnetic properties (a), XRD spectra (b), and TEM images and the resulting hydrodynamic sizes (c) of the magnetic nanoparticles. Vibrating sample magnetometry measurement confirmed the reversible magnetic properties of the magnetic nanoparticles with high saturation magnetization (MS) of 67.5 emu/g (FIG. 4*a*). FIG. 4*b*, the diffraction peaks of (220), (311), (400), (422), (511), and (440) planes appeared, which correspond to the reference data of crystalline $Fe_3O_4$ phase. Transmission electron microscopy (TEM) image in FIG. 4*c* showed the uniform coating of the iron oxide core with the amino-silica shell. Dynamic light scattering (DLS) analysis based on the TEM image confirmed that the hydrodynamic size of the iron oxide core was measured to be 179±13 nm and increased to 210±19 nm by coating with the silica shell. The scale bar is 100 nm.

2. Analysis of Gold Nanoparticles

Figure 5:
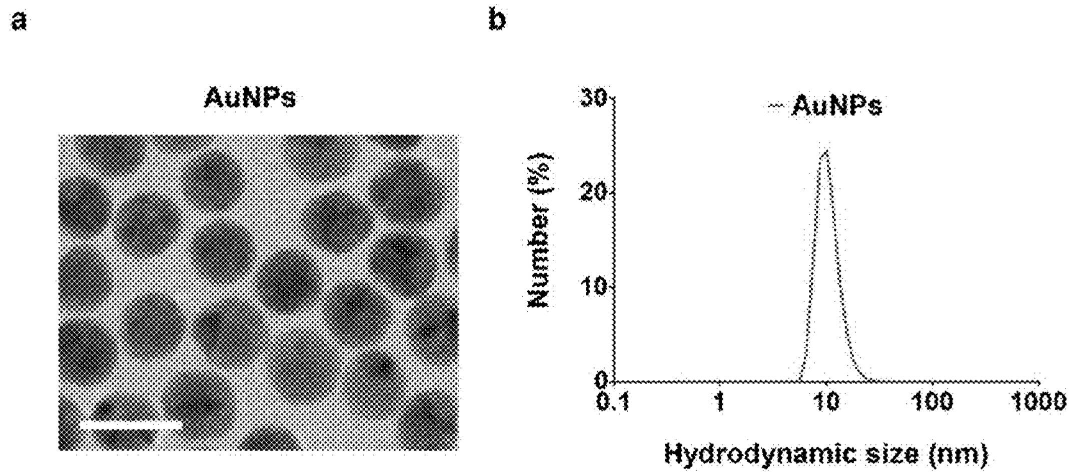
FIG. 5 shows the results of analyzing magnetic nanoparticles in a process of preparing a nanosatellite-substrate complex by modulating only the density of gold nanoparticles.

Next, gold nanoparticles were provided on the surfaces of the magnetic nanoparticles. Here, the average diameter of the gold nanoparticles was kept constant. From the TEM image and DLS analysis of FIG. 5, it can be confirmed that the diameter of the gold nanoparticles formed was almost uniform. In addition, it can be confirmed that the hydrodynamic size of the gold nanoparticles was measured to be 12.5 nm±0.6 nm, which is much smaller than that of the magnetic nanoparticles. The scale bar is 20 nm.

3. Analysis of Gold Nanoparticles Conjugated to Magnetic Nanoparticles

Figure 6:
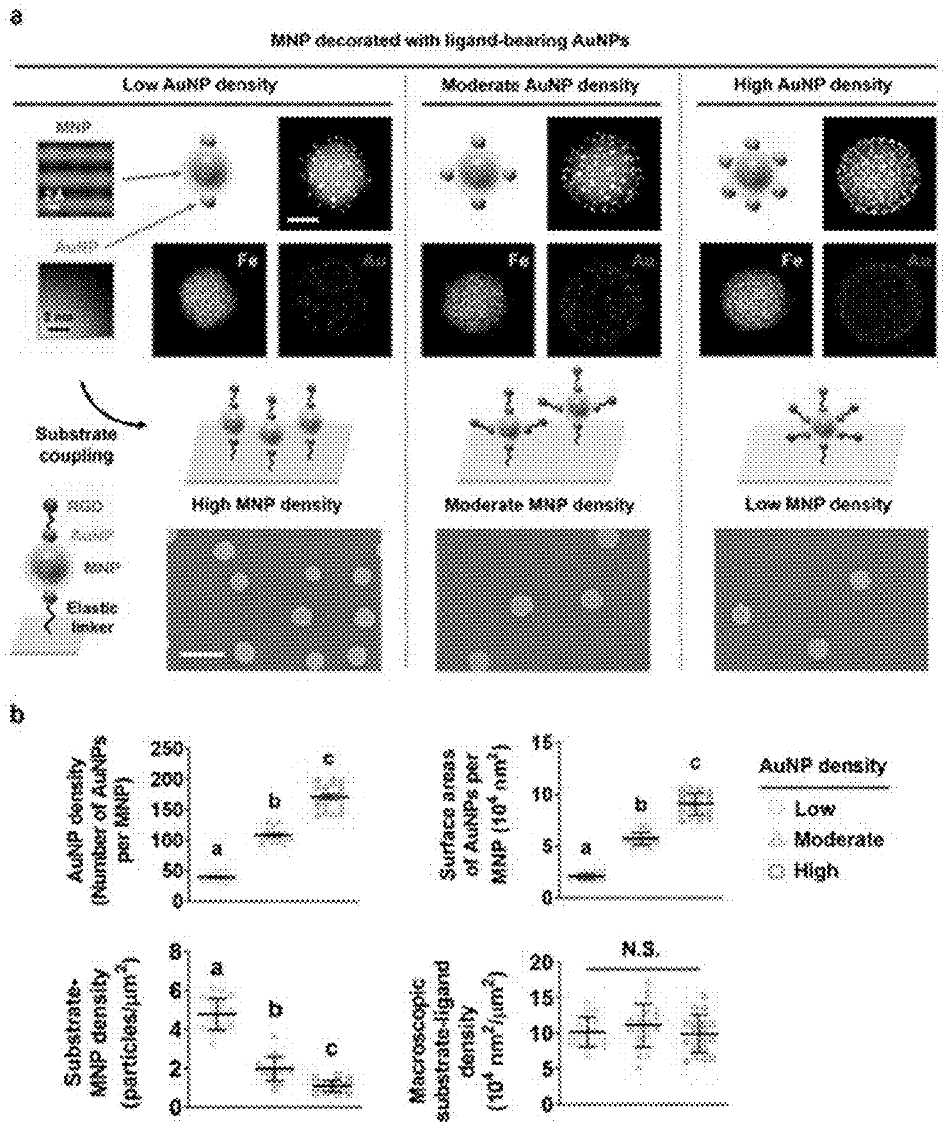
FIG. 6 shows the results of analyzing nanosatellite structures, obtained by conjugating gold nanoparticles to the surfaces of magnetic nanoparticles, and nanosatellite-substrate complexes, in a process of preparing the nanosatellite-substrate complexes by modulating only the density of gold nanoparticles.

FIG. 6 shows the results obtained by providing the gold nanoparticles on the surfaces of the magnetic nanoparticles at varying densities (Low, Medium, and High), and then forming nanosatellite-substrate complexes and analyzing the characteristics thereof. The HAADF-STEM image in FIG. 6A is an image showing that gold nanoparticles (brighter portion) were provided on the magnetic nanoparticles (darker portion) at different densities, and the density difference between the gold nanoparticles was clearly distinguished. In addition, the HR-STEM image of the nanosatellite-substrate complexes shows that the nanosatellite structures having different gold nanoparticle densities were conjugated to the substrates at different densities. In addition, the presence and location of each of Fe and Au elements can be found in the EDS mapping.

FIG. 6*b* depicts graphs the results of quantification of the images. The numbers of gold nanoparticles per each magnetic nanoparticle (densities of gold nanoparticles) In the Low AuNP density, Medium AuNP density and High AuNP density groups were calculated to be 39±6, 108±11, and 171±24, respectively. In addition, the total surface areas of gold nanoparticles per magnetic nanoparticle in the groups were calculated to be 20919±3064, 57447±5988, and 90789±12530 $nm^2$, respectively. In addition, based on the SEM images in FIG. 6*a* (scale bar: 500 nm), the densities of the nanosatellite structures on the substrates in the groups were calculated to be 5.2±0.3, 2.1±0.1, and 1.1±0.1 particles/$\mu m^2$, respectively. In addition, the total surface areas of gold nanoparticles per magnetic nanoparticle were calculated to be 20919±3064, 57447±5988, and 90789±12530 $nm^2$, respectively. Since the gold nanoparticles were subsequently coated with the ligand, the product of the magnetic nanoparticle density and the total surface area of the gold nanoparticles per magnetic nanoparticle yielded surface ligand density, which remained similar (103,000 to 122,000 $nm^2/\mu m^2$) among the groups. The nanosatellite structure density calculated here was optimal in the regulation of macrophage adhesion and polarization. Data are expressed as mean±standard deviation (n=20).

4. Analysis of Nanosatellite Structures

Figure 7:
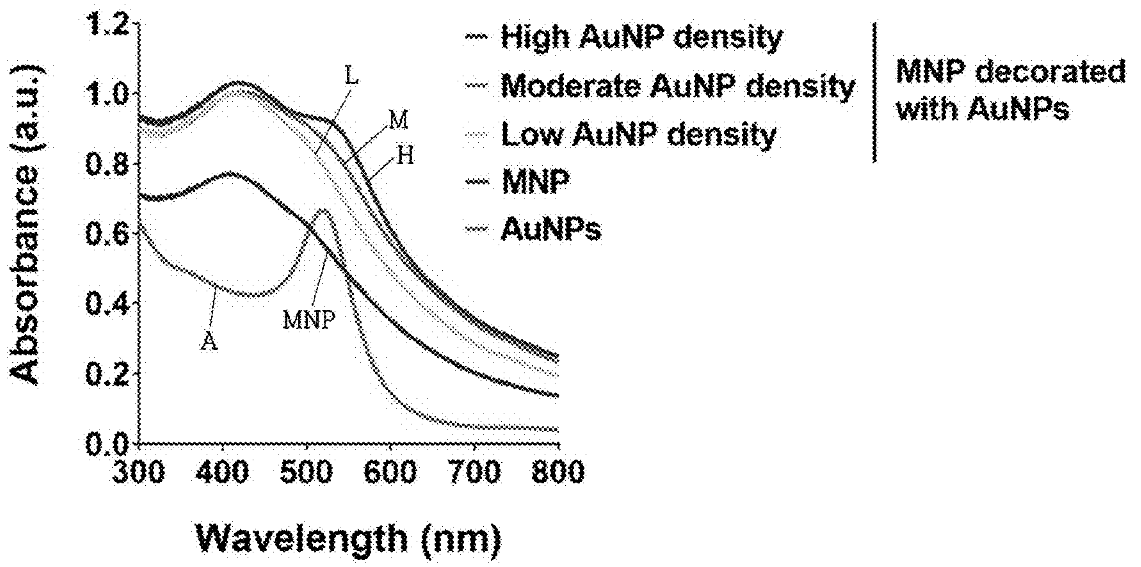
FIGS. 7 to 9 show the results of analyzing nanosatellite-substrate complexes in a process of preparing the nanosatellite-substrate complexes by modulating only the density of gold nanoparticles.

FIG. 7 shows UV-Vis absorption spectra of magnetic nanoparticles, gold nanoparticles, and gold nanoparticles conjugated to magnetic nanoparticles at different densities. The UV-Vis absorption spectra showed the absorption peaks at 520 nm and 408 nm, corresponding to the gold nanoparticles and magnetic nanoparticles alone, respectively. However, the absorption peaks of the gold nanoparticles conjugated to the magnetic nanoparticles overlapped with those of both the gold nanoparticles alone and magnetic nanoparticles alone, which exhibited increasing peak intensities with increasing gold nanoparticles densities.

Figure 8:
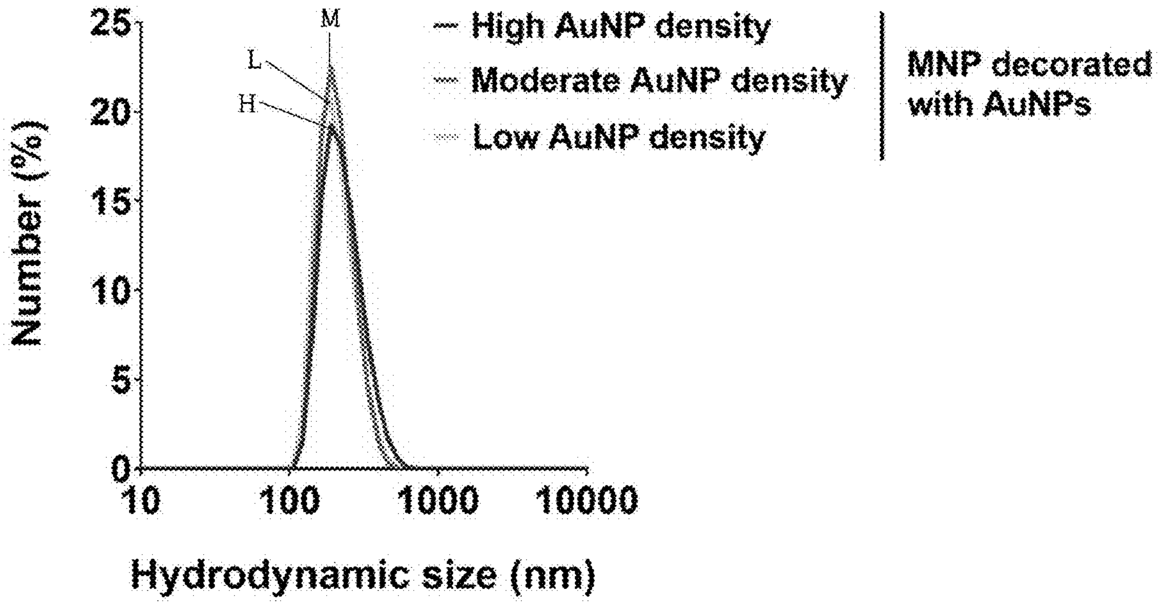

FIG. 8 shows the hydrodynamic size of each group, and revealed that all of the gold nanoparticles conjugated to the magnetic nanoparticles at various gold nanoparticle densities exhibited similar sizes with no significant differences.

Figure 9:
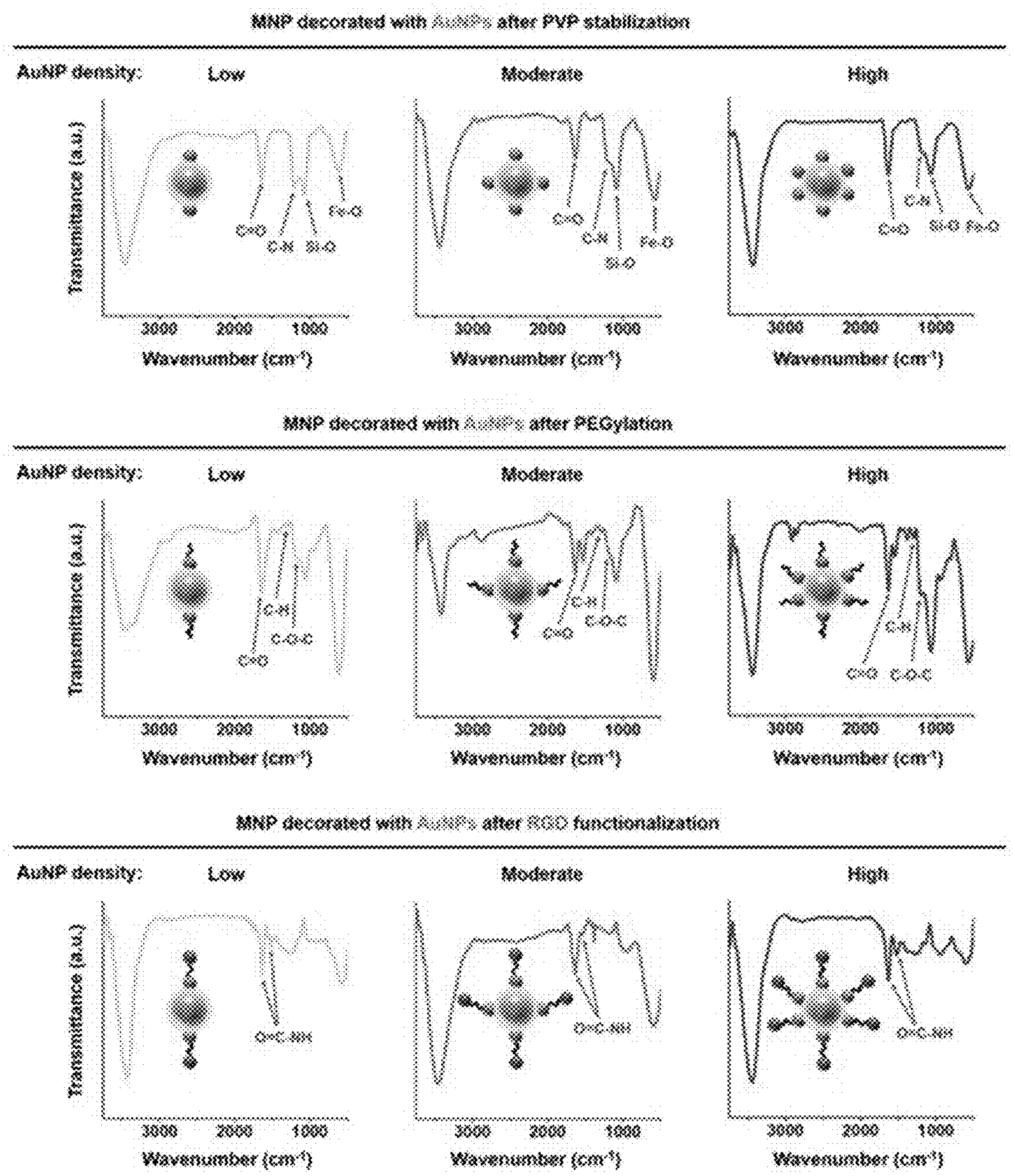

FIG. 9 shows the results of measuring FTIR for each of the steps of sequentially conjugating the gold nanoparticles, the polymer linker and the ligand to the magnetic nanoparticles. After PVP stabilization of the gold nanoparticles conjugated to the magnetic nanoparticles, C—N bond peaks at 1230 $cm^{-1}$ appeared, and after PEGylation following conjugation of the polymer linker, C—O—C bond peaks at 1150 $cm^{-1}$ appeared, and RGD coupling, peaks at 1632 $cm^{-1}$ (amide I) and 1535 $cm^{-1}$ (amide II) appeared. However, there was no difference in FTIR between the gold nanoparticle densities.

Figure 10:
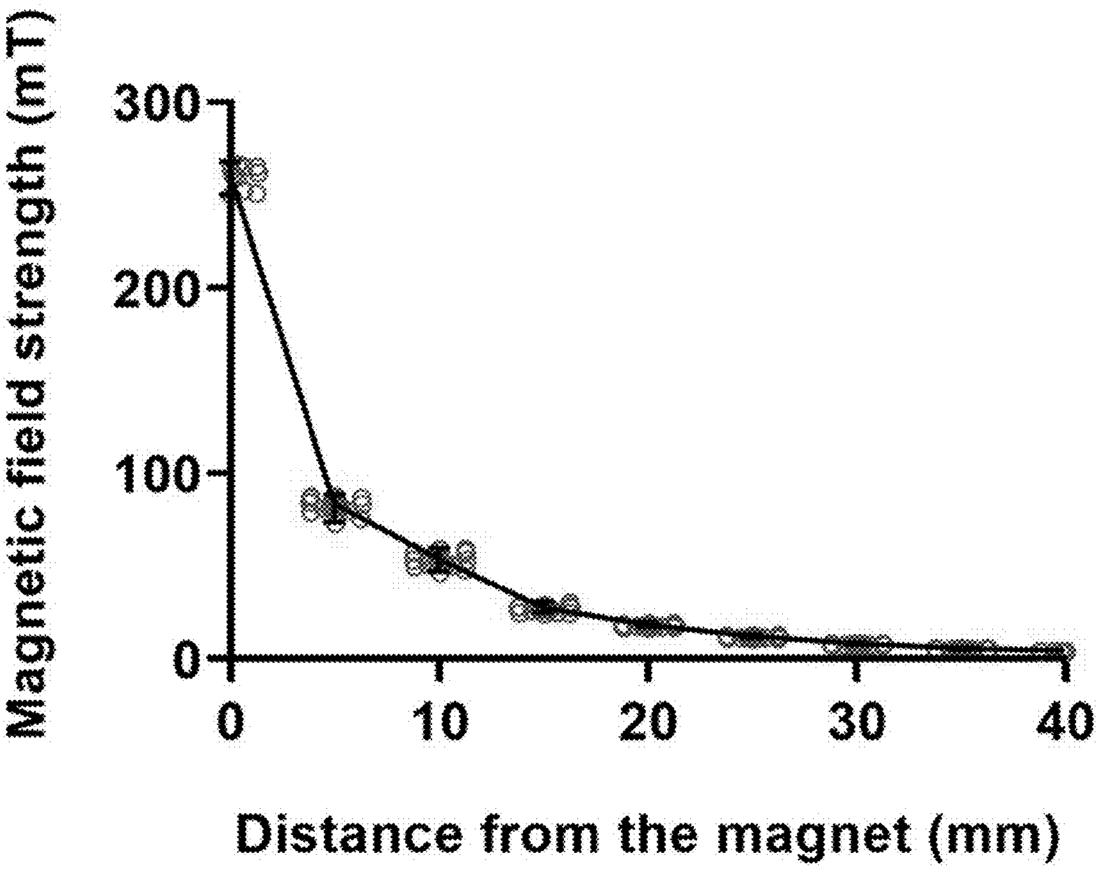
FIGS. 10 to 12 show the results of observing nanosatellite-substrate complex changes resulting from the application of a magnetic field to a nanosatellite-substrate complex prepared by modulating only the density of gold nanoparticles.
Figure 11:
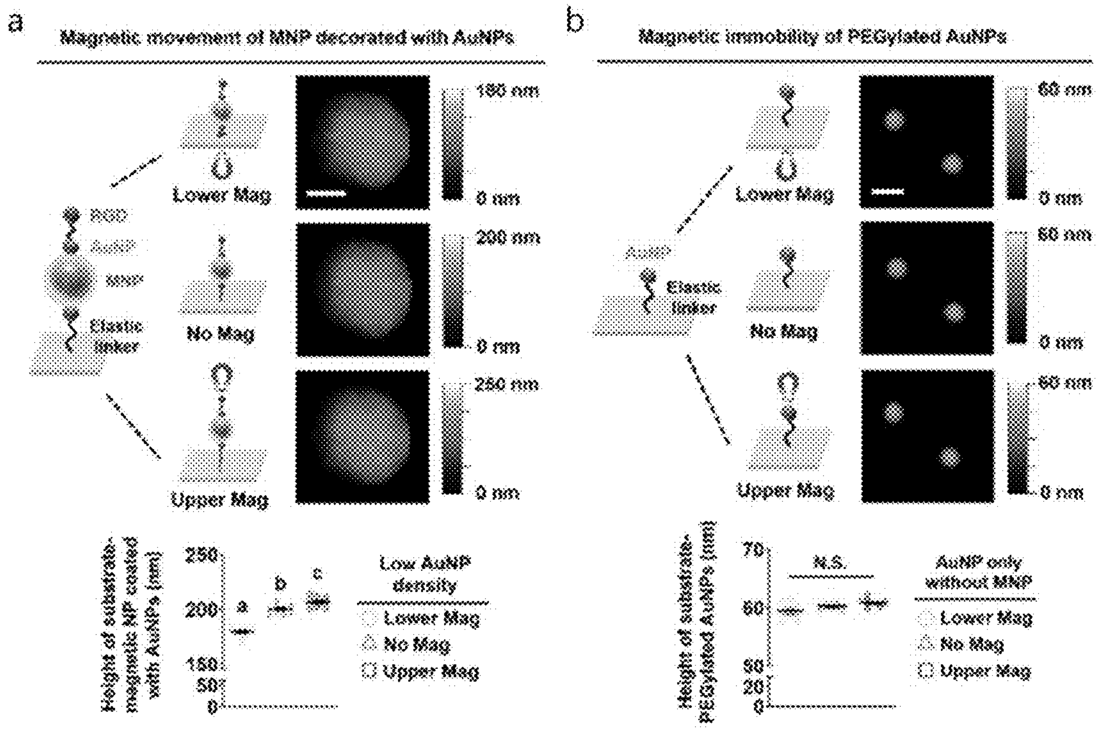
Figure 12:
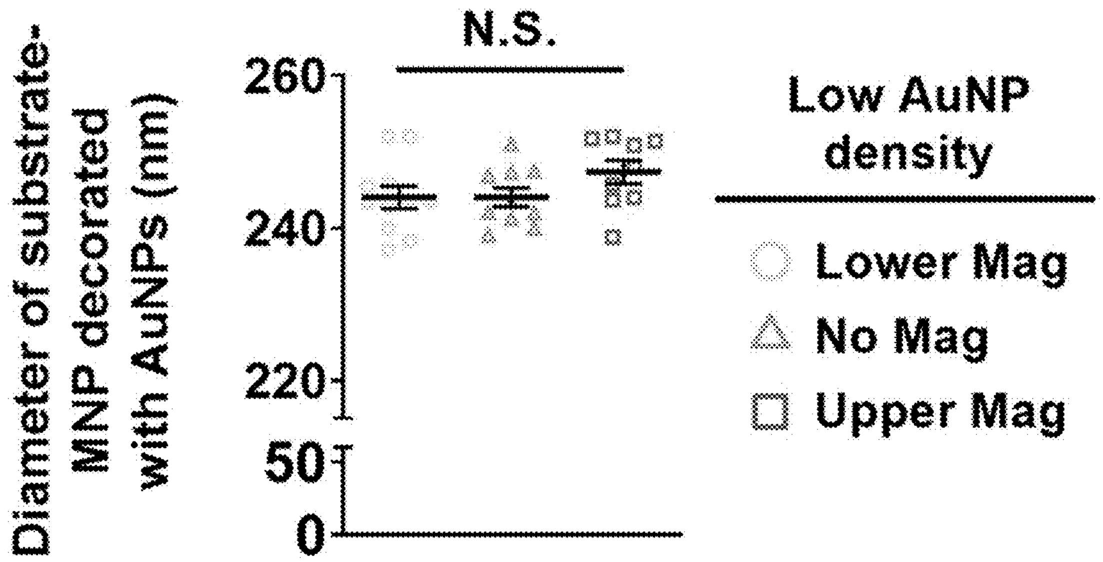

5. Switching of Movement of Nanosatellite Structure by Application of Magnetic Field The vertical movement of the nanosatellite structure by applying of a magnetic field to the nanosatellite-substrate complex was analyzed, and the results are shown in FIGS. 10 to 12. FIG. 10 shows the magnetic field strength as a function of distance from a permanent magnet (270 mT) used.

FIG. 11 shows AFM images in the Lower Mag, No Mag, and Upper Mag conditions, respectively, and the height change for each condition was quantified. The heights of the nanosatellite structures in the groups were 180.0±2.0, 195.7±4.9, and 212.3±1.5 nm in order, which means that the nanosatellite structures were moved vertically by the application of the magnetic field. Since the polymer linker (5 kDa) used in this experiment was elastic, a height difference of 32 nm (between 180 nm and 212 nm) appeared to be significant to modulate the degree of cells sensing the substrate to markedly alter macrophage adhesion. However, in the case in which there were only gold nanoparticles without magnetic nanoparticles (FIG. 11*b*), there was little difference in height even when the magnetic field was applied. In addition, the diameter of the nanosatellite structure was kept almost constant at 243 to 246 nm regardless of whether the magnetic field was applied (FIG. 12). Therefore, it can be confirmed that, due to the magnetic nanoparticles, vertical movement of the nanosatellite structure was induced by applying a magnetic field to the nanosatellite structure, and the shape of the magnetic nanoparticles was stably maintained even when the magnetic field was applied.

Experimental Example 2

Modulation of Diameter of and Distance Between Gold Nanoparticles

Nanosatellite-substrate complexes were prepared by varying the diameter of the gold nanoparticles conjugated to the magnetic nanoparticles and the distance between adjacent gold nanoparticles (Examples 2 to 4).

1. Analysis of Magnetic Nanoparticles

Figure 13:
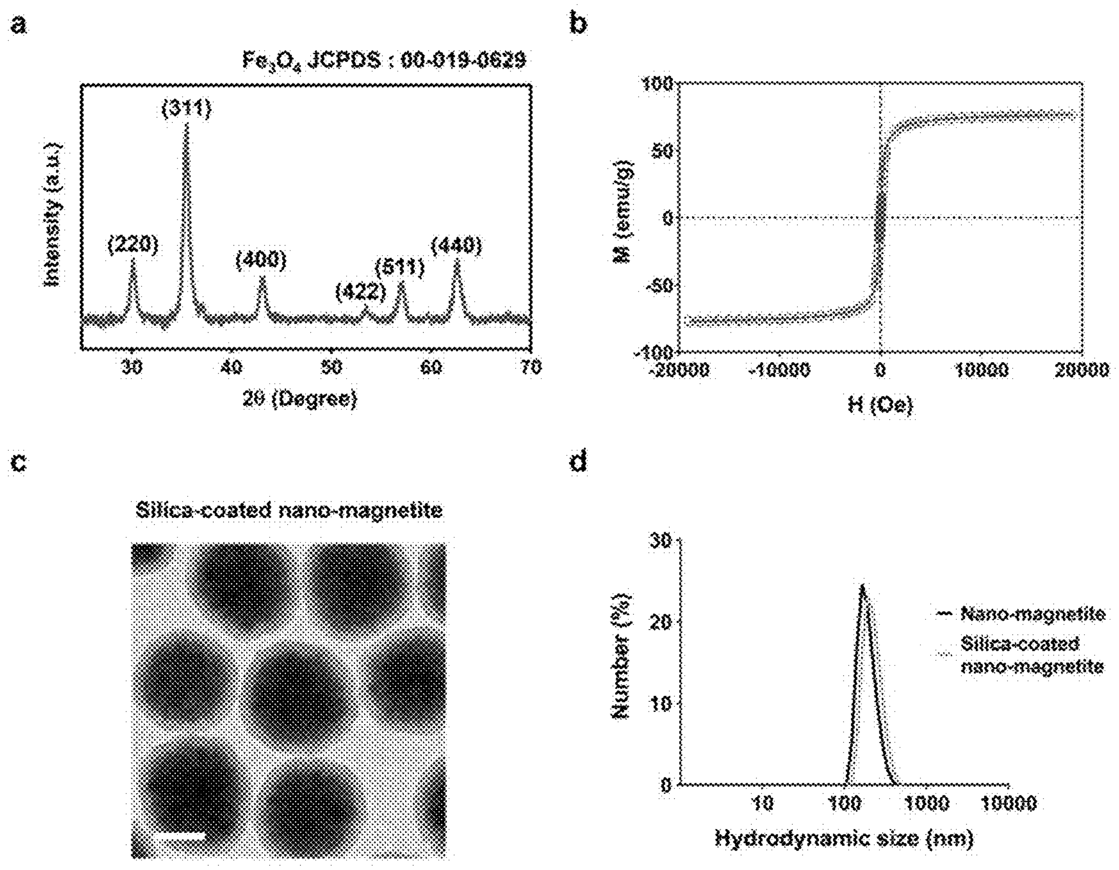
FIG. 13 shows the results of analyzing magnetic nanoparticles in a process of preparing a nanosatellite-substrate complex by modulating the diameter of gold nanoparticles and the distance between adjacent gold nanoparticles.

FIG. 13 shows the results of analyzing the characteristics of magnetic nanoparticles.

From the XRD results in FIG. 13*a*, it can be confirmed that peaks corresponding to the crystalline phase of $Fe_3O_4$ appeared, indicating the presence of iron oxide in the magnetic nanoparticles.

From the VSM results in FIG. 13*b*, it can be confirmed that the magnetic nanoparticles exhibited negligible coercivity with overlapping hysteresis loops and high saturation magnetization (MS) of 76.5 emu/g, indicating that the magnetic nanoparticles have reversible magnetization.

From FIG. 13*c*, it can be confirmed that the magnetic nanoparticles were formed to have an almost uniform size. In addition, from the DLS results in FIG. 13*d*, it can be confirmed that the size of the iron oxide core was increased from 190±4.8 nm to 222±5.7 nm after coating the silica shell.

2. Analysis of Gold Nanoparticles

Gold nanoparticles with various diameters were prepared using a seed-mediated growth method. First, the present inventors synthesized gold nanoparticles with diameters of 3 and 13 nm by tuning the $Au^{3+}$ precursor concentration and reducing agents.

Figure 14:
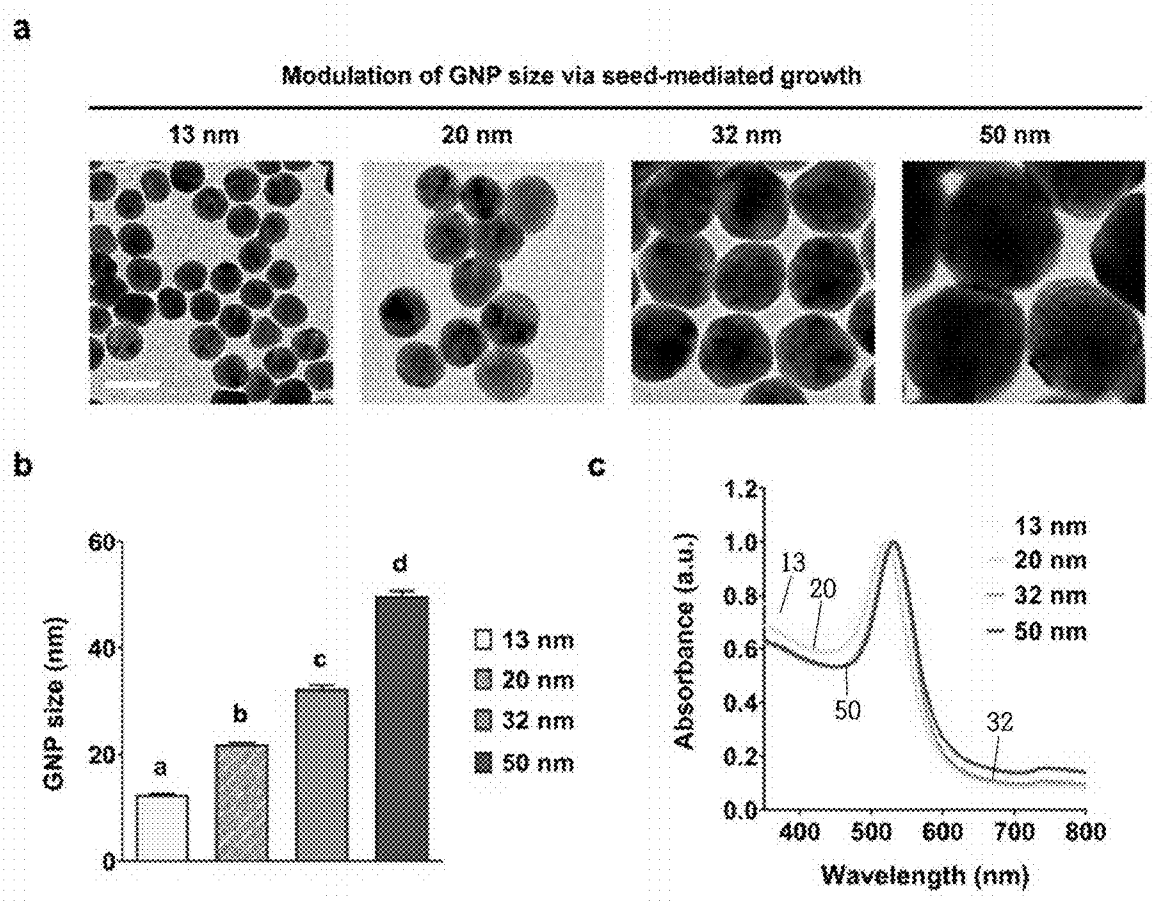
FIG. 14 shows TEM images and UV-Vis absorption peaks for gold nanoparticles with various diameters were prepared using a seed-mediated growth method.

Gold nanoparticles having sizes of 20, 32 and 50 nm were grown using gold seed particles having a diameter of 13 nm, and FIG. 14 shows TEM images and UV-Vis absorption peaks for these gold nanoparticles. FIG. 14 shows analogous UV-Vis absorption peaks around 520 nm regardless of the size of each gold nanoparticle.

Figure 15:
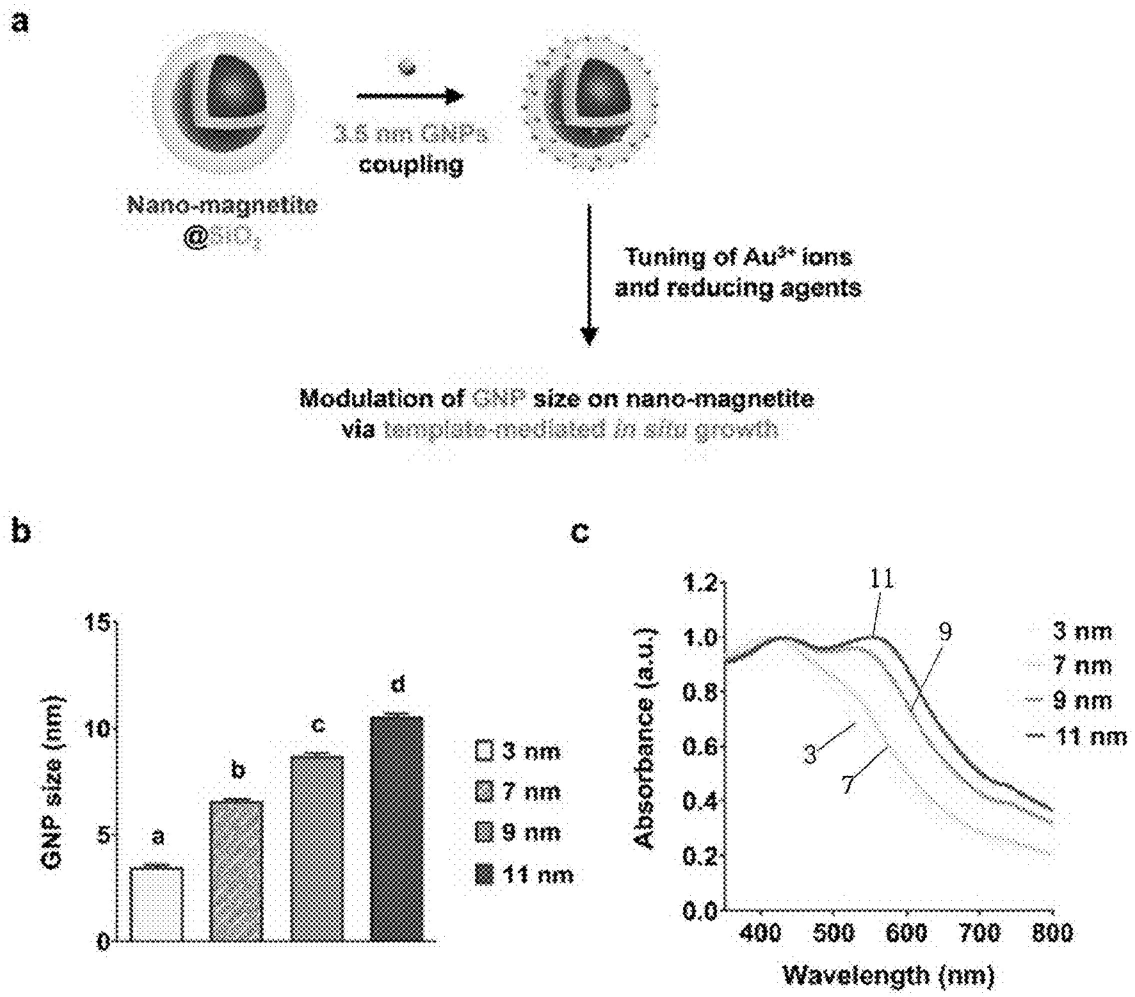
FIG. 15 shows magnetic nanoparticles grown into 7, 9 and 11 nm sizes after conjugation of gold seed particles having a diameter of 3 nm by inducing in situ growth.

In addition, after conjugation of gold seed particles having a diameter of 3 nm to magnetic nanoparticles, the gold seed particles were grown into 7, 9 and 11 nm sizes by inducing in situ growth, and the results are shown in FIG. 15. Since gold nanoparticles have a Debye length of 2.5 to 3 nm, the distance between adjacent gold nanoparticles should be at least 5 to 6 nm. Thus, in a method of conjugating gold nanoparticles directly to magnetic nanoparticles, it is not possible to achieve a spacing similar to the sub-molecule-level diameter of fibronectin (FN). Therefore, gold nanoparticles were synthesized by adjusting the distance between adjacent gold seed particles to be greater than or equal to the Debye length, and then modulating the $Au^{3+}$ concentration and citrate to $Au^{3+}$ ratio. In order to prevent self-nucleation of gold, a small amount of $Au^{3+}$ was repeatedly supplied to gradually grow gold seed particles. As a result, the distance between adjacent gold nanoparticles formed was less than or equal to the Debye length. UV-Vis absorbance spectra (FIG. 15*c*) exhibited red shits in the absorption peaks with increasing sizes of the gold nanoparticles.

3. Analysis of Gold Nanoparticles Conjugated to Surface of Magnetic Nanoparticle Gold nanoparticles were provided on the surfaces of magnetic nanoparticles by varying the diameter of the gold nanoparticles and the distance between adjacent gold nanoparticles. They were divided into three groups: 7-3 (nm), 13-17 (nm) and 20-20 (nm). In particular, the 20-20 (nm) group was prepared to provide binding sites for multiple integrin molecules in contrast with the other groups that can accommodate only a single integrin.

Figure 16:
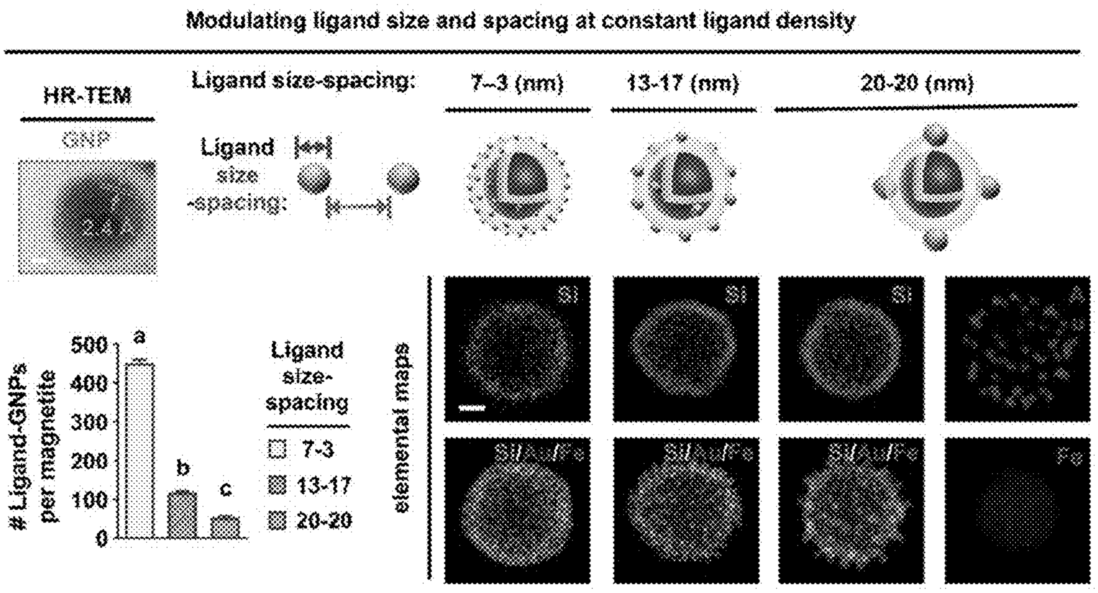
FIGS. 16 to 21 show the results of analysis performed after conjugation of nanoparticles to the surfaces of magnetic nanoparticles in a process of preparing nanosatellite-substrate complexes by modulating the diameter of gold nanoparticles and the distance between adjacent gold nanoparticles.

FIG. 16 shows the results of identifying the elements gold, silicon, and iron in each group. HR-TEM atomic-scale image confirmed the crystalline gold nanoparticles exhibiting periodic lattice spacing, and the average grid spacing was found to be 2.4 Å. The numbers of gold nanoparticles per magnetic nanoparticle in the groups were calculated to be 452.0±8.3, 118.4±3.1, and 51.8±4.1, respectively.

Figure 17:
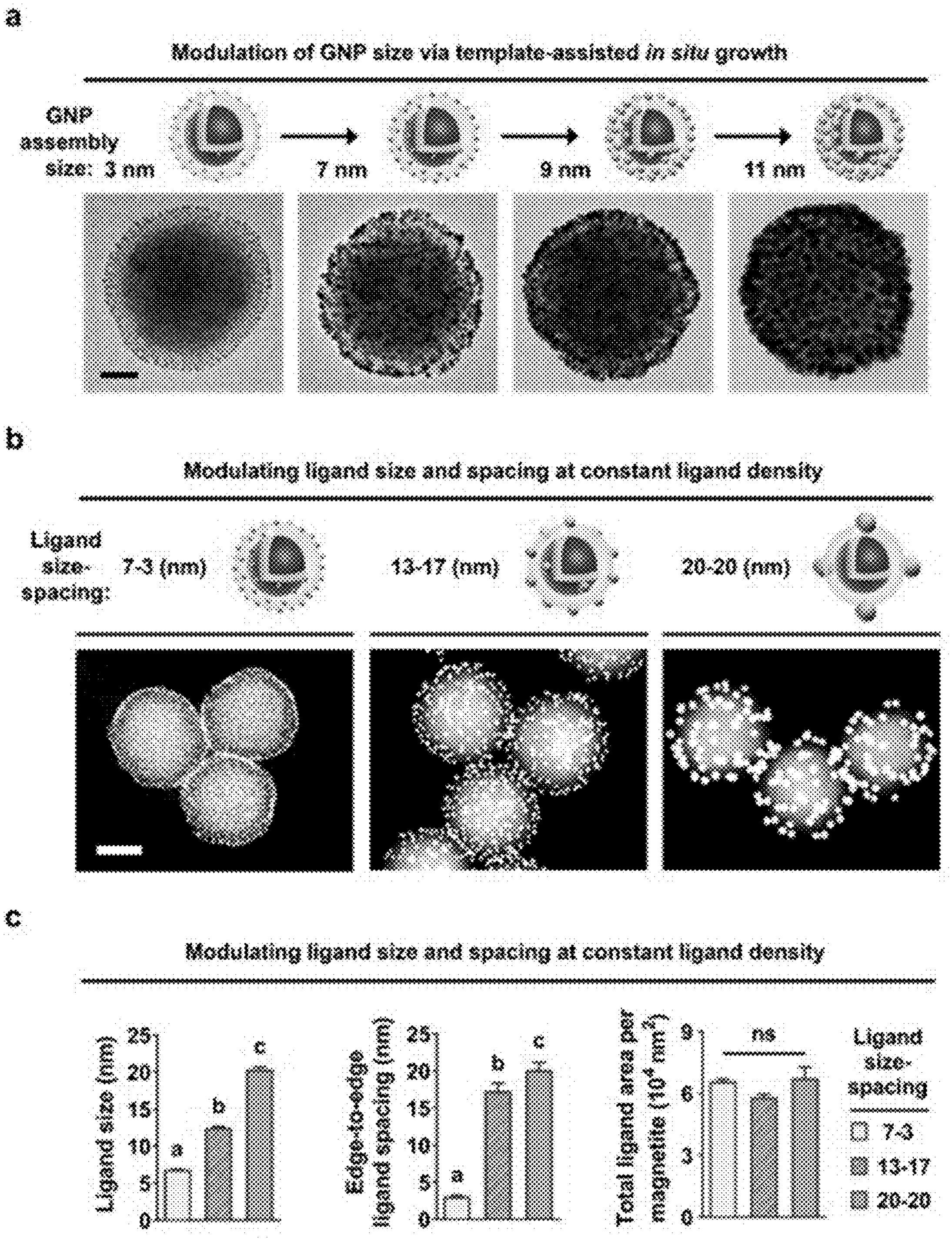

FIG. 17 shows the results of analyzing the size and density of gold nanoparticles.

The average diameters of gold nanoparticles were measured to be 6.7±0.1 nm in the "7-3" group, 12.5±0.2 nm in the "13-17" group, and 20.3±0.3 nm in the "20-20" group. In addition, HAADF images show the edge-to-edge spacing of adjacent gold nanoparticles, which was measured to be 2.8±0.2 nm in the "7-3" group, and 17.3±1.0 nm in the "13-17" group, and 20.1±1.0 nm in the "20-20" group. In addition, the total area of gold nanoparticles per magnetic nanoparticle was calculated to be 58,119 to 67,533 $nm^2$ in the groups without statistically significant differences.

Thus, three groups were prepared in which the overall ligand density was constant while the diameter of gold nanoparticles and the distance between adjacent gold nanoparticles were modulated.

Figure 18:
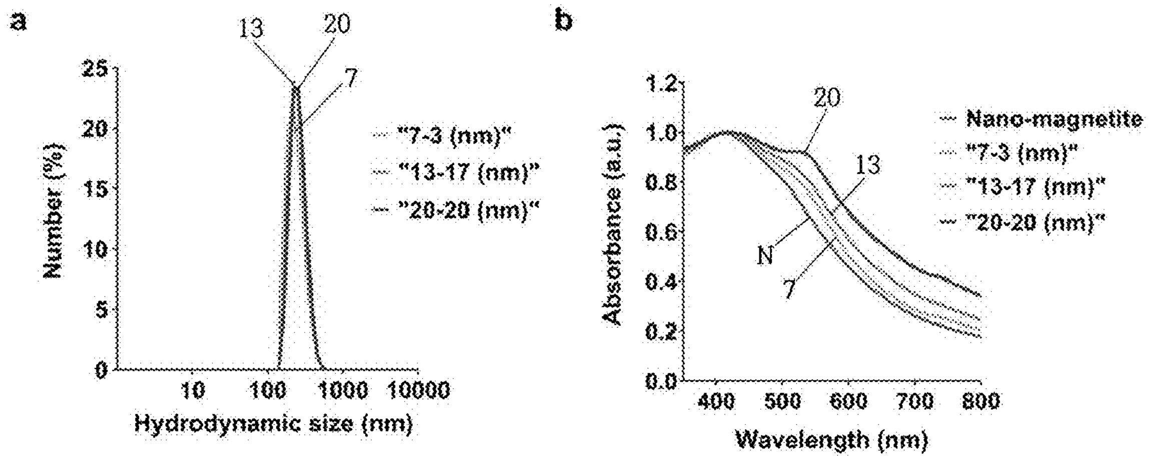
Figure 19:
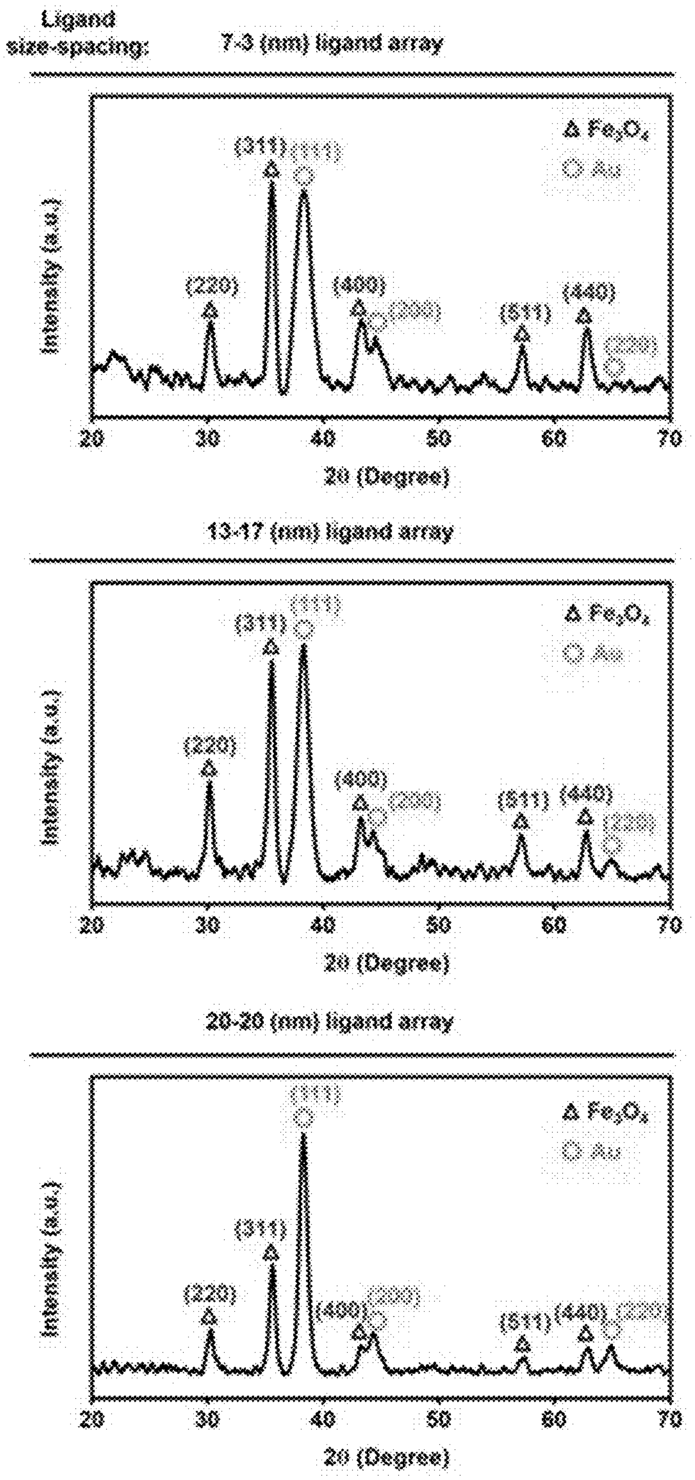
Figure 20:
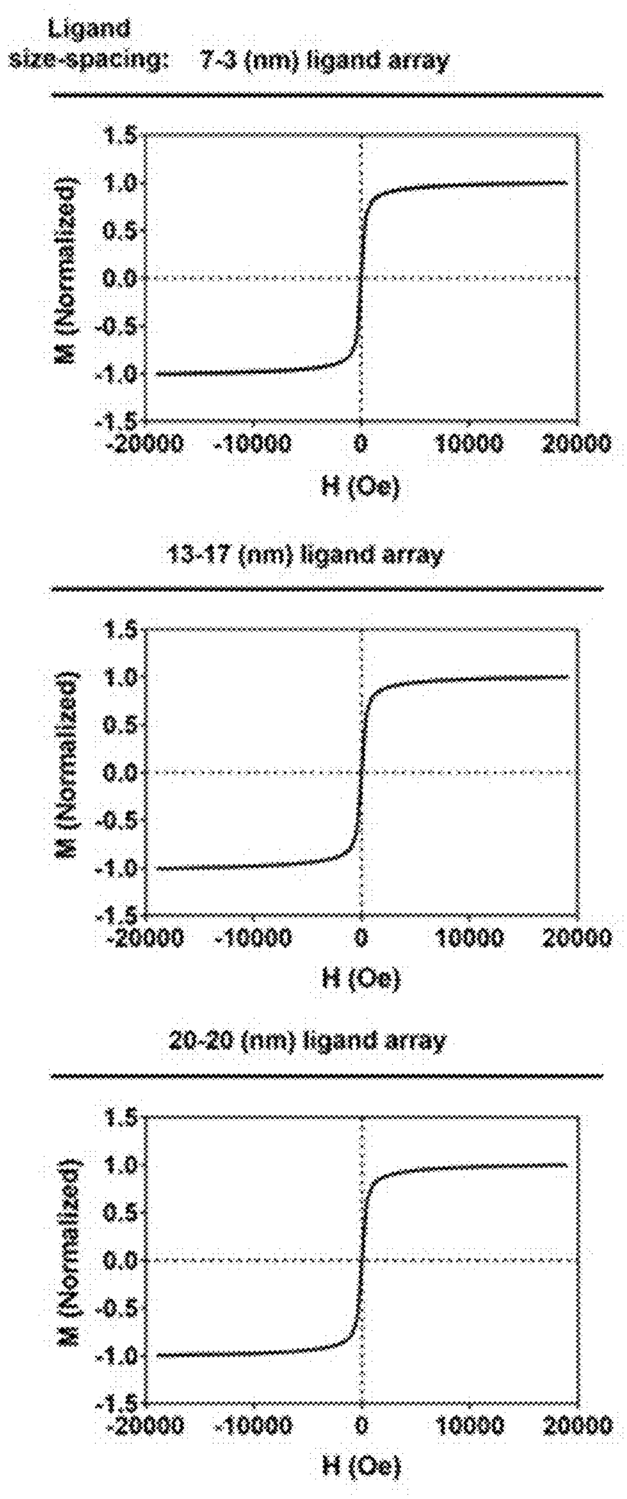

FIGS. 18 to 20 show the results of analyzing the characteristics of each group.

In FIG. 18, it can be confirmed that the hydrodynamic sizes of the three groups are almost similar at 238 to 260 nm, and UV-Vis absorbance spectra of the three groups confirmed that they retained both the gold nanoparticles (absorption peaks at 520 nm) and the magnetic nanoparticles (absorption peaks at 408 nm). Furthermore, XRD patterns in FIG. 19 show peaks corresponding to both the crystalline $Fe_3O_4$ and Au phases. VSM measurements in FIG. 20 confirmed that these three groups showed reversible magnetism.

Figure 21:
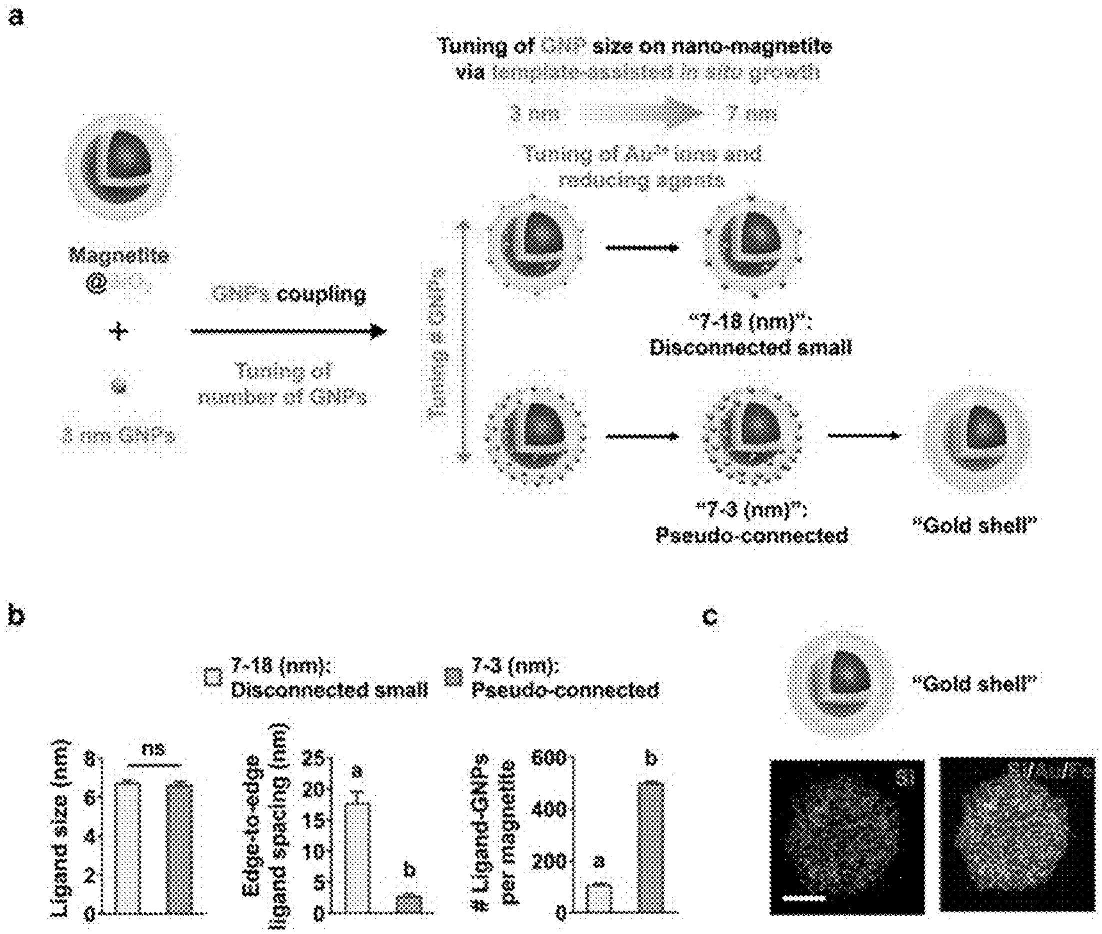

FIG. 21 shows that gold nanoparticles having a diameter of 7 nm were prepared by varying the distance between adjacent gold nanoparticles. As the distance between adjacent gold nanoparticles varied, the relationship between the gold nanoparticles changed: Disconnected ("7-18" group), Pseudo-connected ("7-3" group), and connected (gold shell group).

4. Analysis of Nanosatellite-Substrate Complexes

A polymer linker, a ligand, and a substrate were further conjugated to each of the above groups, thus preparing nanosatellite-substrate complexes.

Figure 22:
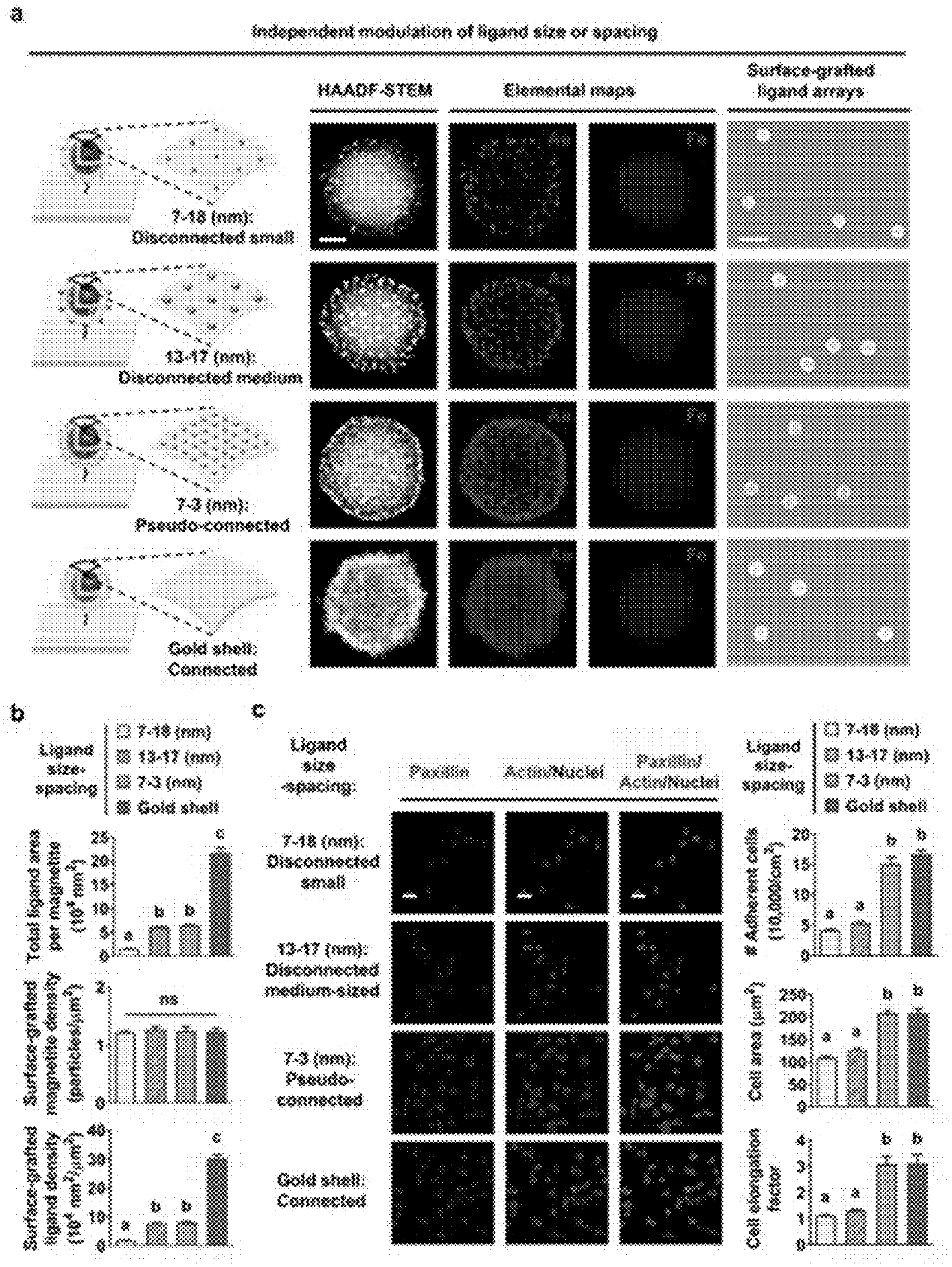
FIG. 22 shows the results of analyzing nanosatellite-substrate complexes prepared by modulating the diameter of gold nanoparticles and the distance between adjacent gold nanoparticles.

FIG. 22 shows the characteristics of each nanosatellite-substrate complex group. The HAADF-STEM images and the corresponding element maps indicate the presence of Fe and Au elements. Also, it can be seen that, in the "7-18" group and the "13-17" group, the diameter of gold nanoparticles increased, but the density of the nanosatellite structures on the substrate was similar between the groups. In addition, it can be seen that the density of the nanosatellite structures on the substrate was similar between the "7-3" group and the gold shell group. The graphs quantifying this density were obtained by multiplying the total area of gold nanoparticles per magnetic nanoparticle by the number of magnetic nanoparticles per unit area, and the calculated gold nanoparticle densities were $1.85\times10^4\pm0.01\times10^4$ $nm^2/\mu m^2$ ("7-18" group), $7.69\times10^4\pm0.35\times10^4$ $nm^2/\mu m^2$ ("13-17" group), $8.03\times10^4\pm0.49\times10^4$ $nm^2/\mu m^2$ ("7-3" group), and $30.14\times10^4\pm1.31\times10^4$ $nm^2/\mu m^2$ ("gold shell" group). In particular, the gold nanoparticle density was significantly higher (by 275%) in the "gold shell" group than in the "7-3" group. These findings prove the independent modulation of the diameter of gold nanoparticles and the distance between adjacent gold nanoparticles.

Figure 23:
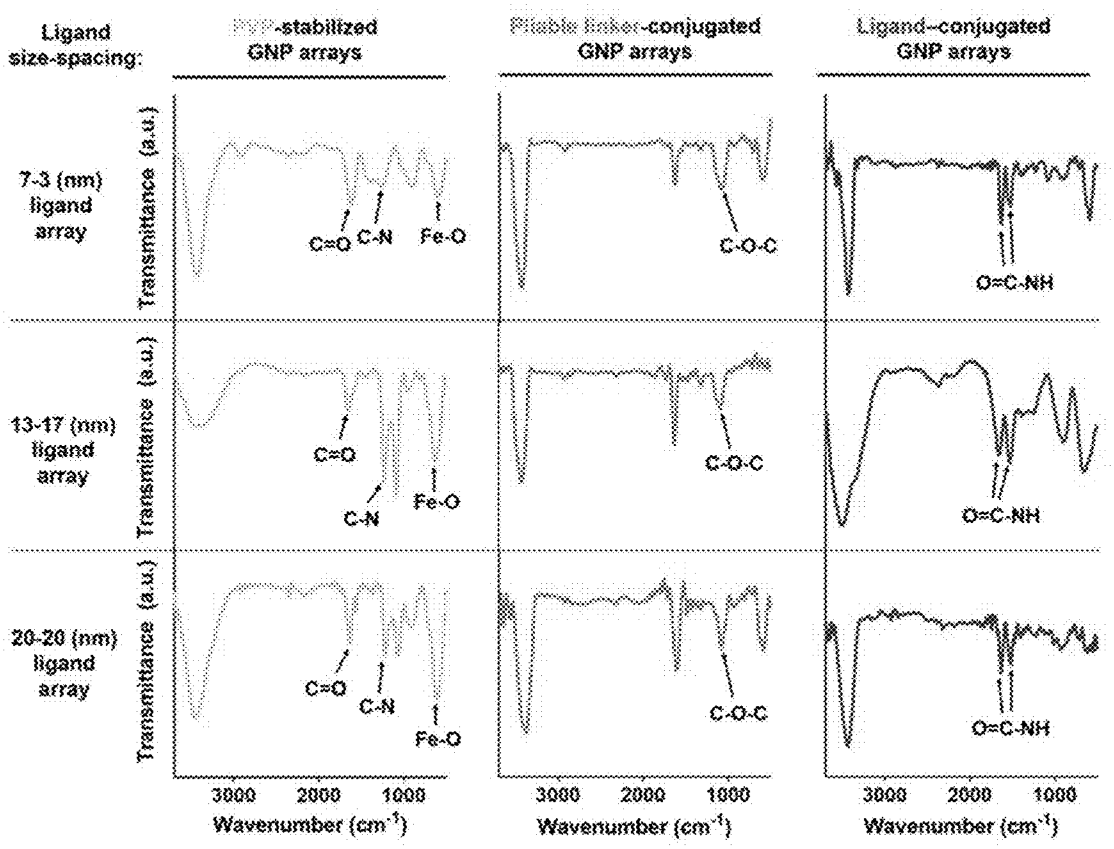
FIG. 23 shows the results of analyzing nanosatellite-substrate complexes prepared by modulating the diameter of gold nanoparticles and the distance between adjacent gold nanoparticles.

FIG. 23 shows the results of measuring FTIR while sequentially performing PVP stabilization, polymer linker conjugation, and ligand conjugation after conjugating gold nanoparticles to magnetic nanoparticles. Absorption peaks observed corresponded to C—N bonds at 1229 $cm^{-1}$ in the PVP stabilization step, C—O—C bonds at 1151 $cm^{-1}$ after polymer linker conjugation, and amide I and II bonds at 1631 $cm^{-1}$ and 1534 $cm^{-1}$, respectively, after ligand conjugation, which are the same as the results in Experimental Example 1.

Experimental Example 3

Experiments were conducted to examine whether the adhesion and polarization of macrophages could be regulated by applying a magnetic field to each nanosatellite-substrate complex.

1. Modulation of Only Density of Gold Nanoparticles

Using mouse macrophages (RAW 264.7), experiments were conducted to examine whether nanosatellite-substrate complexes prepared by varying the density of gold nanoparticles could regulate the adhesion and polarization of macrophages.

(1) Experiment on Macrophage Adhesion

Figure 24:
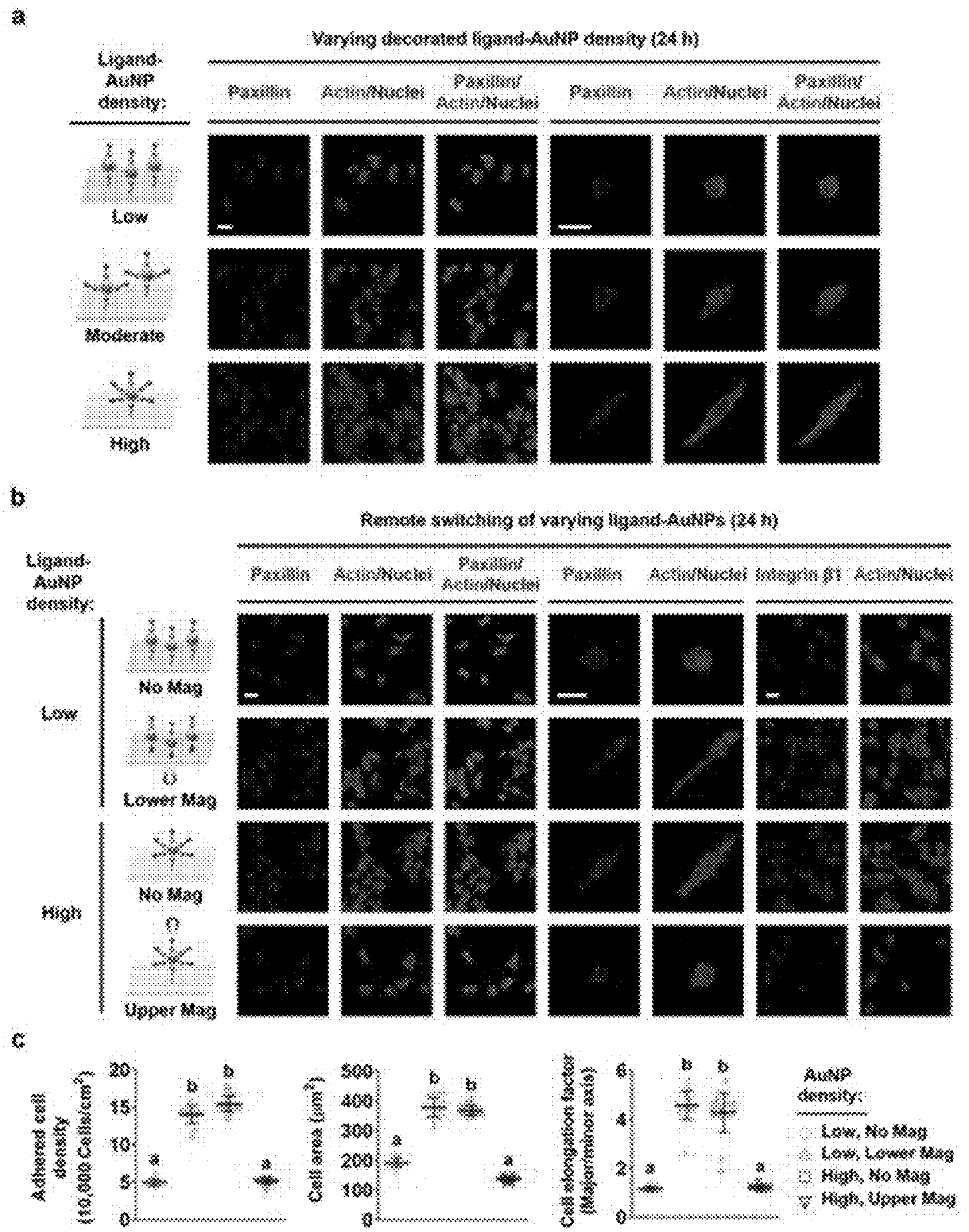
FIGS. 24 to 28 show the results of examining whether macrophages adhere to nanosatellite-substrate complexes prepared by modulating only the density of gold nanoparticles.
Figure 25:
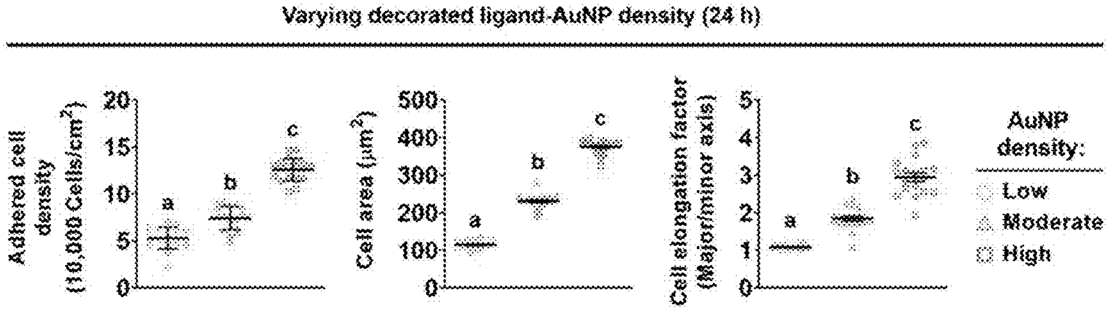
Figure 26:
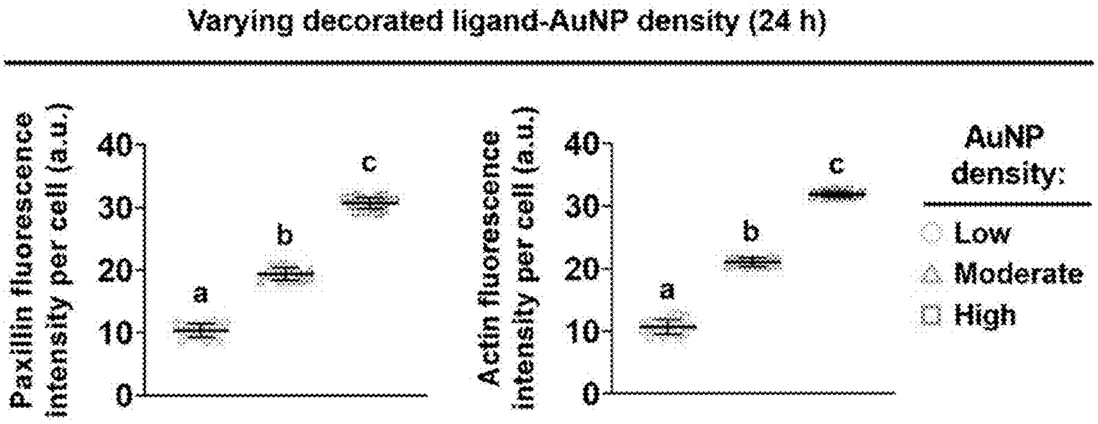

FIG. 24 shows the results of evaluating whether macrophage adhesion occurs well with or without applying a magnetic field to nanosatellite-substrate complexes of different densities. The confocal immunofluorescence images showed that macrophages exhibited more robust adhesion to the nanosatellite-substrate complex with increasing density of the nanoassemblies as revealed by pronounced paxillin expression and pervasive F-actin assembly in elongated morphology. Quantification of the immunofluorescence images further revealed that macrophages adhered to the nanosatellite-substrate complex in higher cell density, spread cell area, cell elongation factor (suggesting elongated spreading of the adherent macrophages), paxillin expression and F-actin assembly with increasing density of the nanoassemblies (FIGS. 25 and 26). These results prove that modulation of only the nanoassembly density without changing macroscopic RGD ligand density can stimulate macrophage adhesion. In FIG. 24, the scale bar is 20 μm, and data are expressed as mean±standard error (n=20).

Figure 27:
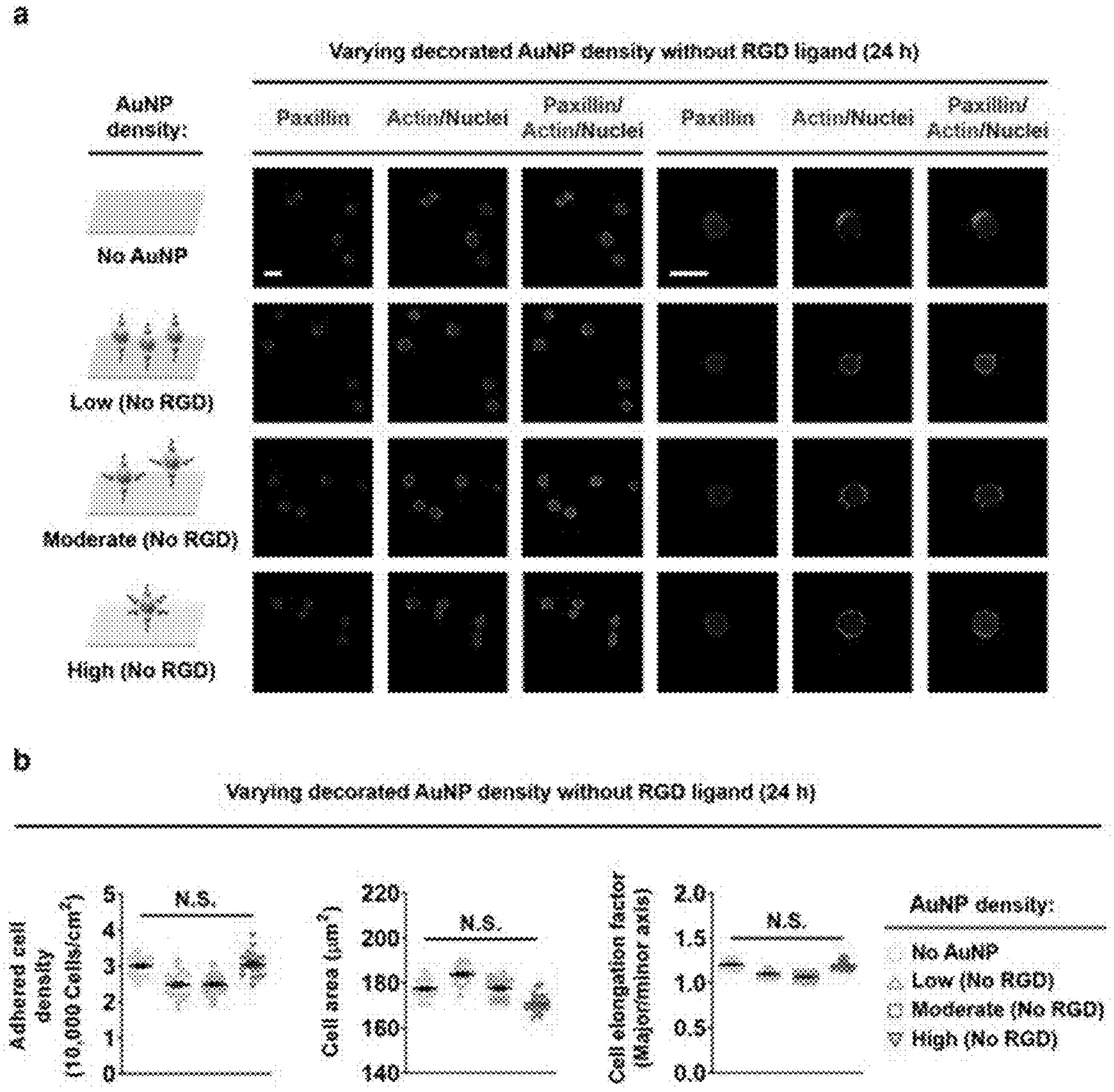
Figure 28:
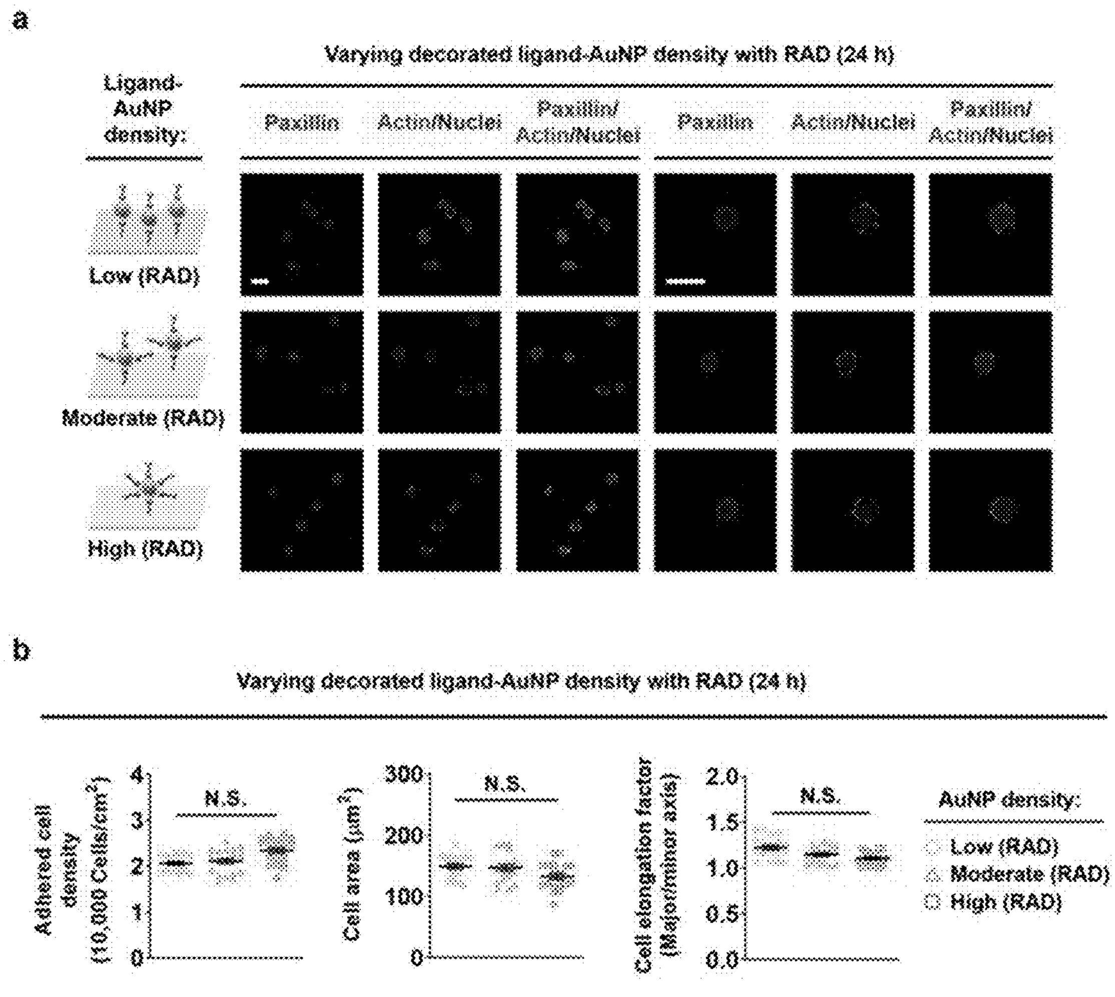

For comparison with these results, experiments were conducted on the case where there was only a substrate, the case where the ligand was absent, and the case of a ligand having a scrambled RAD sequence (hereinafter referred to as RAD ligand) was conjugated instead of the RGD ligand. The results are shown in FIGS. 27 and 28. Confocal immunofluorescence images revealed that macrophages did not readily adhere to the nanosatellite-substrate complex with low adhesion density, low spreading, and round morphology in all groups. This means that the RGD ligand is necessary to regulate the adhesion and polarization of macrophages.

(2) Experiment on Macrophage Adhesion Depending on Direction of Application of Magnetic Field A magnetic field was applied to the nanosatellite-substrate complex in different directions or was not applied, and macrophage adhesion was monitored.

Figure 29:
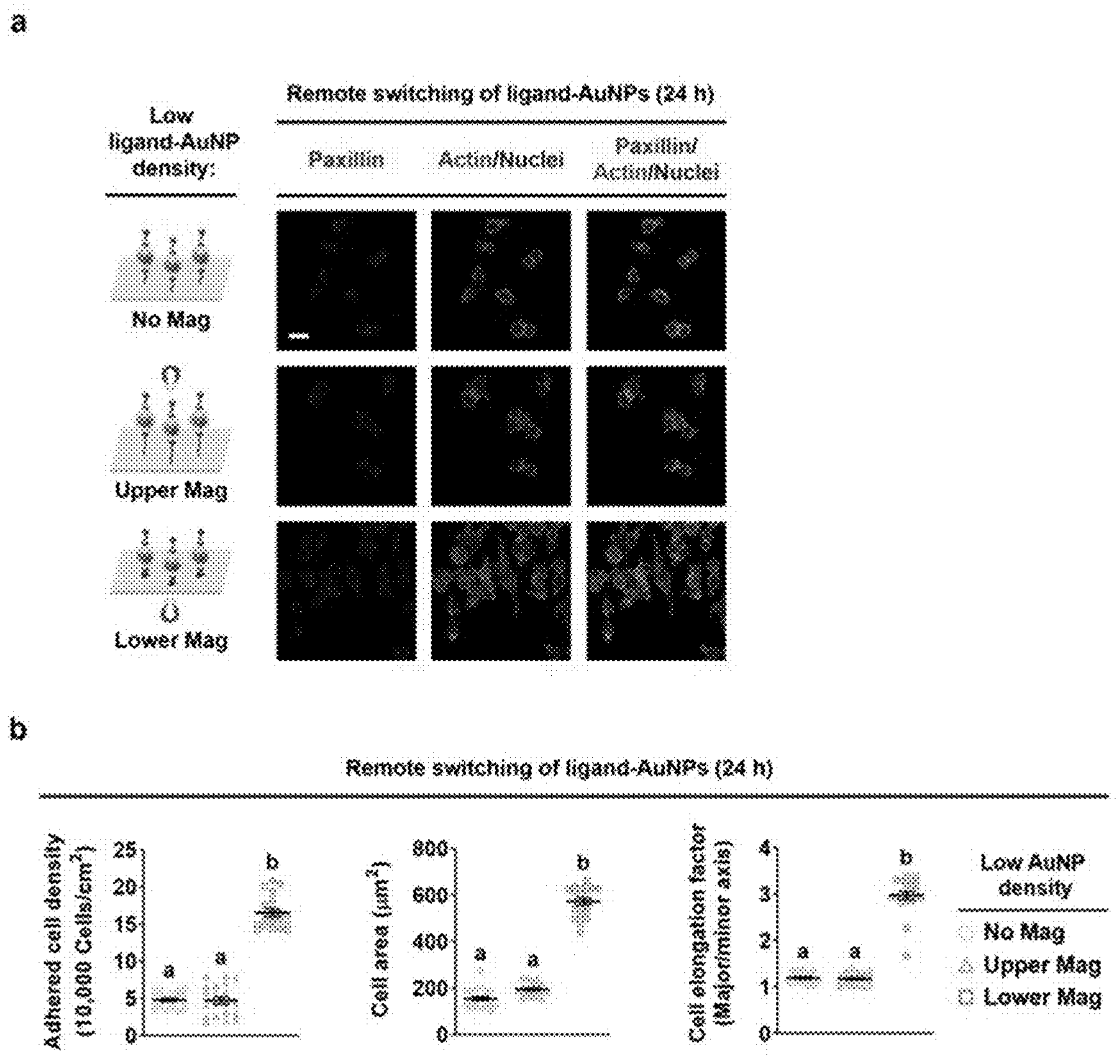
FIGS. 29 to 34 show the results of examining the degree of macrophage adhesion to nanosatellite-substrate complexes, prepared by modulating only the density of gold nanoparticles, depending on the direction in which a magnetic field is applied to the nanosatellite-substrate complexes.
Figure 30:
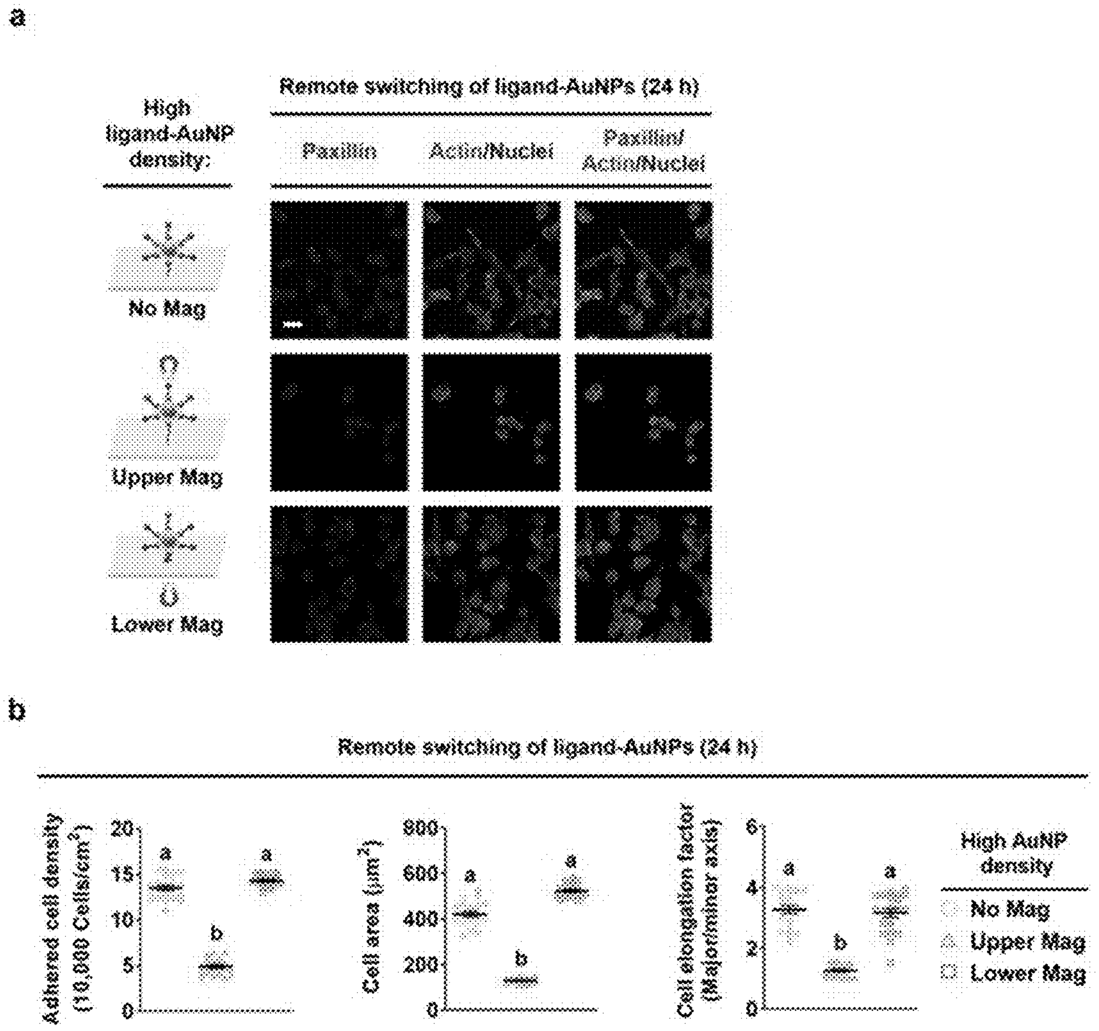

FIG. 29 shows the results of the experiment conducted at Low ligand-AuiNP density, and FIG. 30 shows the results of the experiment conducted at High ligand-AuiNP density.

It can be confirmed that, in the two cases, the adhesion of macrophages significantly decreased in Upper Mag and the adhesion of macrophages significantly increased in the "Lower Mag" condition, compared to the No Mag condition. This phenomenon can also be found in FIG. 24*b*. This means that the adhesion and polarization of macrophages can be regulated by applying a magnetic field to the nanosatellite-substrate complex.

Figure 31:
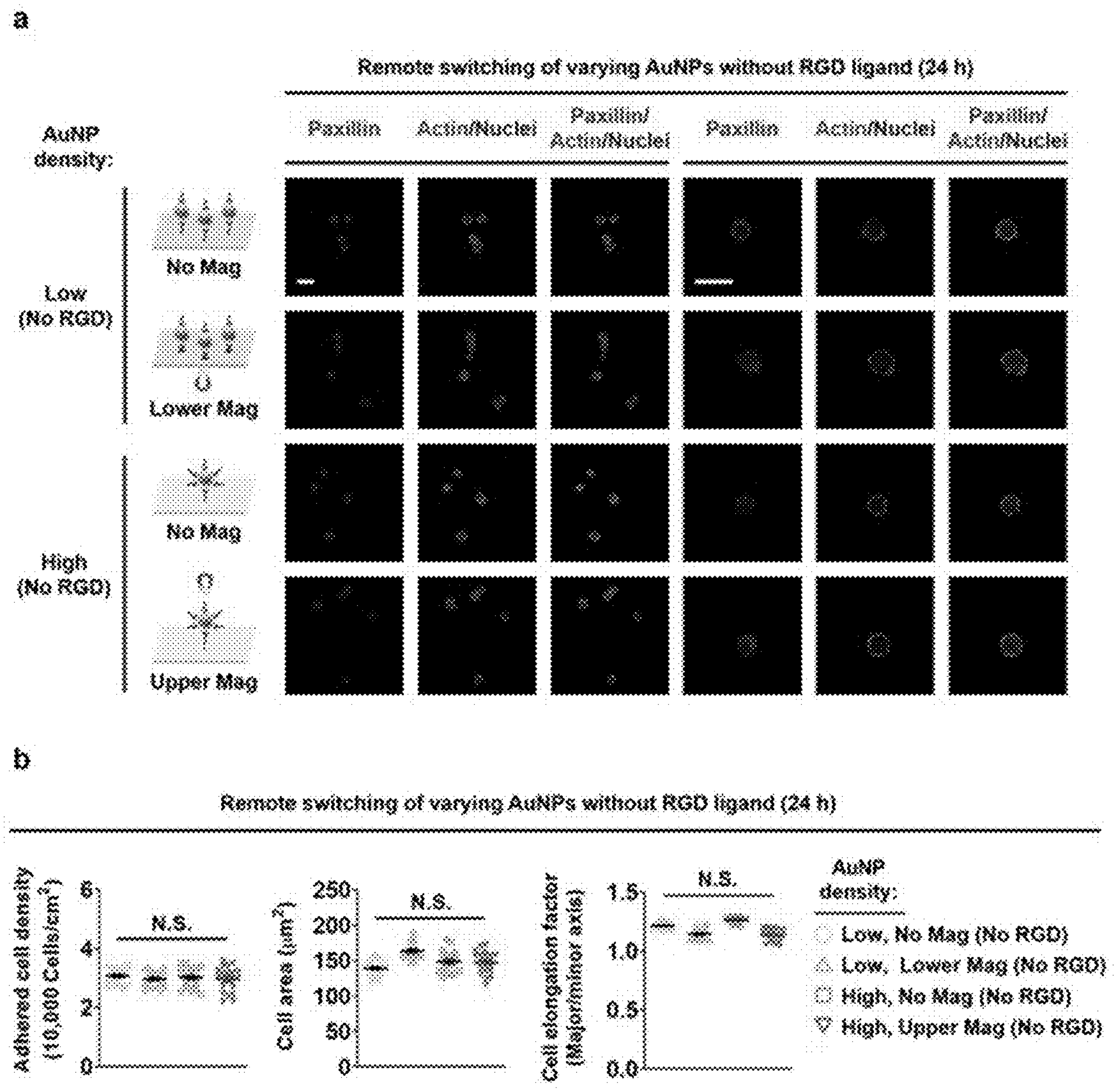
Figure 32:
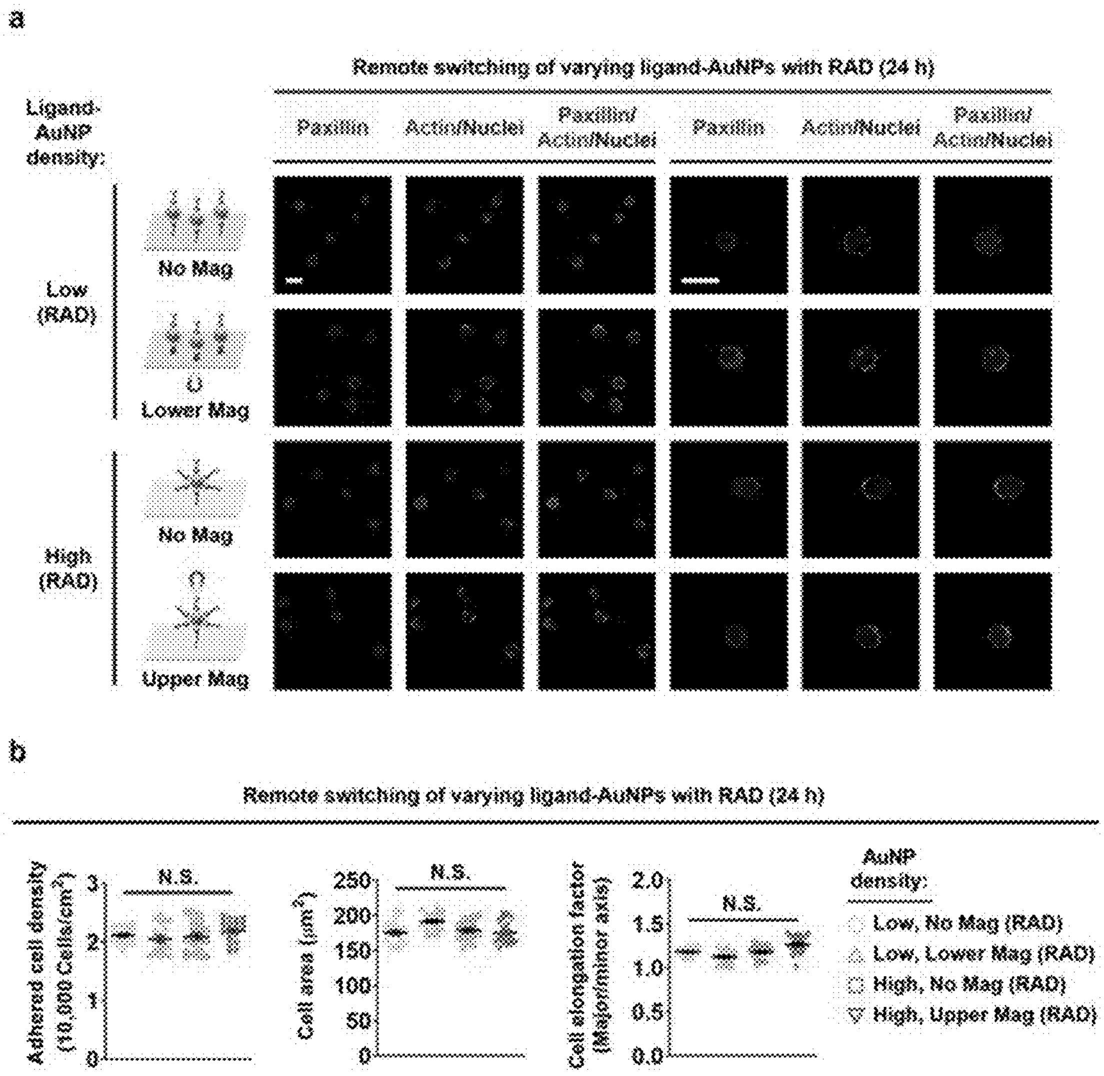

FIGS. 31 and 32 shows the results of the experiments conducted by applying a magnetic field to the nanosatellite-substrate complex in the absence of the ligand and in the case where the RAD ligand was conjugated. Almost no macrophages adhered regardless of whether the magnetic field was applied, confirming again that the RGD ligand is essential for macrophage adhesion.

Figure 33:
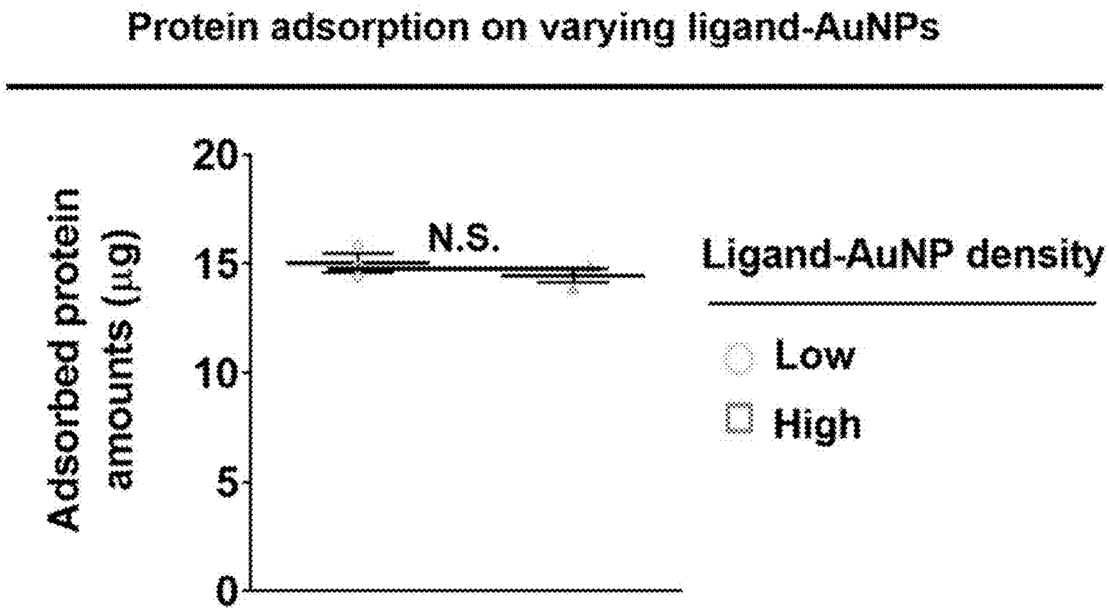
Figure 34:
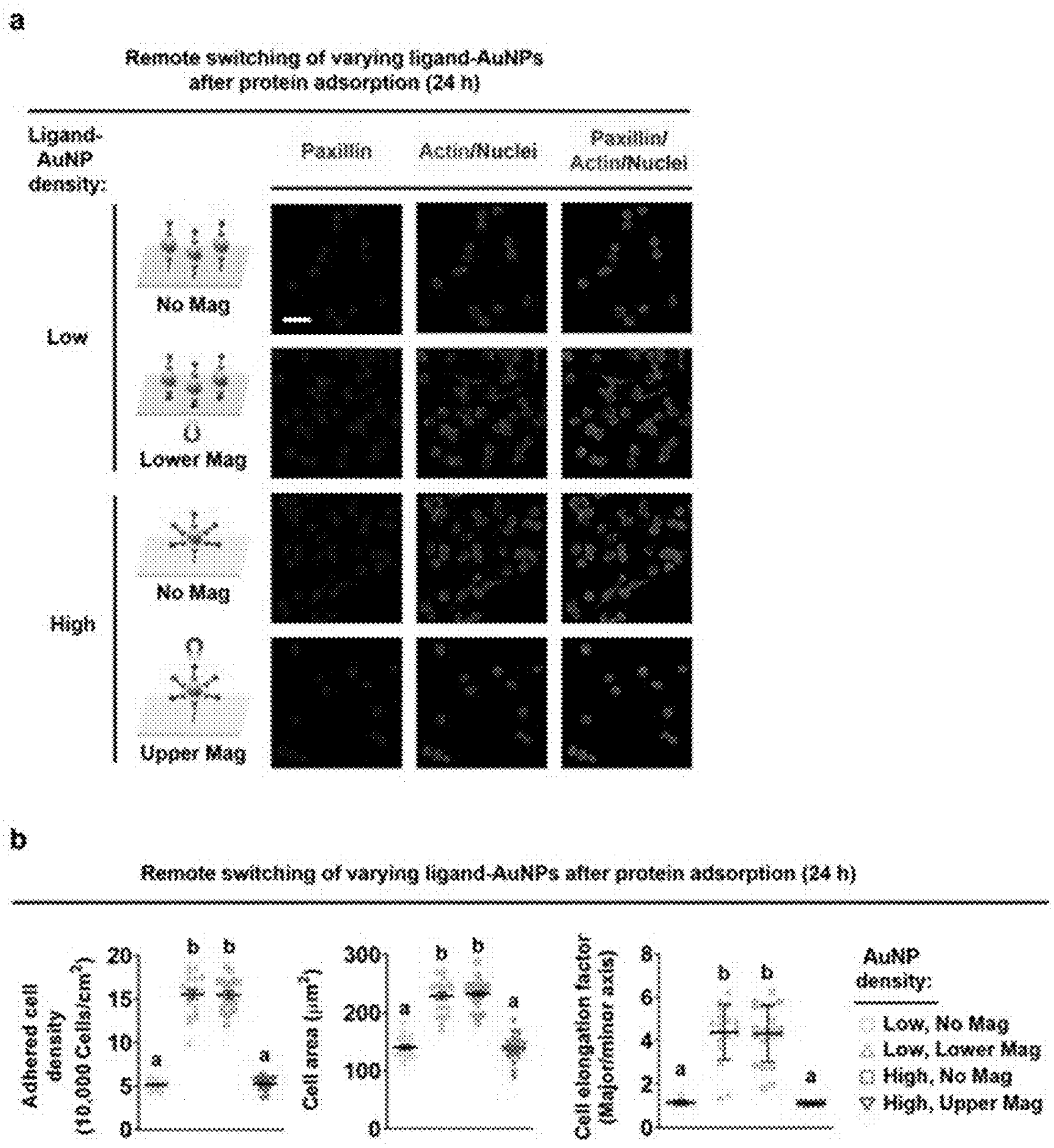

FIGS. 33 and 34 show the results of the experiments conducted on the case in which the RGD ligand was present and after the substrate was coated with the protein, and indicate that the nanosatellite-substrate complex is effective in regulating macrophage adhesion. FIGS. 33 and 34 show the results of the experiments conducted after the substrate of the nanosatellite-substrate complex was coated with the protein by 24 hours of incubation in a culture medium containing 10% fetal bovine serum. In FIG. 33, data were expressed as mean±standard error (n=3). In FIG. 34, the scale bar is 20 μm, and data are expressed as mean±standard error (n=20).

(3) Experiment on Macrophage Polarization by Application of Magnetic Field

The organization of cytoskeletal actin and integrin-adhesion complex, including paxillin in macrophages resulting in their elongated spreading, has been reported to activate their M2 polarization through ROCK signaling. Thus, the present inventors conducted an experiment on regulating M1 and M2 polarization by modulating the nanosatellite-substrate complex.

Figure 35:
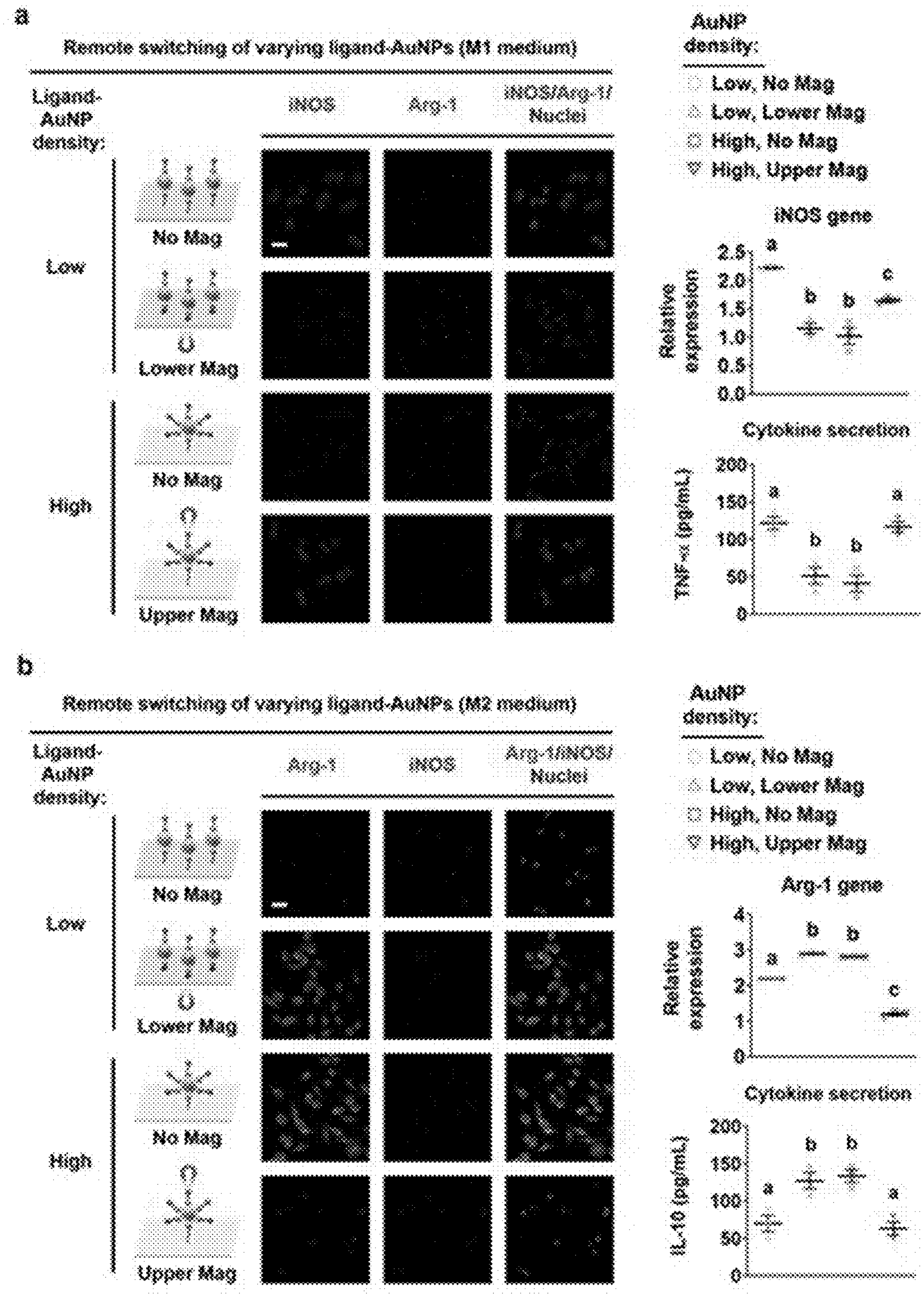
FIGS. 35 to 39 show the results of experiments conducted on macrophage polarization by applying a magnetic field to nanosatellite-substrate complexes prepared by modulating only the density of gold nanoparticles.

FIG. 35 shows the results of comparing the polarization of macrophages after forming "No Mag", "Lower Mag" and "Upper Mag" conditions in the nanosatellite-substrate complex. The scale bar is 20 μm, and data are expressed as mean±standard error (n=3).

FIG. 35*a* shows the results of the experiment conducted in M1 medium, and it can be confirmed that the expression of iNOS and TNF-α and the secretion of TNF-α were very inhibited in the "Low density" and "Upper Mag" conditions compared to the "No Mag" condition. This means that macrophage adhesion is inhibited and M1 polarization is promoted in the "Low density" and "Upper Mag" conditions.

FIG. 35*b* shows the results of the experiment conducted in M2 medium, and it can be confirmed that the expression of Arg-1 and Yml and the secretion of IL-10 were promoted in the "High density" and "Lower Mag" conditions compared to the "No Mag" condition. On the other hand, expression of iNOS was almost absent. This means that macrophage adhesion and M2 polarization are promoted in the "high density" and "lower Mag" conditions.

Figure 36:
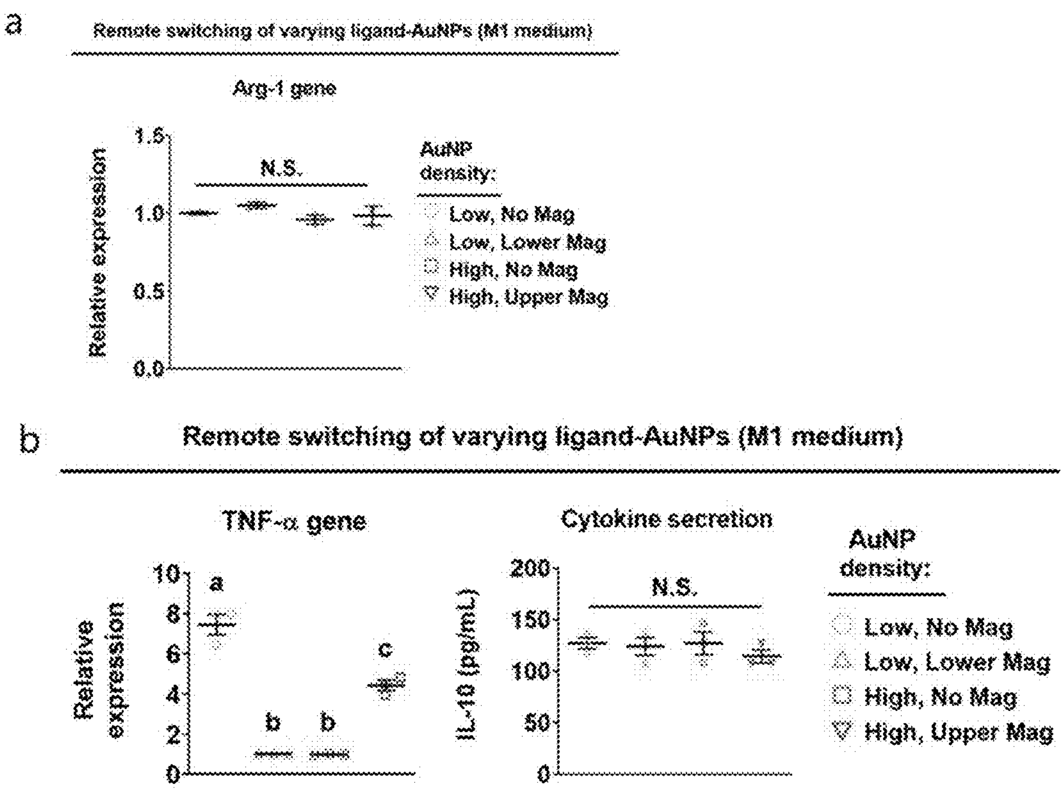
Figure 37:
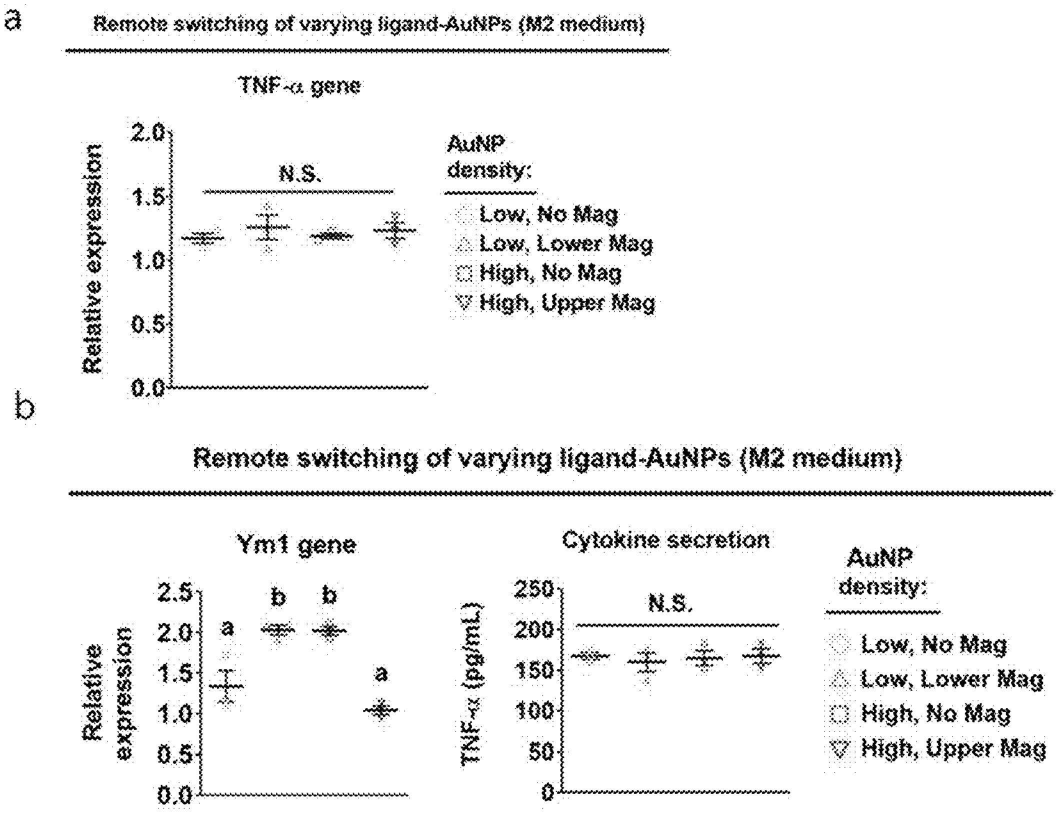

FIGS. 36 and 37 show M2 polarization after culturing in M1 medium or M1 polarization after culturing in M2 medium, as a control. In both cases, there was no significant difference, and it is recommended to use a medium suitable for each condition.

Figure 38:
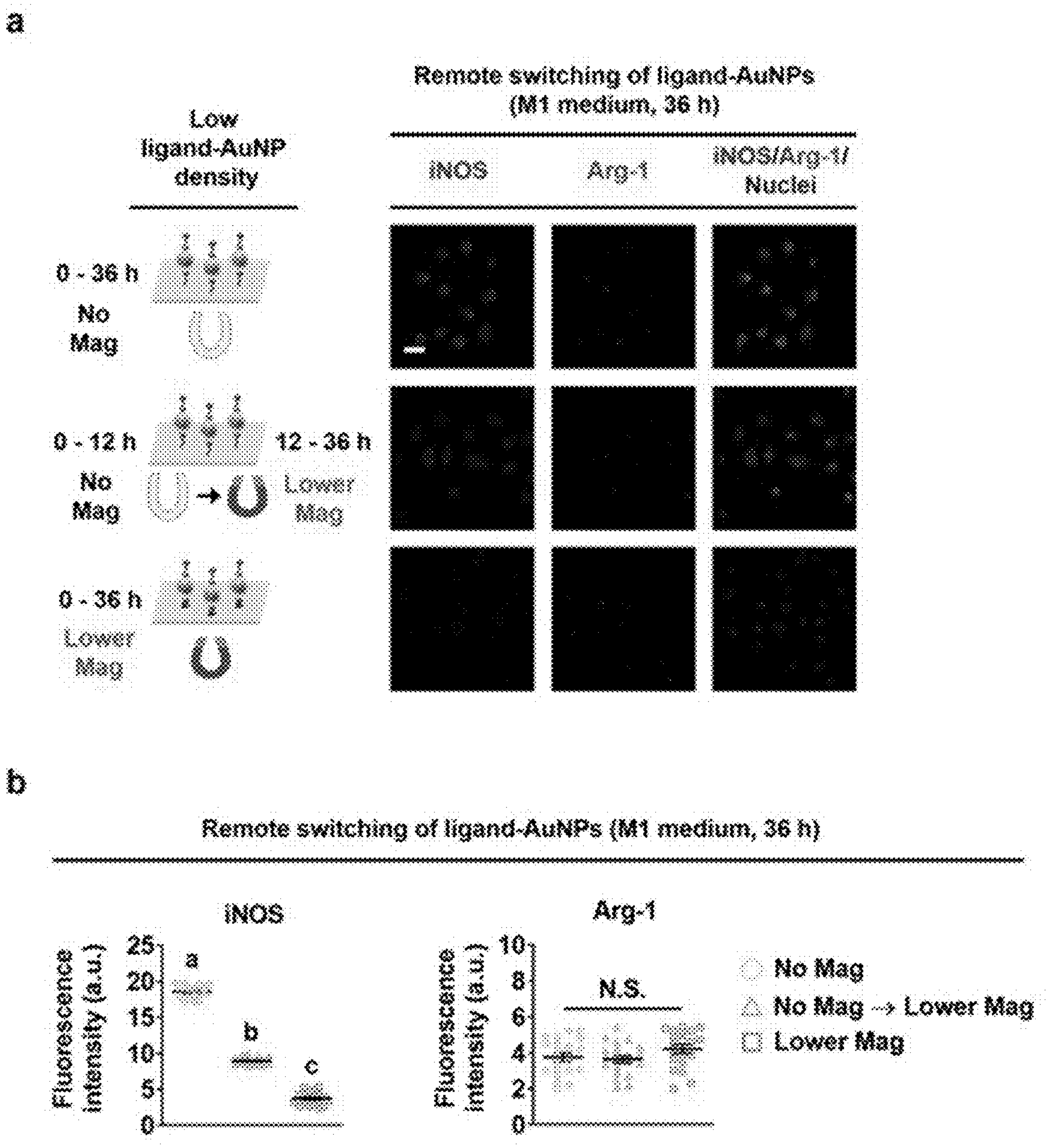
Figure 39:
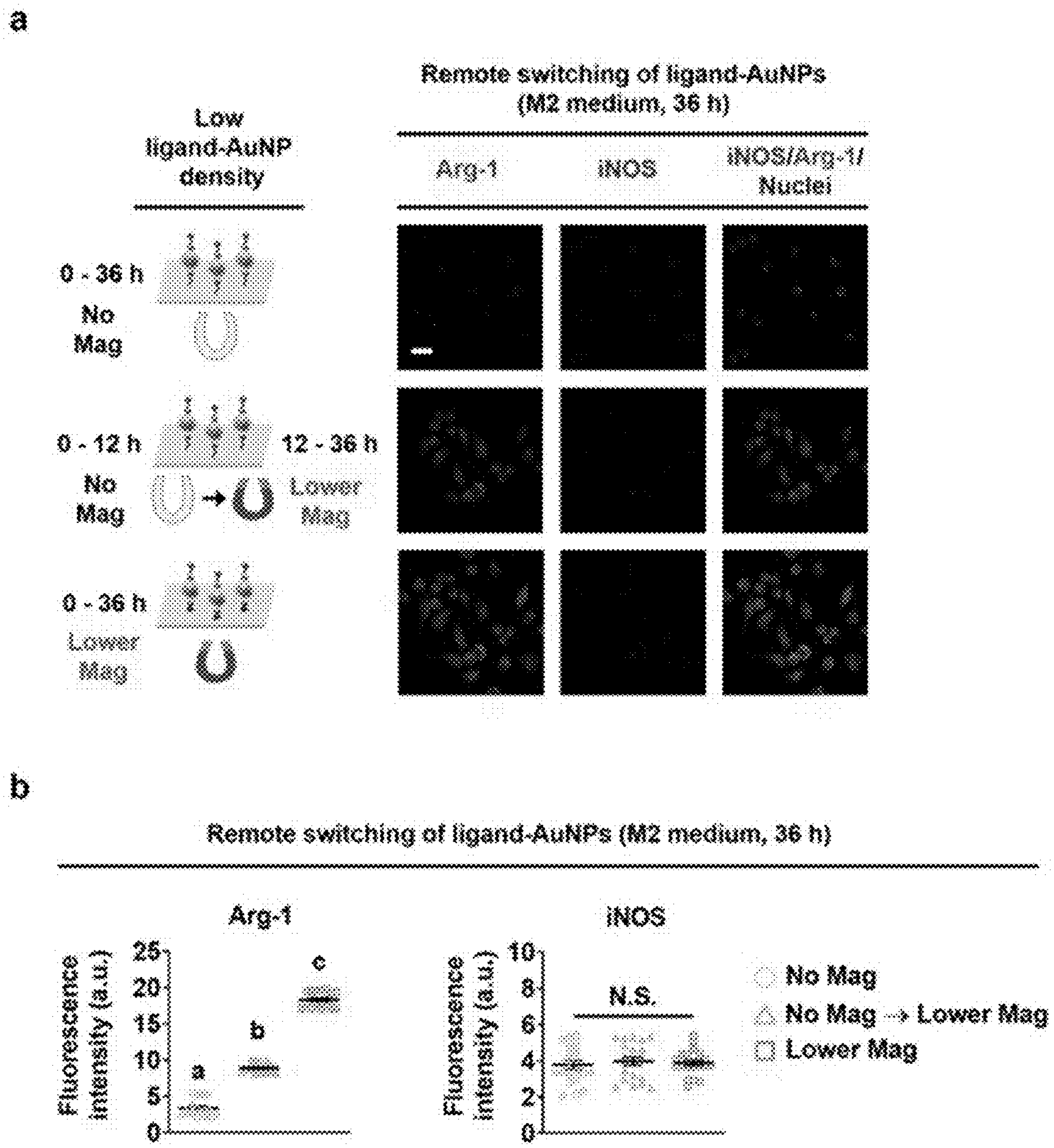

FIGS. 38 and 39 show the results of the experiments conducted in M1 medium and M2 medium in the low density by the application of a magnetic field. It can be confirmed that, at 36 hours after applying the magnetic field in the "Lower Mag" condition, expression of iNOS decreased in M1 medium but expression of Arg-1 increased in M2 medium, compared to the "No Mag" condition. Therefore, it can be confirmed that, even when the nanoassembly density is low, the adhesion and polarization of macrophages can be regulated by applying a magnetic field in a specific direction.

(4) Experiment on Macrophage Polarization Using Inhibitors

The present inventors deciphered the adhesion-aided M2 polarization of macrophages using specific inhibitors of actin polymerization, myosin II, and ROCK, which are proteins involved in macrophage adhesion.

Figure 40:
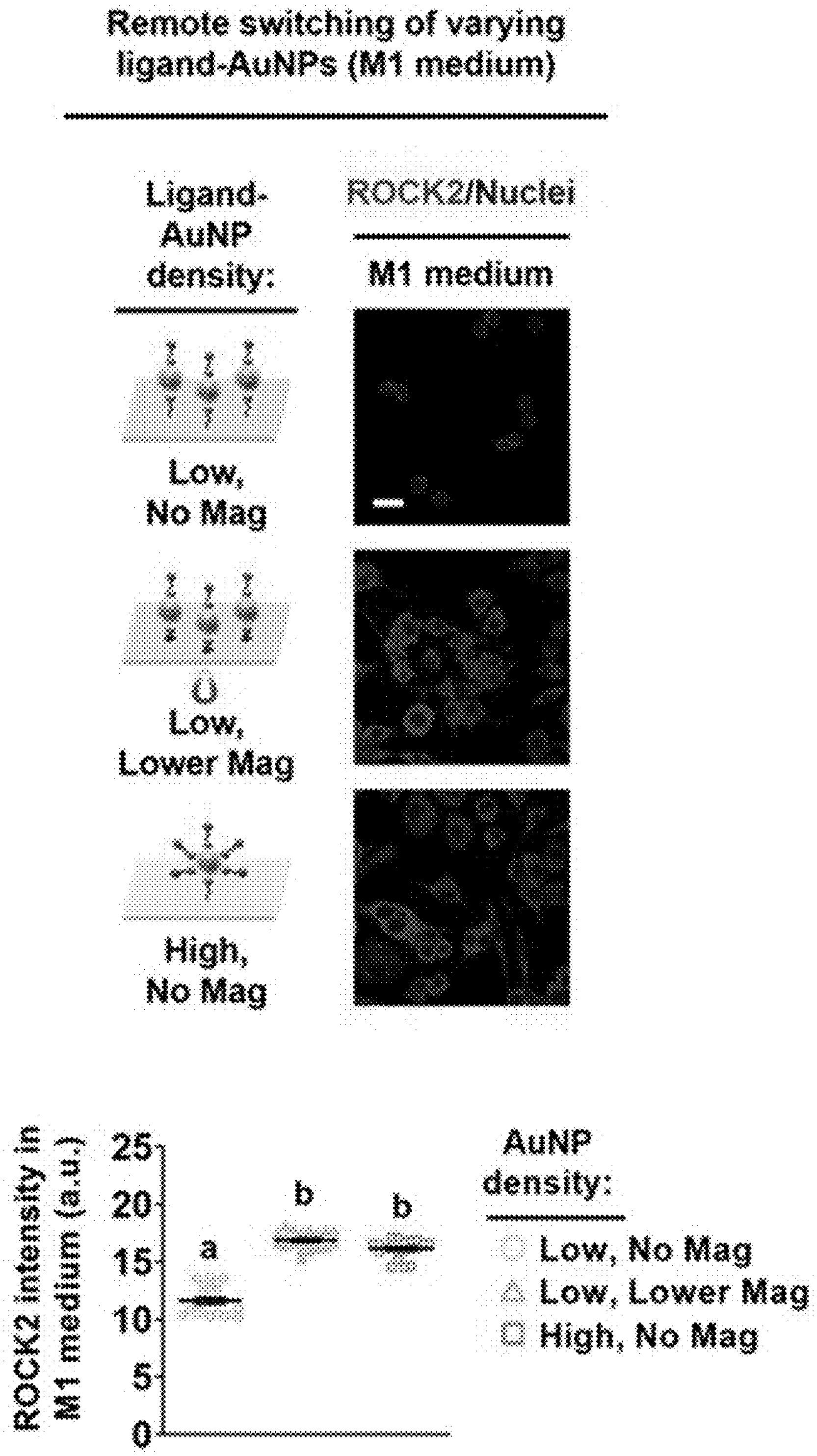
FIGS. 40 to 43 show the results of experiments conducted on macrophage polarization using nanosatellite-substrate complexes, prepared by modulating only the density of gold nanoparticles, in the presence of inhibitors.
Figure 41:
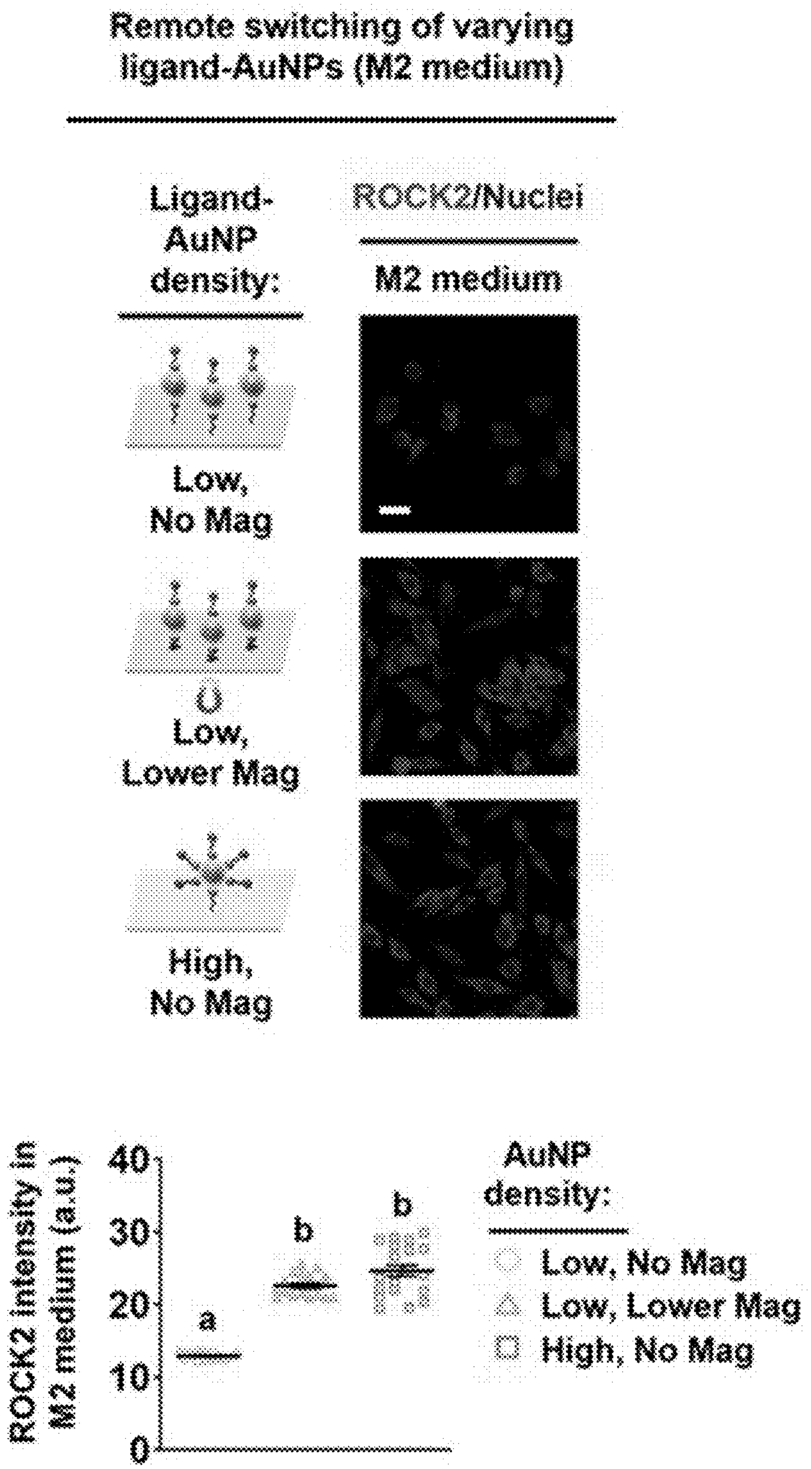

FIGS. 40 and 41 show the formation of adhesion structures that facilitate ROCK2 expression and stimulate M2 polarization in the High density and Lower Mag conditions in M1 medium and M2 medium, respectively.

Figure 42:
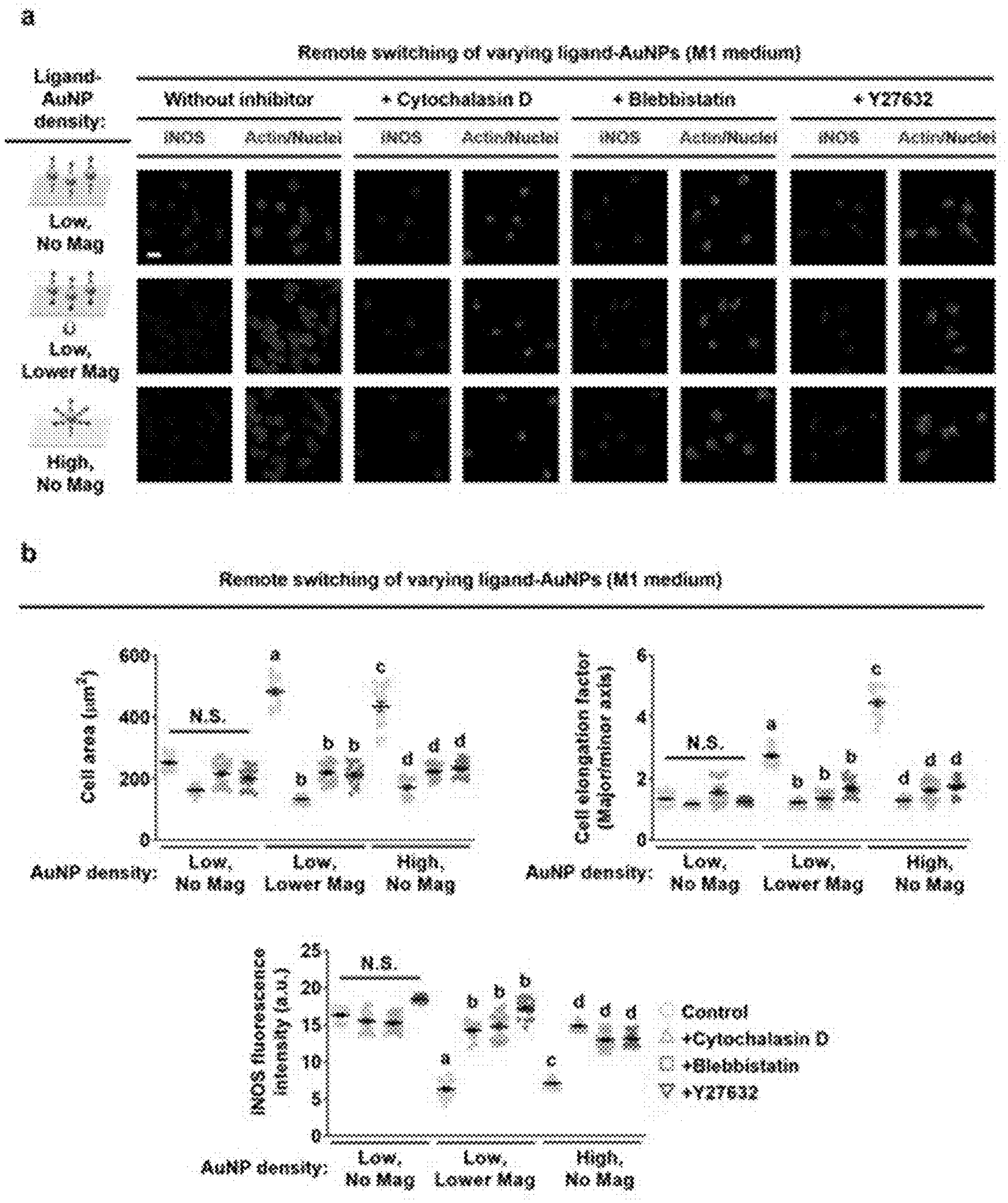
Figure 43:
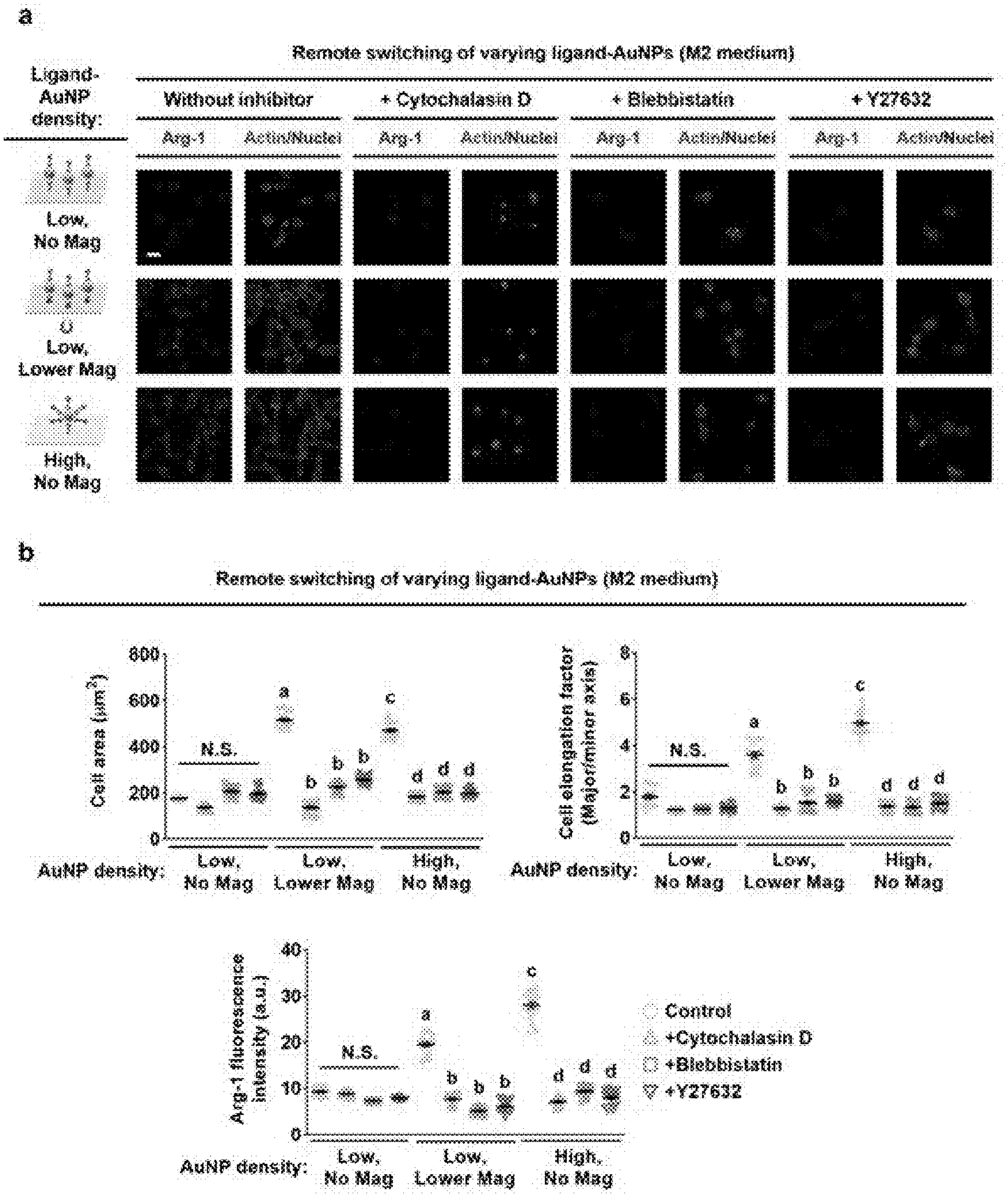

FIGS. 42 and 43 show the results of observation of macrophage adhesion and polarization after addition of a specific inhibitor of each protein in M1 medium and M2 medium, respectively. As inhibitors of actin polymerization, myosin II and ROCK, cytochalasin D, blebbistatin and Y27632 were used, respectively, and observation was performed 36 hours after culturing macrophages in each medium.

From FIG. 42 (M1 medium), it could be seen that, in the absence of the inhibitors, expression of iNOS hardly occurred in the "Lower Mag" condition and the "high density" condition, but in the presence of the inhibitors, iNOS was expressed, suggesting that the inhibitors hindered M1 polarization. Also, actin/nuclei were actively expressed in the absence of the inhibitor in the "Lower Mag" condition and the "high density" condition, but the expression levels thereof decreased in the presence of the inhibitors.

From FIG. 43 (M2 medium), it could be seen that, in the absence of the inhibitors, the expression of Arg-1 and actin/nucleus was stimulated in the "Lower Mag" condition and the "high density" condition, but in the presence of the inhibitors, the expression thereof decreased in all cases, indicating that the inhibitors hindered M2 polarization.

This means that the application of a magnetic field may regulate macrophage adhesion and M1/M2 polarization induced by the molecular machinery of F-actin, myosin II and ROCK.

2. Modulation of Diameter of Gold Nanoparticles and Distance Between Gold Nanoparticles Experiments were conducted to examine whether the adhesion and polarization of macrophages could be regulated by applying a magnetic field to the nanosatellite-substrate complex prepared by modulating the diameter of gold nanoparticles and the distance between adjacent gold nanoparticles.

Figure 44:
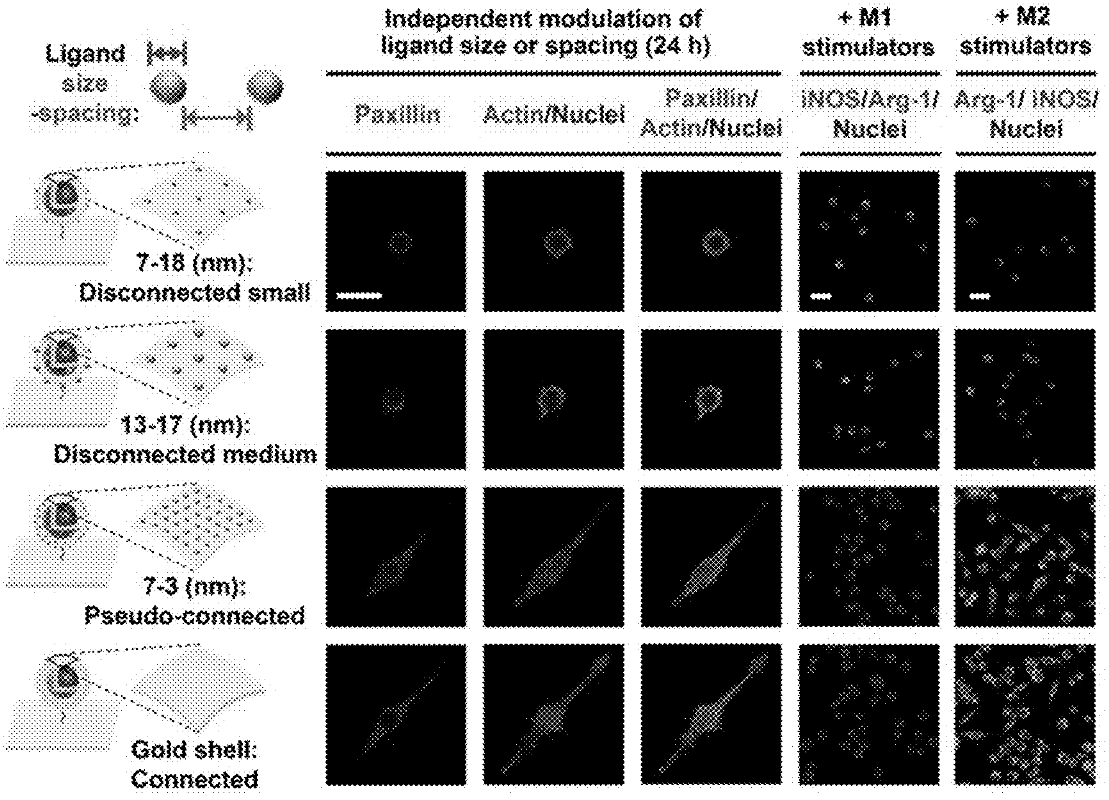
FIG. 44 shows the results of examining whether pseudo-connection is created when the distance between adjacent gold nanoparticles is short.

(1) Pseudo-Connection in the Case in which the Distance Between Adjacent Gold Nanoparticles is Short Experiments were conducted to examine whether the adhesion and polarization of macrophages could be regulated depending on the diameter of and distance between gold nanoparticles in the "7-18" group, "13-17" group, "7-3" group and "gold shell" group, and the results are shown in FIG. 44. Quantification of these results can be found in FIG. 22*c*.

In the immunofluorescence staining image, it can be confirmed that macrophage adhesion and M2 polarization were promoted in the "7-3" group and the "gold shell" group compared to the "7-18" group and the "13-17" group. In the "7-3" group and the "gold shell" group, the cell elongated cell morphology appeared and Arg-1 expression increased, but in the "7-18" group and "13-17" group, there was no cell elongation, round cell morphology appeared, and iNOS expression increased. This is because pseudo-connection occurred in the "7-3" group at a level comparable to that of the gold shell group in which the gold nanoparticles are connected to each other, thereby stimulating the adhesion formation of macrophages.

Also, when comparing the "7-3" group with the "7-18" group, in the "7-18" group, the adhesion of macrophages was not increased because the distance between the adjacent gold nanoparticles was large, even though the gold nanoparticles had the same diameter. In addition, macrophage adhesion was not increased even in the "13-17" group in which only the distance between adjacent gold nanoparticles was increased compared to that in the "13-17" group. This means that the adhesion and polarization of macrophages can regulated only when the diameter of gold nanoparticles and the distance between adjacent gold nanoparticles are appropriately modulated at the same time.

Also, in the experiment on polarization of macrophages, the present inventors investigated whether the pseudo-connected (the "7-3" group) and the "gold shell" group promoted M2 polarization. ROCK signaling is implicated in inhibiting M1 polarization while inducing M2 polarization and elongating the morphology of macrophages to form robust cytoskeletal adhesion. Macrophages were cultured with each nanosatellite-substrate complex in M1 medium or M2 medium for 36 hours. Immunofluorescent staining images of the "7-3" and "gold shell" groups demonstrated pervasive expression of M2 polarization marker (Arg-1) in the presence of M2 stimulators but minimal expression of M1 polarization marker (iNOS) despite the presence of M1 stimulators. Conversely, it can be confirmed that, in the "7-18" and "13-17" groups, expression of iNOS was stimulated and expression of Arg-1 was minimized. This means that when gold nanoparticles are pseudo-connected ("7-3" group) or connected ("gold shell" group), macrophage adhesion is promoted to mediate M2 polarization and restrain M1 polarization. Conversely, in the "7-18" group and "13-17" group in which gold nanoparticles were not connected, adhesion of macrophages was inhibited, resulting in opposite results.

(2) Experiment on Regulation of Integrin Binding and Clustering

Figure 45:
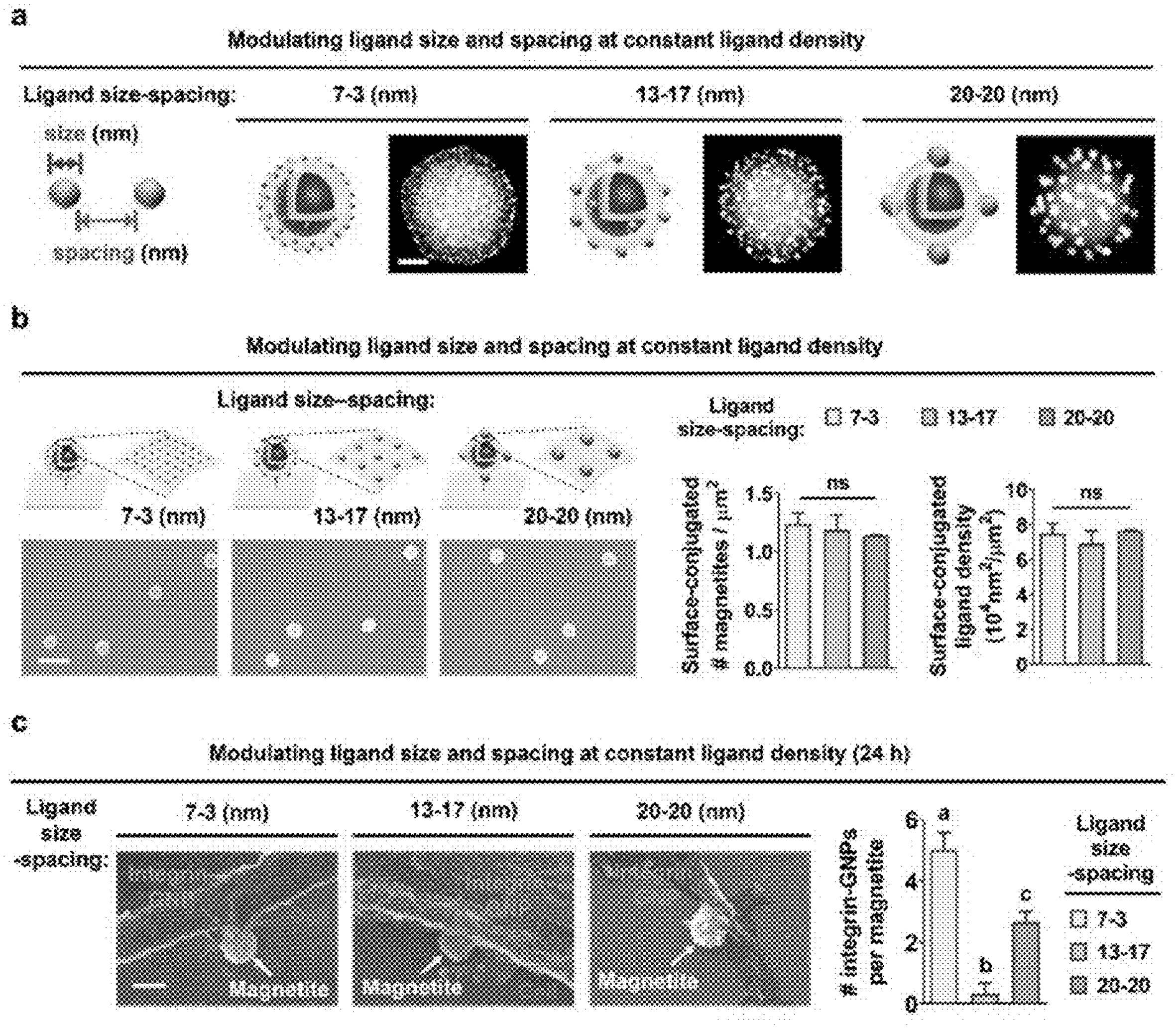
FIGS. 45 to 47 show the results of experiments on integrin binding and clustering to nanosatellite-substrate complexes prepared by modulating the diameter of gold nanoparticles and the distance between adjacent gold nanoparticles.
Figure 46:
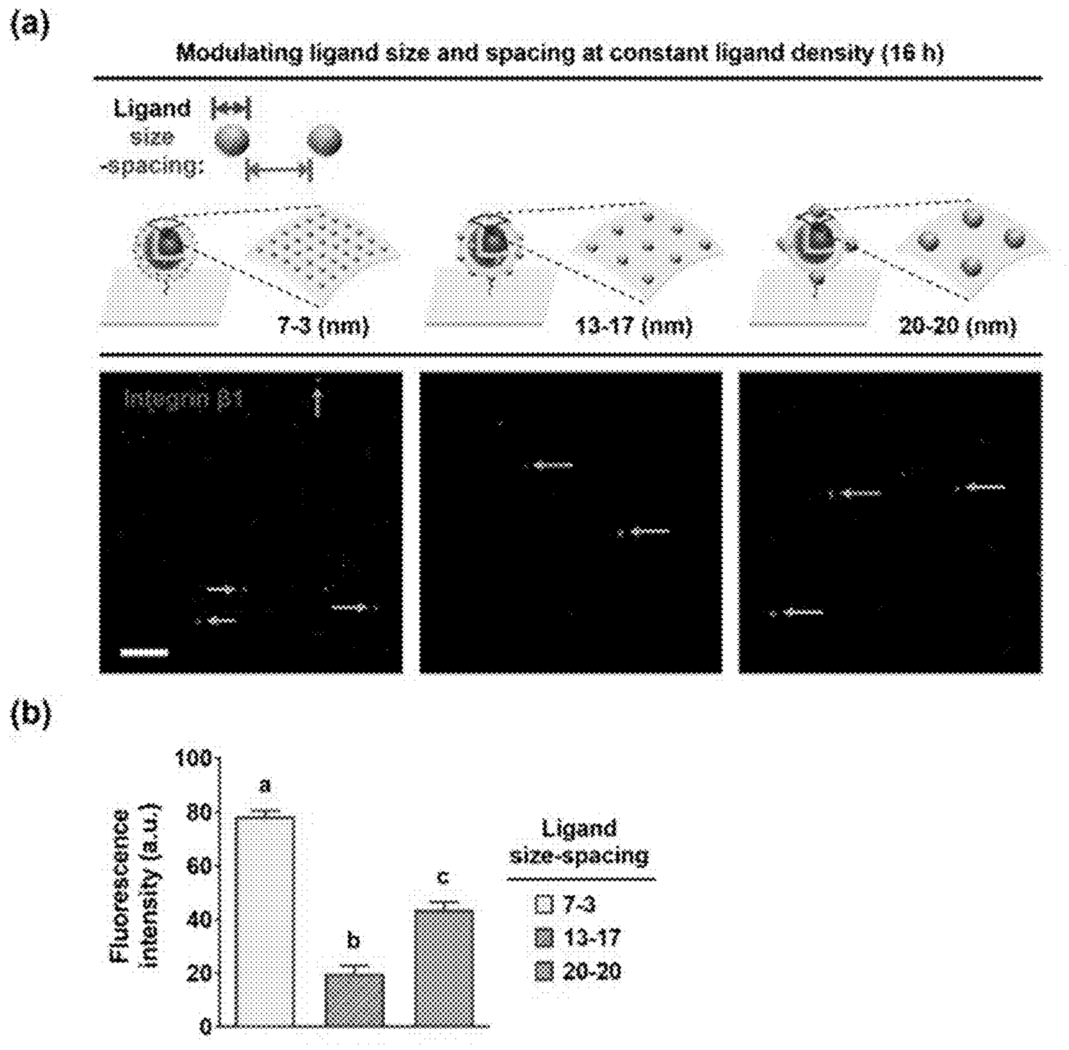

Experiments were conducted to examine whether integrin binding and clustering could be regulated in the "7-3" group, "13-17" group and "20-20" group, and the experimental results are shown in FIGS. 45 and 46.

SEM images in FIG. 45*b* demonstrated that the densities of the nanosatellite structures in all the groups were similar (1.14 to 1.24 per $\mu m^2$). In addition, the calculated densities of the nanoassemblies conjugated to the surface of the substrate in the groups were similar ($6.91\times10^4$ to $7.65\times10^4$).

Figure 47:
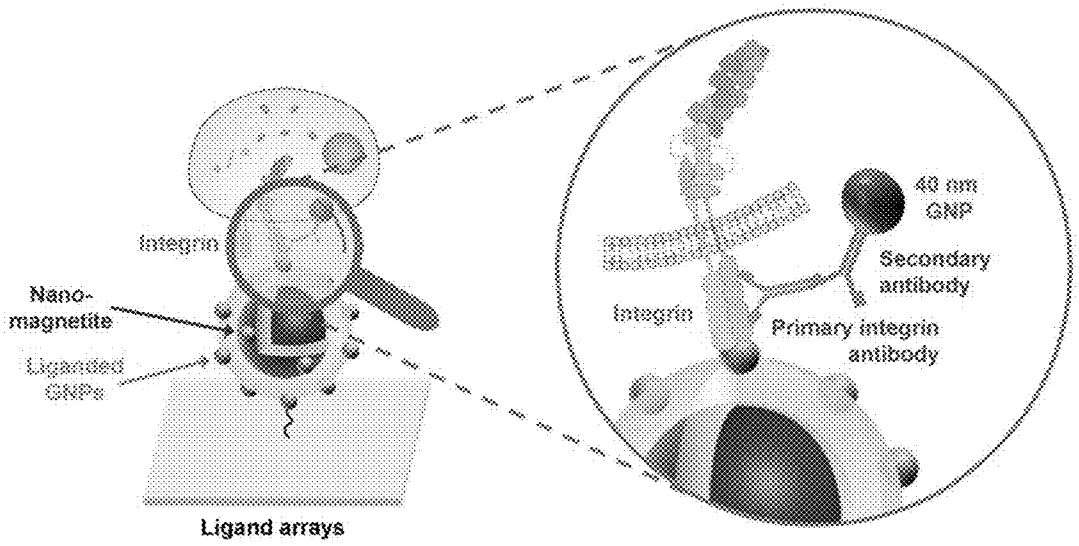

FIG. 46 shows the results of examining the efficiency of integrin β1 binding and clustering. Immunofluorescent staining of integrin β1 and fluorescence intensity quantification showed that integrin β1 was markedly clustered in the "7-3" group, but was slightly clustered in the "20-20" group. Furthermore, using 40-gold nanoparticles coated with secondary antibody, an immunolabeling experiment was conducted to examine whether integrins coated and labeled with primary antibody bound to the nanoassemblies (specifically the RGD ligand). FIG. 47 schematically shows this experiment. FIG. 45*c* shows SEM images and quantification about whether macrophages cultured for 24 hours adhered to the nanoassemblies. From the SEM images and quantification, it can be confirmed that integrin β1 actively clustered in the "7-3" group, but slightly clustered in the "20-20" group, and minimally to negligibly clustered in the "13-17" group.

(3) Experiment on Macrophage Adhesion and Polarization

The tendency of macrophage adhesion and polarization in the nanosatellite-substrate complex of each group was investigated.

Figure 48:
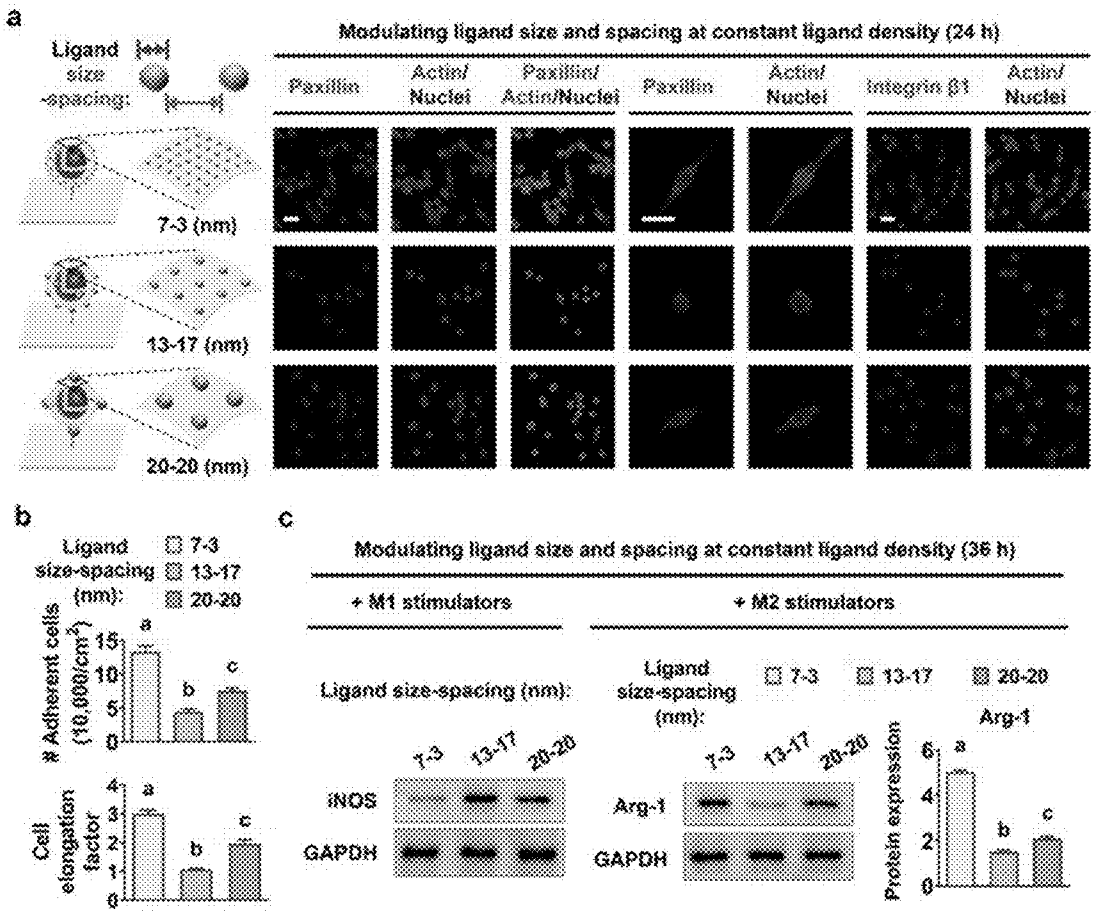
FIGS. 48 to 51 show the results of experiments conducted on macrophage adhesion and polarization using nanosatellite-substrate complexes, prepared by modulating the diameter of gold nanoparticles and the distance between adjacent gold nanoparticles, without applying a magnetic field to the nanosatellite-substrate complexes.

FIG. 48*a* shows that assemblies of F-actin and paxillin adhesion complexes show constant trends in the "7-3" group, the "13-17" group and the "20-20" group. In addition, the quantification graph (FIG. 48*b*) also shows the same trends.

Figure 49:
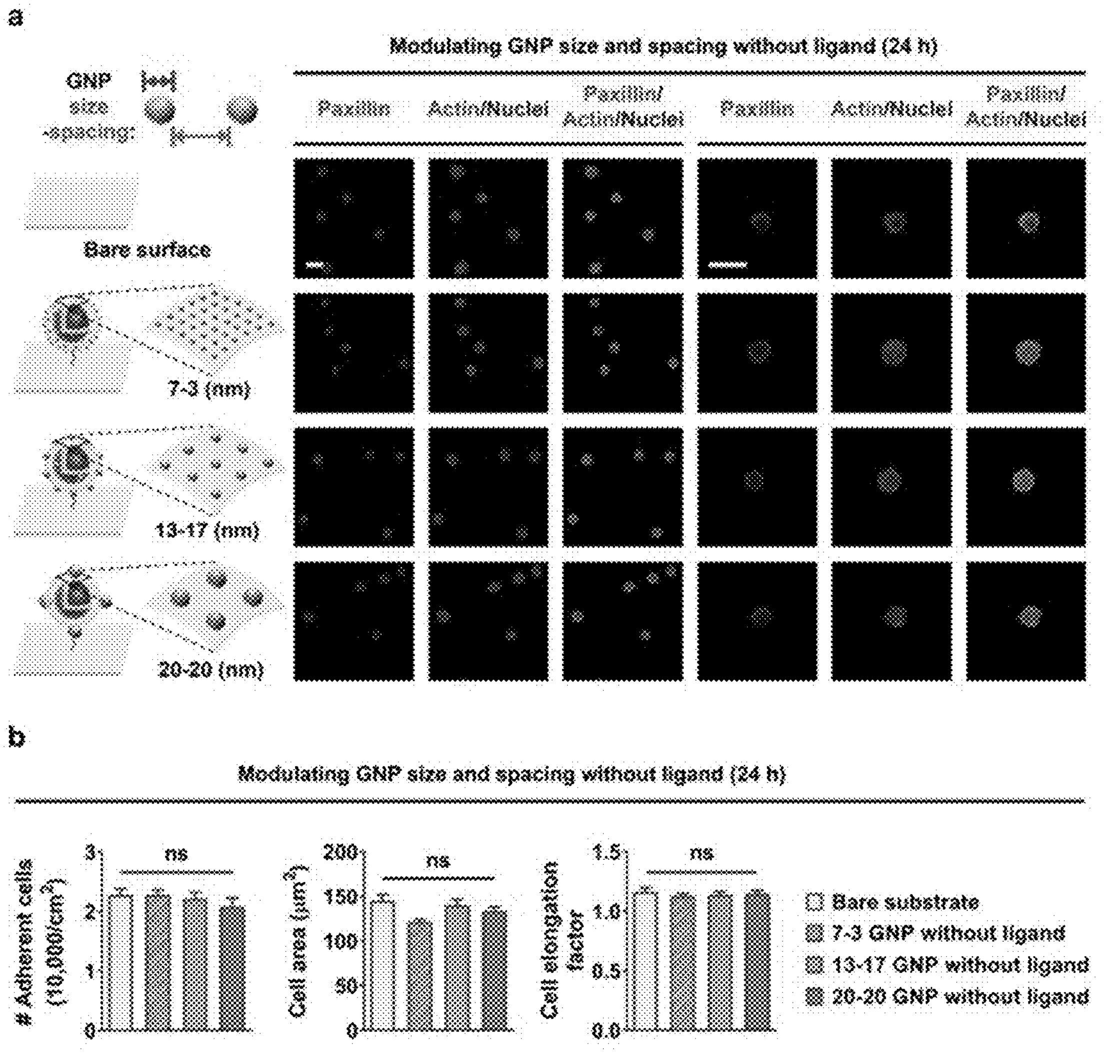
Figure 50:
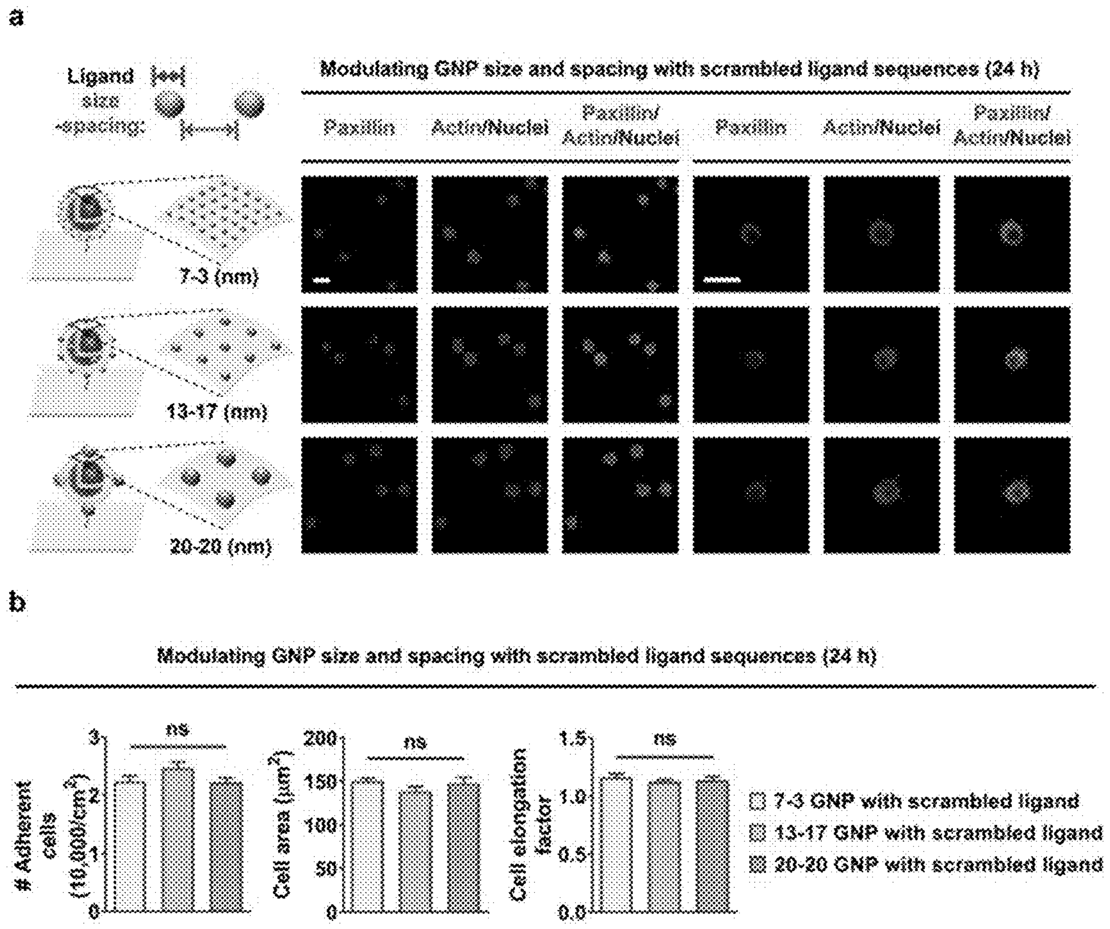

As negative controls, nanosatellite-substrate complexes corresponding to the following cases were prepared, and experiments on macrophage adhesion were performed using the nanosatellite-substrate complexes: a case where only a substrate was present, a case where there was no ligand (FIG. 49), and a case the RAD ligand was conjugated instead of the RGD ligand (FIG. 50). The experimental results confirmed that, like those in Experimental Example 3-1, macrophage adhesion hardly occurred, and the RGD ligand is essential for macrophage adhesion.

Figure 51:
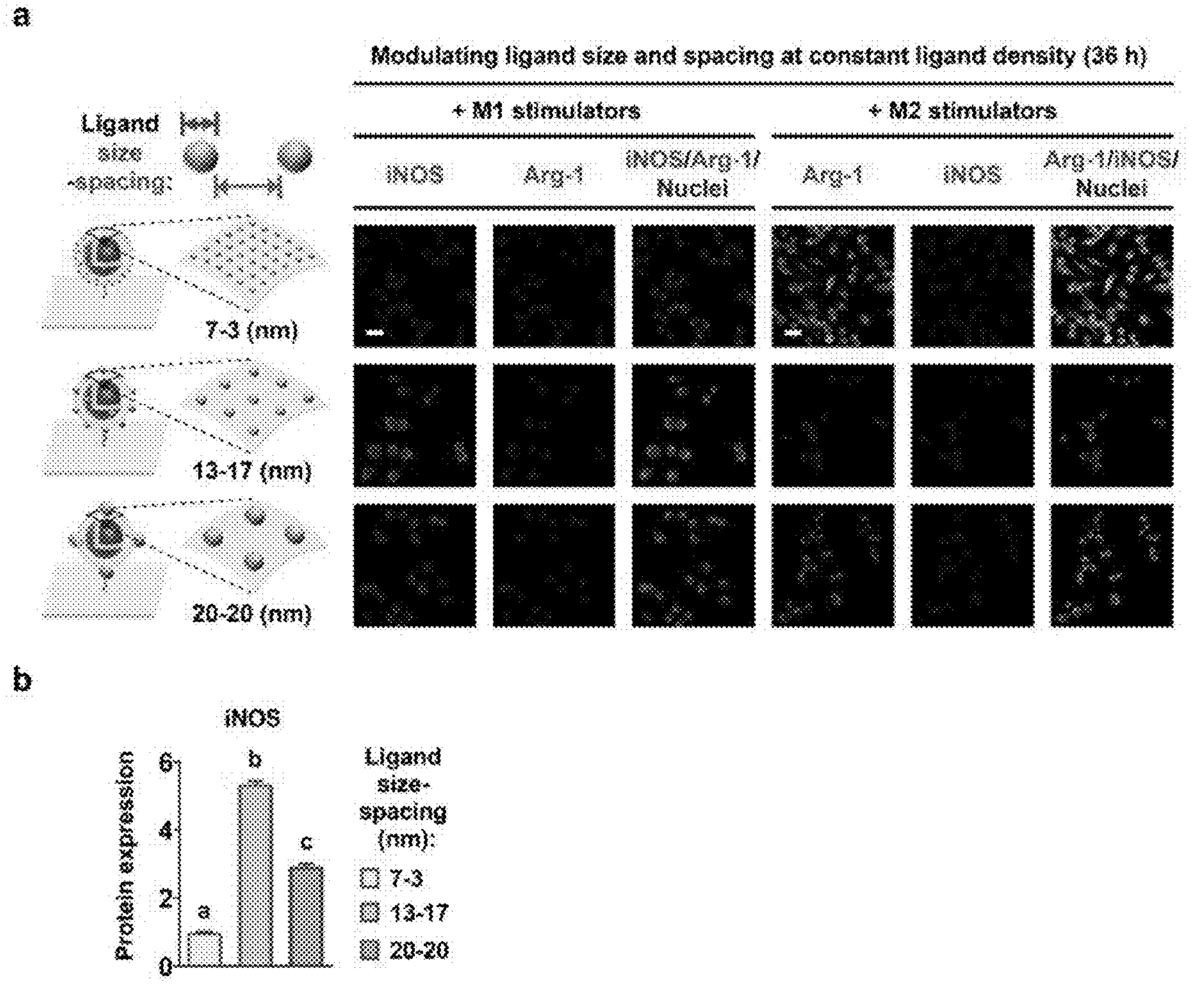

FIG. 51 shows immunofluorescence staining images of polarization in each nanosatellite-substrate complex group and a quantification graph therefor. When macrophages were cultured in the medium with M2 polarization stimulator, the expression of Arg-1 was the highest in the "7-3" group, moderate in the "20-20" group, and the lowest in the "13-17" group. On the other hand, the expression of the M1 polarization marker was almost absent. In addition, when macrophages were cultured in the medium with M1 polarization stimulators, the opposite results were shown. These results were consistent with western blotting images and subsequent quantification that show expression of Arg-1 and iNOS (FIG. 48*c*). In the western blotting results, the expression of iNOS was very high in the “13-17” group and very low in the “7-3” group. These results prove that integrin binding and clustering are facilitated in the “7-3” group, and as a result, macrophage adhesion-aided M2 polarization is promoted. Conversely, these results suggest that, in the “13-17” group, integrin binding and clustering are inhibited, and as a result, M1 polarization is promoted. The trend for the “20-20” group was between the other two groups.

The 3 nm edge-to-edge spacing of adjacent gold nanoparticles in the “7-3” group emulates the submolecular-level dimension of fibronectin in an equilibrated state. When the distance between adjacent gold nanoparticles is 3 nm, it is most probable that the binding and thus bridging of a single integrin molecule (10 nm in size) to any one RGD ligand are facilitated across the adjacent RGD ligands. This could be due to macrophages perceiving three adjacent RGDs as pseudo-connected ligands to form saturated integrin clusters, which facilitate M2 polarization. The level of this effect is similar to the effect shown in entirely connected ligands of “gold shell” group that exhibits significantly higher (by 275%) ligand density compared to the “7-3” group (pseudo-connected group) (see FIG. 22*c*).

In contrast, since the maximum dimension of fibronectin is approximately 16 nm, the edge-to-edge spacing of gold nanoparticles in the “7-18” group and the “13-17” group can emulate the FN dimension. When the distance between the gold nanoparticles is 16 nm or more, the binding of integrin molecules is highly inhibited such that macrophages perceive these as disconnected ligands, resulting in M1 polarization. Even though the gold nanoparticle size is significantly higher in the “13-17” group than in the “7-18” group, these two groups showed similar degrees of integrin binding and clustering, resulting in M1 polarization. These results substantiate that the distance between adjacent gold nanoparticles is the dominant factor rather than the diameter of gold nanoparticles in macrophage adhesion. Interestingly, even though the distance between adjacent gold nanoparticles in the “20-20” group is slightly higher, M2 polarization of macrophages is slightly facilitated compared to the “13-17” group. This is because, when the gold nanoparticles have a diameter of 20 nm, cell adhesion can be promoted and clustering can be increased by binding of multiple integrin molecules to each gold nanoparticle.

(4) Experiment on Regulation of Macrophage Adhesion and Polarization by Application of Magnetic Field An experiment was conducted to examine whether the adhesion and polarization of macrophages could be regulated by applying a magnetic field to each nanosatellite-substrate complex. Since the fibronectin-bearing 3-D ECM continuously remodels itself to dynamically present ligands, the experiment was conducted to examine the adhesiveness of the RGD ligand could be regulated by vertically moving the nanosatellite structure.

Figure 52:
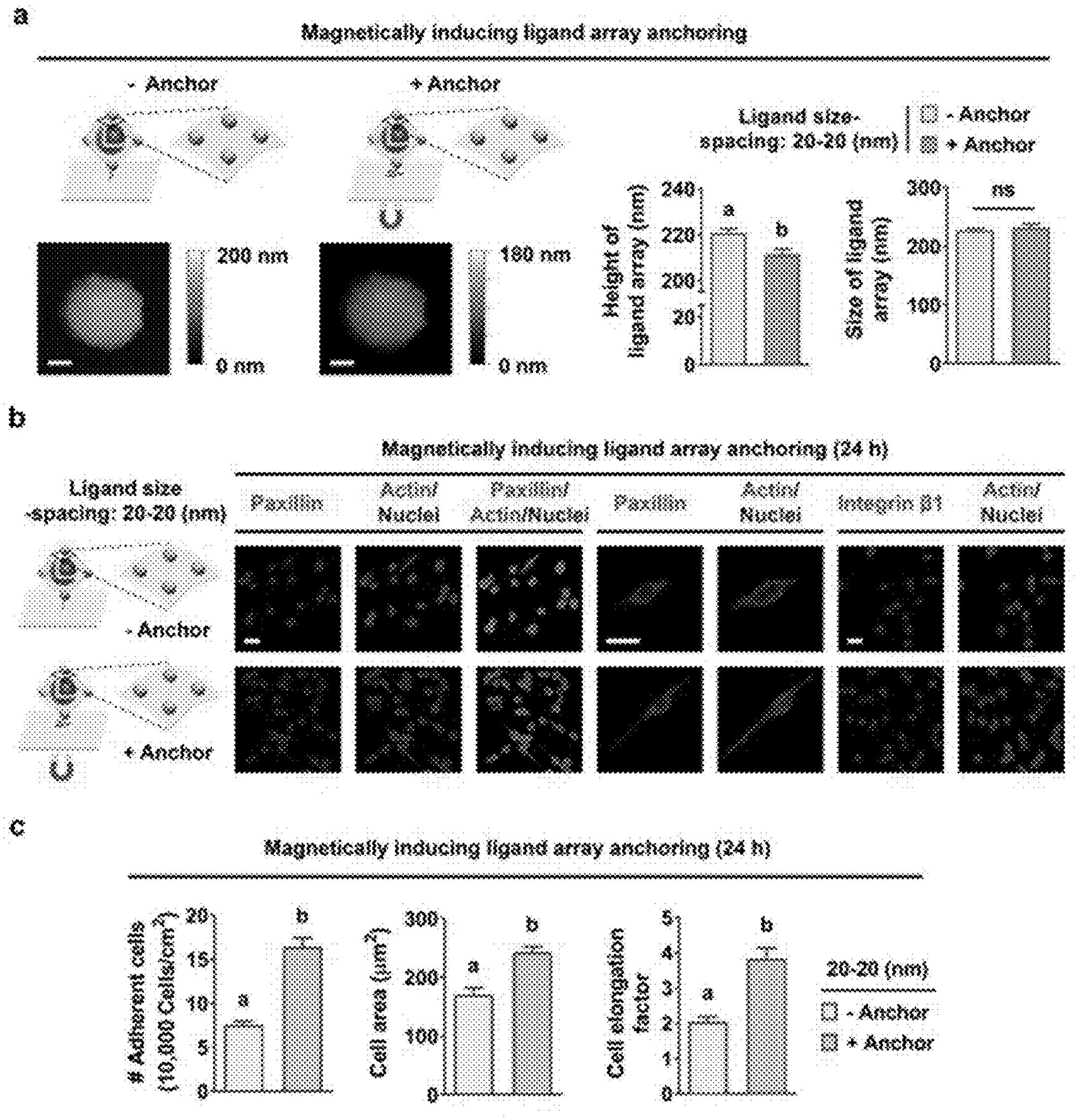
FIGS. 52 to 53 show the results of experiments conducted on macrophage adhesion and polarization using nanosatellite-substrate complexes, prepared by modulating the diameter of gold nanoparticles and the distance between adjacent gold nanoparticles, before and after applying a magnetic field to the nanosatellite-substrate complexes.

FIG. 52 shows the results of observing changes in the nanosatellite structure and the adhesion of macrophages before and after applying a magnetic field to the nanosatellite-substrate complex.

In the AFM images of FIG. 52*a*, the shading of the nanosatellite structure changed between before and after the application of the magnetic field, and the height difference of the nanosatellite structure was 220.7±3.2 nm. However, there was no change in the shape or size of the nanosatellite structure even when a magnetic field was applied.

The immunofluorescent staining images and quantification graphs in FIGS. 52*b* and 52*c* show widespread assemblies of integrin β1, F-actin, and paxillin adhesion complexes with significantly higher adherent cell numbers, spread area, and elongated morphology in the “+Anchor” group compared with the “−Anchor” group.

Figure 53:
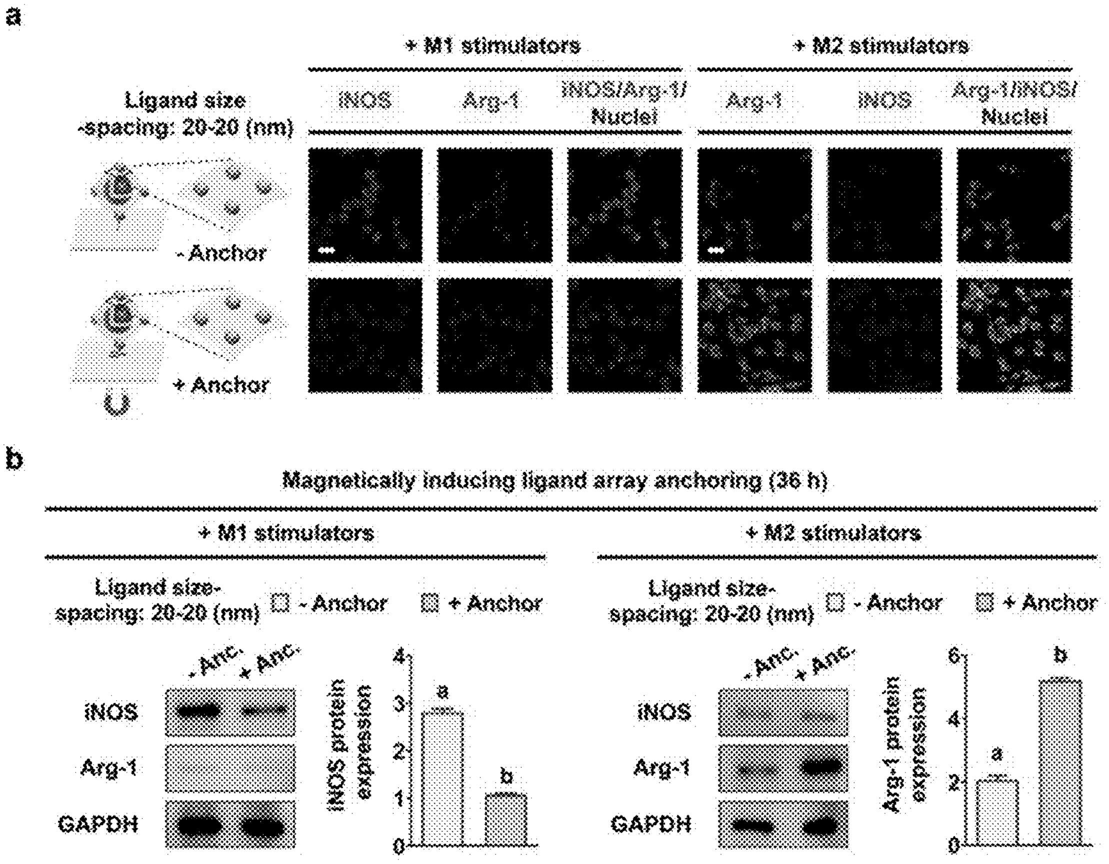

FIG. 53 shows the results of observing the occurrence of macrophage polarization before and after the application of a magnetic field. As can be seen in the immunofluorescent staining and western blotting images of FIG. 53, when macrophages were cultured in the medium with M2 stimulators, expression of the M2 polarization marker Arg-1 was promoted in the “+Anchor” group, but when macrophages were cultured in the medium with M1 stimulators, expression of the M1 polarization marker iNOS was promoted in the “−Anchor group”.

This experiment can mimic the 3-D dynamics of heterogeneously organized ligands in native FN and modulate integrin binding, stabilization, and clustering on the intramolecular and intermolecular scale. Thus, nanosatellite-substrate complexes prepared by modulating the diameter of gold nanoparticles and the distance between adjacent gold nanoparticles can offer limitless combinations of 3-D dynamic ligand arrays to systematically investigate complex nanogeometry-dependent integrin binding and clustering.

(5) Experiment on Macrophage Polarization Using Inhibitors

The signaling pathway involving ROCK, actin polymerization, and myosin II regulates the host responses, such as pro-healing vs. inflammatory phenotypic polarization of macrophages. The present inventors investigated how macrophage adhesion formation regulates the phenotypic polarization of macrophages by using inhibitors. As the inhibitors, inhibitors specific for ROCK (Y27632), actin polymerization (cytochalasin D), and myosin II (blebbistatin) were used.

Figure 54:
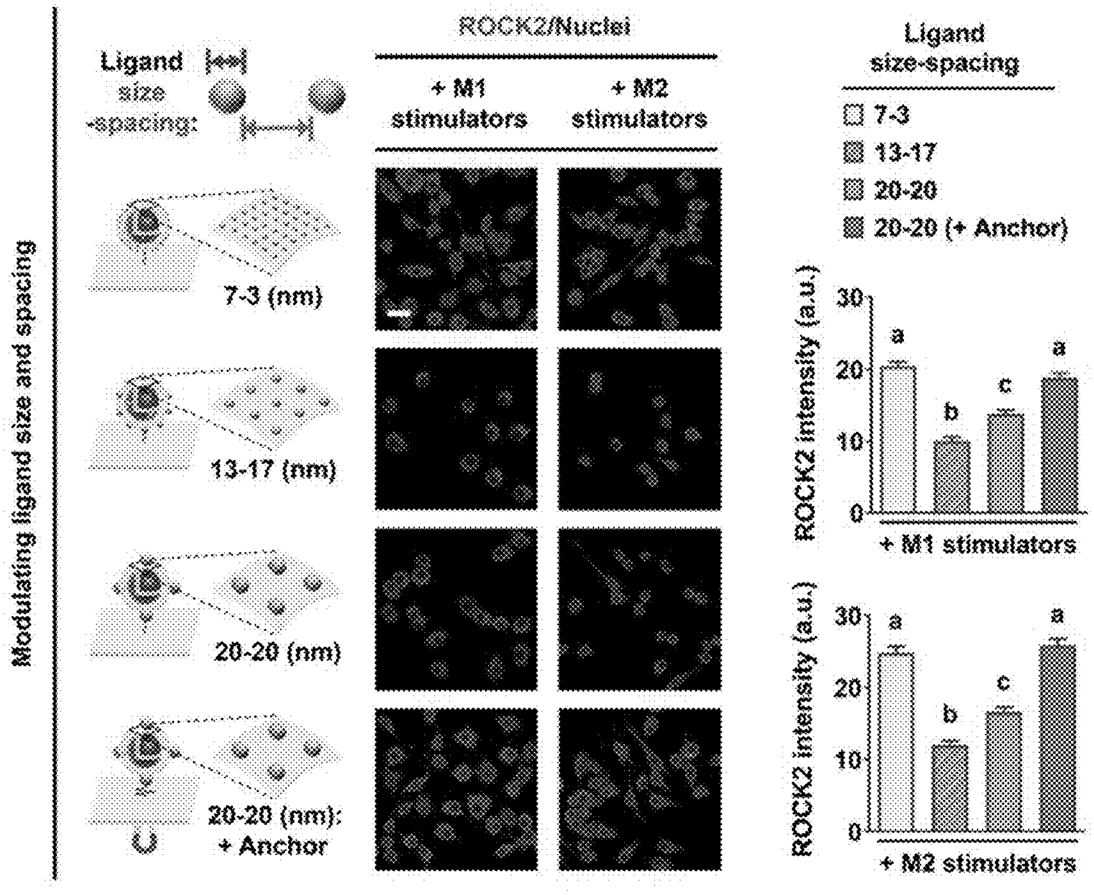
FIGS. 54 to 56 show the results of experiments conducted on macrophage polarization using nanosatellite-substrate complexes, prepared by modulating the diameter of gold nanoparticles and the distance between adjacent gold nanoparticles, in the presence of inhibitors.
Figure 55:
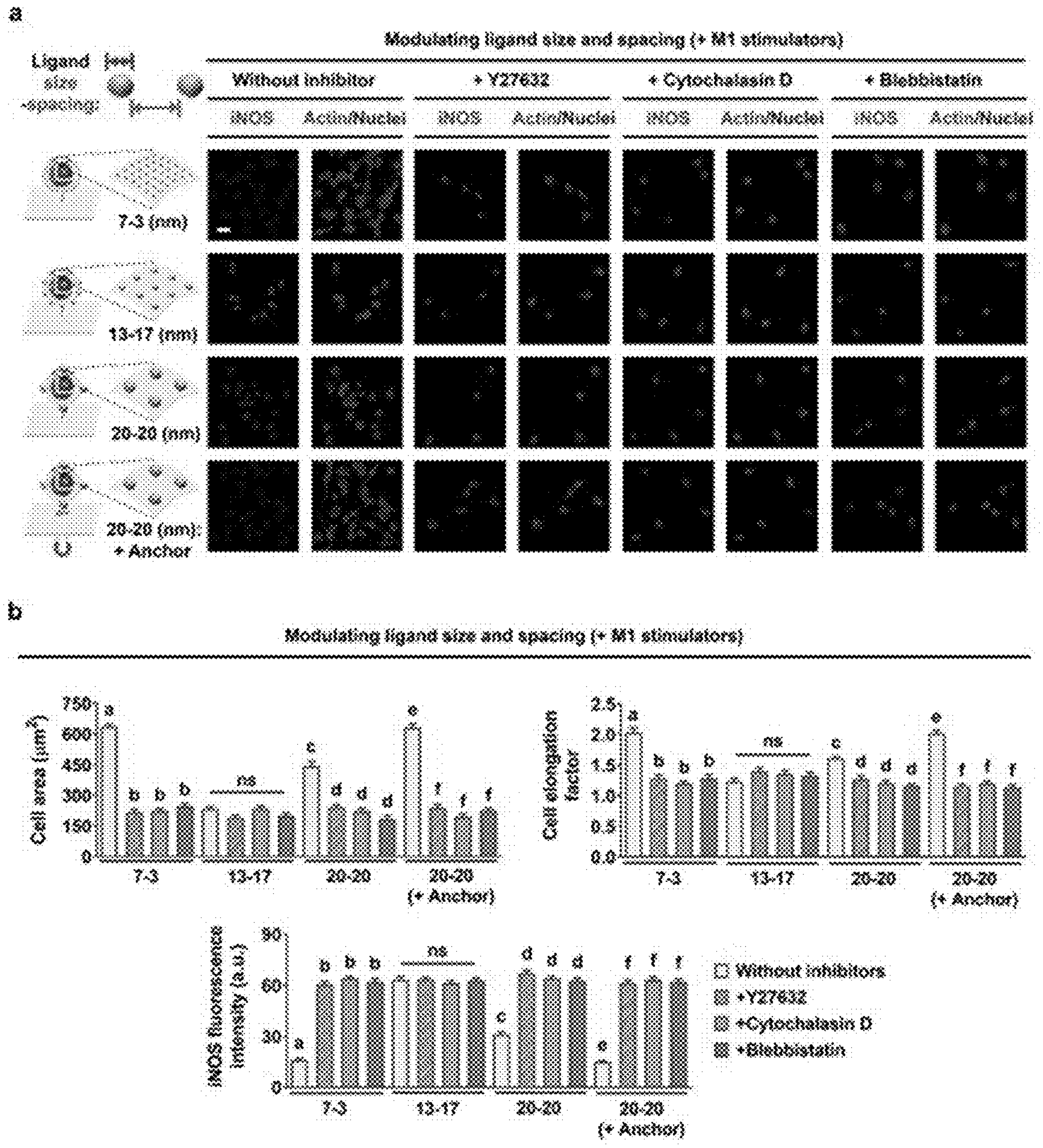
Figure 56:
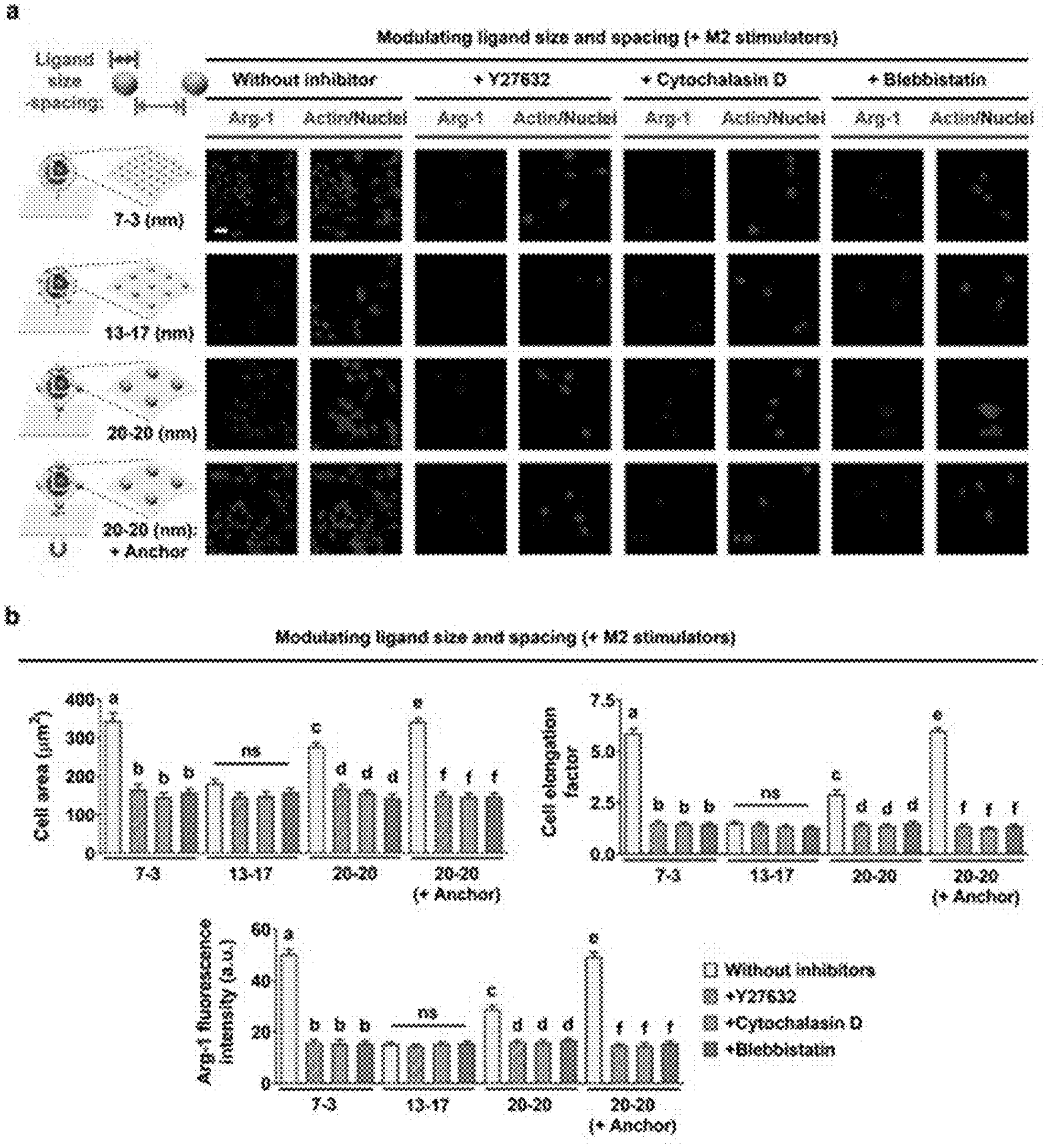

FIGS. 54 to 56 show immunofluorescence staining images and quantification graphs for the “7-3” group, “13-17” group, and “20-20” group (−Anchor and +Anchor).

When macrophages were cultured in the medium with M1 stimulators, adherent cell area and elongated morphology were more substantial in the “7-3” and “20-20 (+Anchor”) groups compared with the “13-17” and “20-20” (−Anchor) groups. Also, as can be seen in FIG. 55, the expression of iNOS was minimal in the “7-3” group and the “20-20” (+Anchor) group, but increased in the presence of the inhibitors.

Conversely, when macrophages were cultured in the medium with M2 stimulators, Arg-1 expression was higher in the “7-3” group and “20-20” (+Anchor) group, and decreased in the presence of the inhibitors (FIG. 56). These results collectively reveal that both pseudo-connecting and anchoring of the ligand arrays independently intensify macrophage adhesion involving molecular complexes of rho kinase (ROCK), actin filaments, and myosin II that augment M2 polarization and hinder M1 polarization.

Experimental Example 4

Regulation of Human Macrophages

The present inventors used human primary cells via flow cytometry through antibody-based magnetic separation of CD14+ monocytes from CD45+ human peripheral blood mononuclear cells (hPBMCs). The results are shown in FIGS. 57 and 58.

Figure 58:
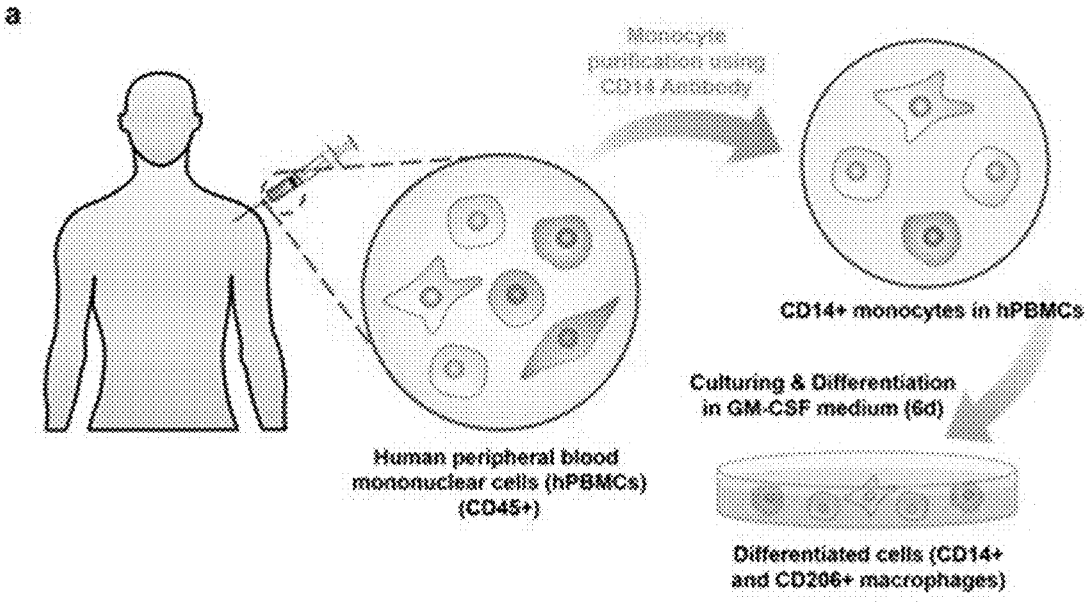
Figure 58:
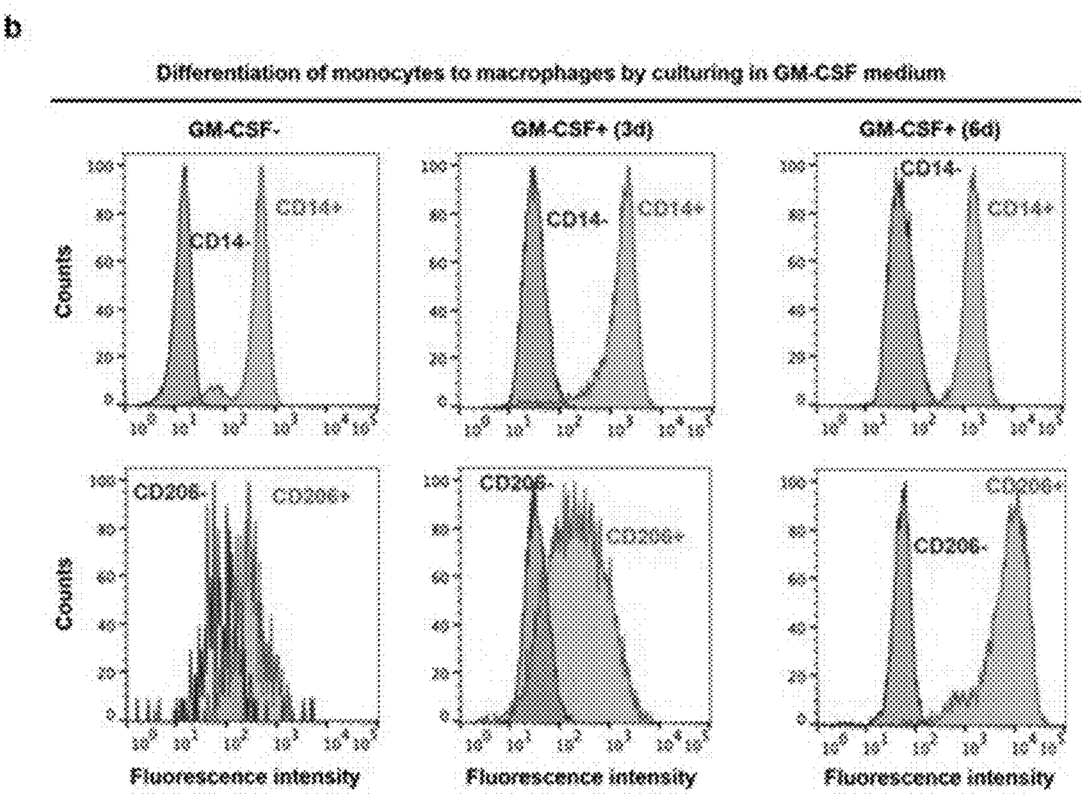

The present inventors further differentiated these CD14+ monocytes into macrophages in the growth media containing granulocyte macrophage-colony stimulating factor (GM-CSF) and characterized macrophages using specific fluorescent probe-attached antibodies via flow cytometry (FIG. 58).

Figure 57:
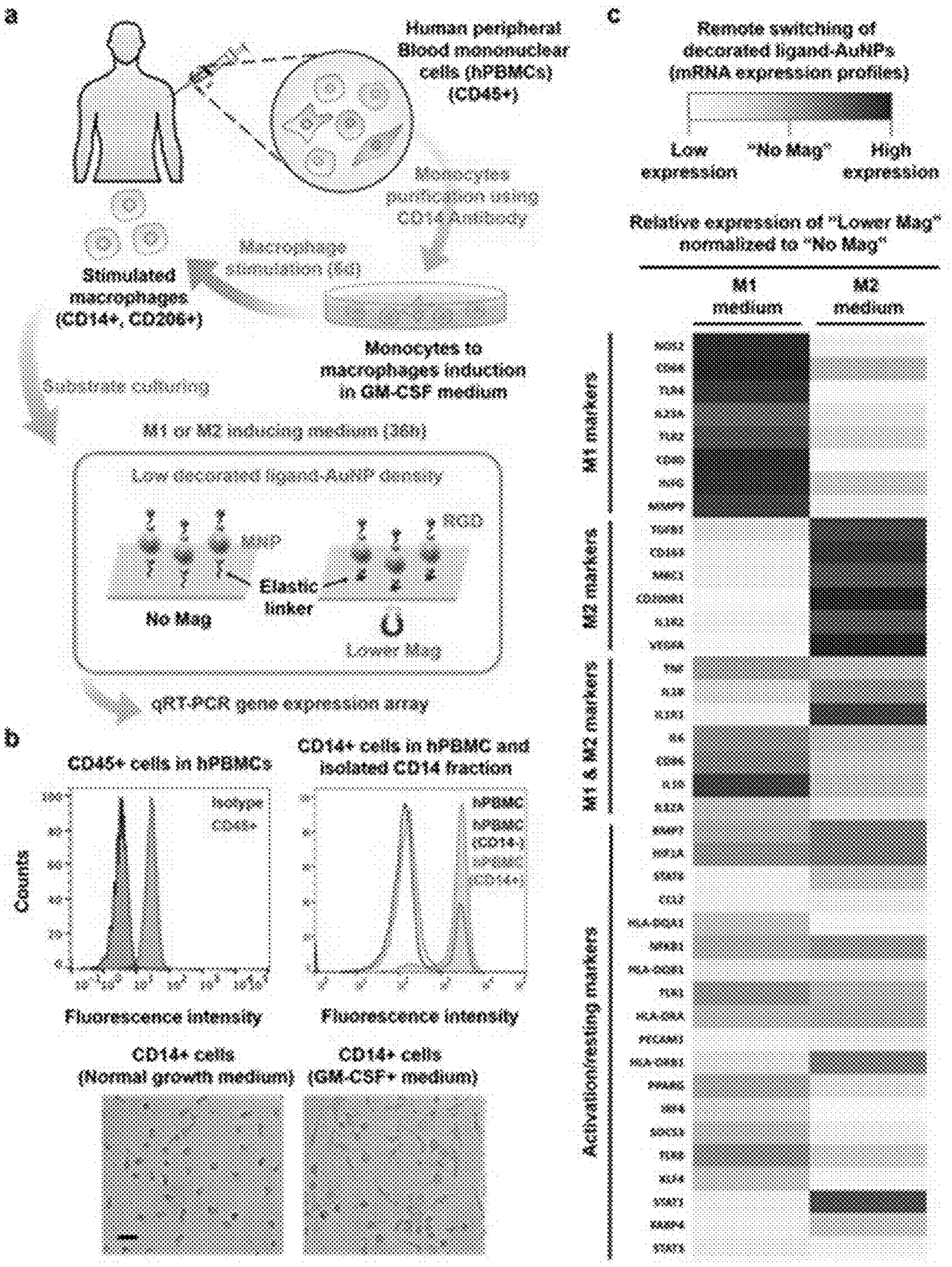
FIGS. 57 and 58 show the results of experiments conducted on human macrophages using nanosatellite-substrate complexes prepared by modulating only the density of gold nanoparticles.

The present inventors found that the "Lower Mag" condition significant inhibits M1 polarization markers and promotes M2 polarization markers compared to the "No Mag" condition via qRT-PCR-based mRNA expression profiling of human macrophages, similar to our previous findings using mouse macrophages (FIG. 57).

Experimental Example 5

The regulation of macrophage adhesion and M2 polarization mediates tissue healing while suppressing inflammation. Therefore, an experiment was conducted to examine whether each nanosatellite-substrate complex implanted in vivo could regulate the adhesion and polarization of host macrophages, similar to the case of the in vitro experiment.

1. Modulation of Only Density of Gold Nanoparticles

The nanosatellite-substrate complex and M2-polarizing stimulators (interleukin (IL)-4 and IL-13) were injected into the subcutaneous pockets of mice. The permanent magnet was attached to the skin on the backs of the mice ("Upper Mag") or to the skin on the abdomens of the mice ("Lower Mag"), and after 24 hours, protein expression was monitored.

Figure 59:
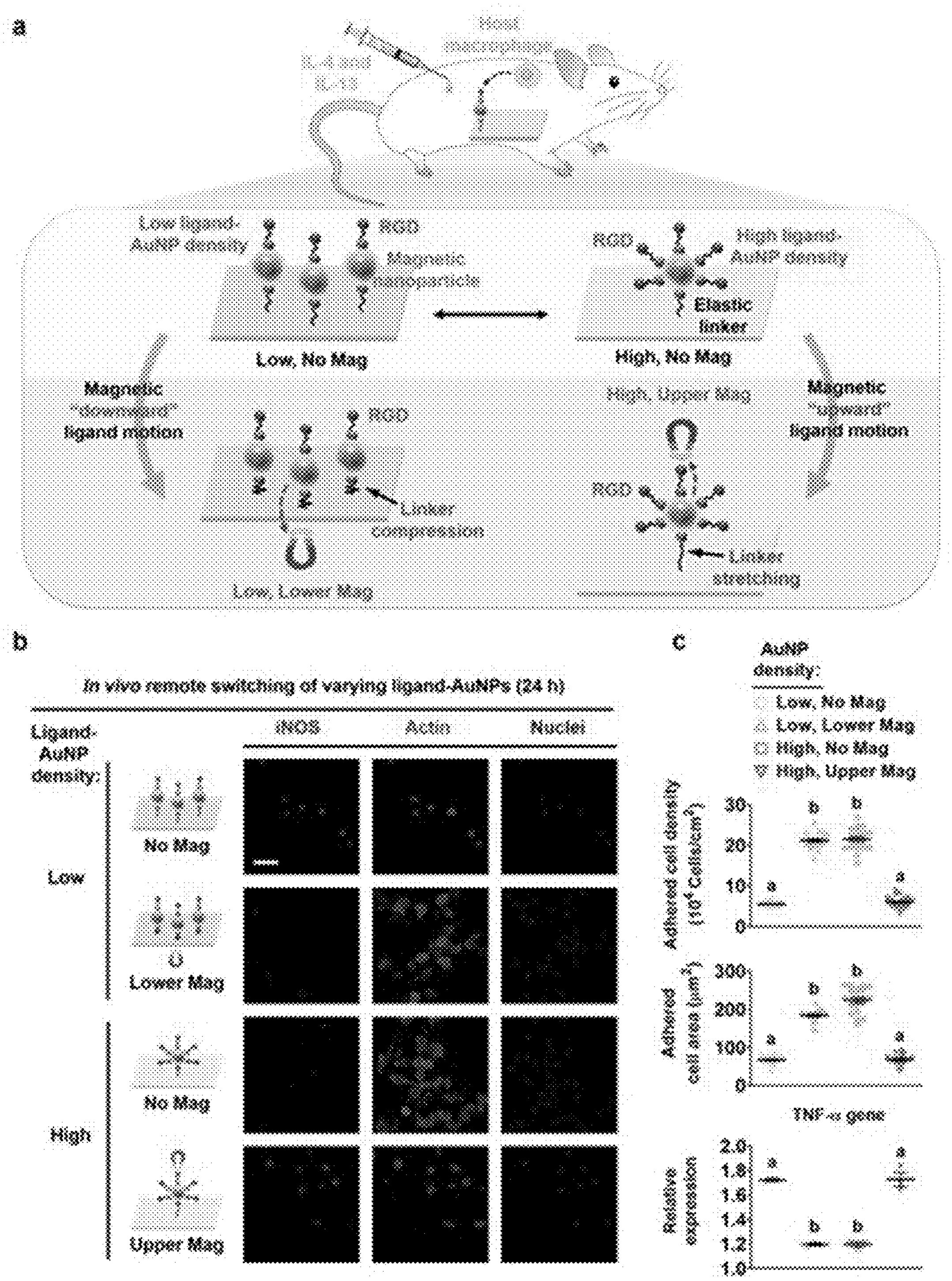
FIGS. 59 to 63 show the results of experiments conducted by in vivo implantation of nanosatellite-substrate complexes prepared by modulating only the density of gold nanoparticles.
Figure 60:
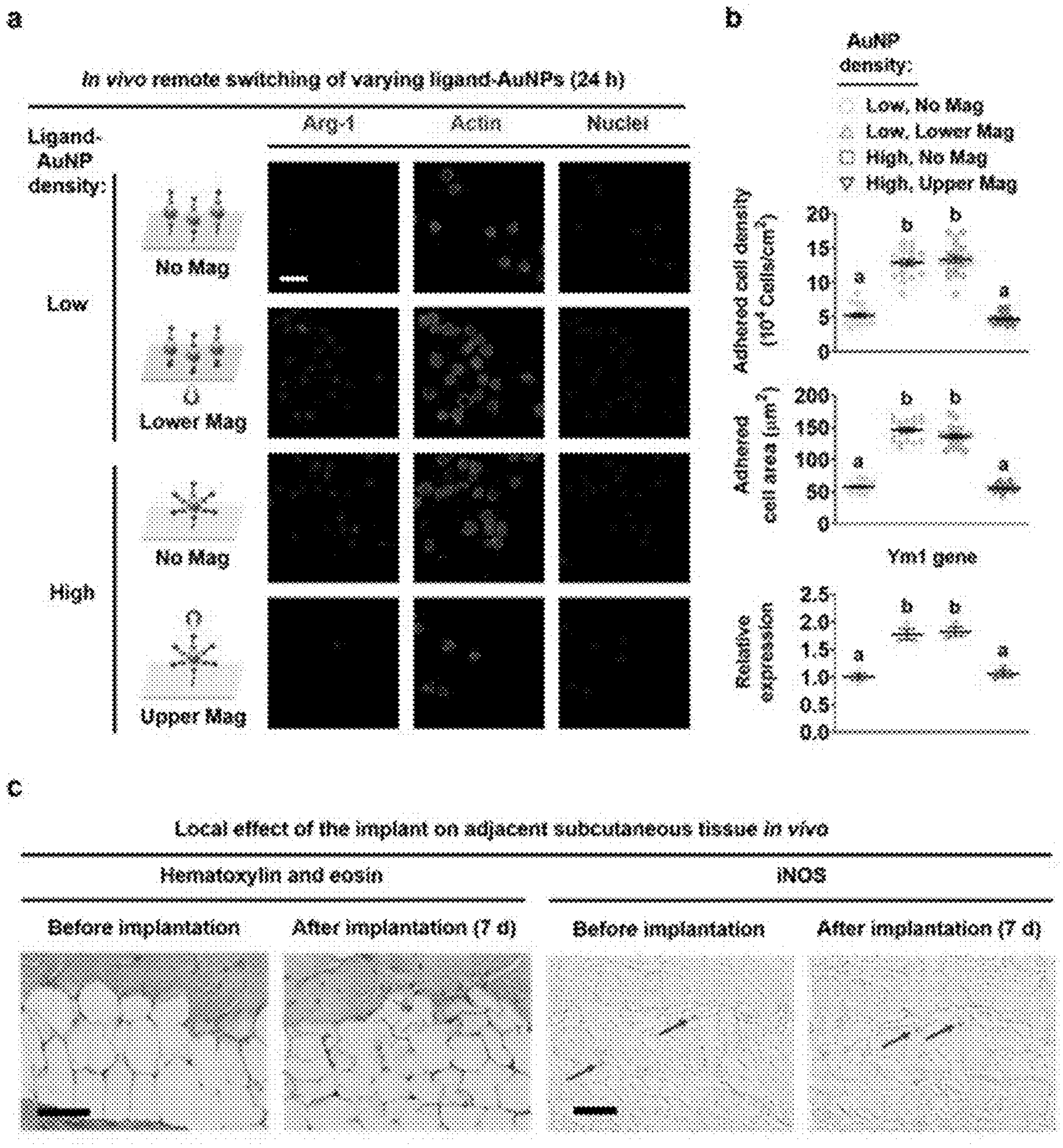
Figure 61:
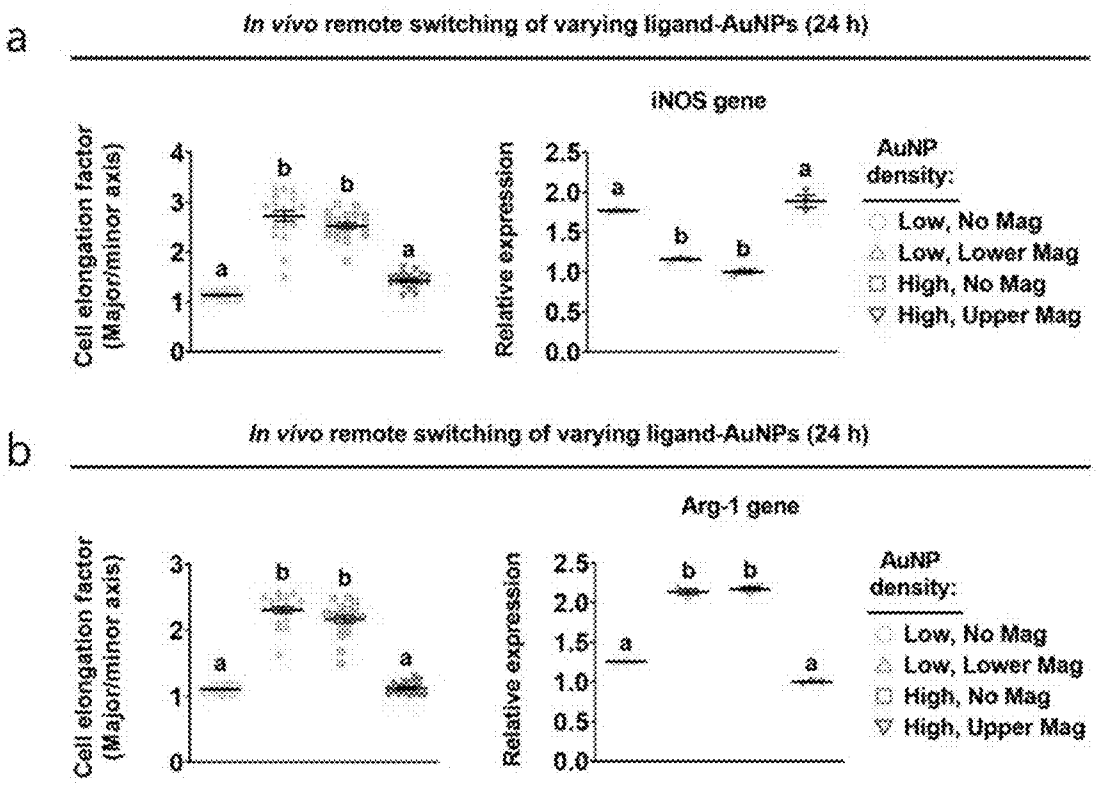

As can be seen in FIGS. 59 to 61, magnetic downward movement ("Lower Mag") of the nanosatellite structure at low gold nanoparticle density substantially promoted the adhesion of macrophages that suppresses M1 polarization (lower TNF-α and iNOS expression) but promotes M2 polarization (higher Ym-1 and Arg-1 expression) compared with the "No Mag" condition. In addition, confocal immunofluorescence images with gene expression profiles demonstrated that upward movement ("Upper Mag") of the nanosatellite structure at high gold nanoparticle density considerably inhibited the adhesion of macrophages that facilitates M1 polarization (higher TNF-α and iNOS expression) but inhibits M2 polarization (higher Ym-1 and Arg-1 expression) compared with the "No Mag" condition.

Figure 62:
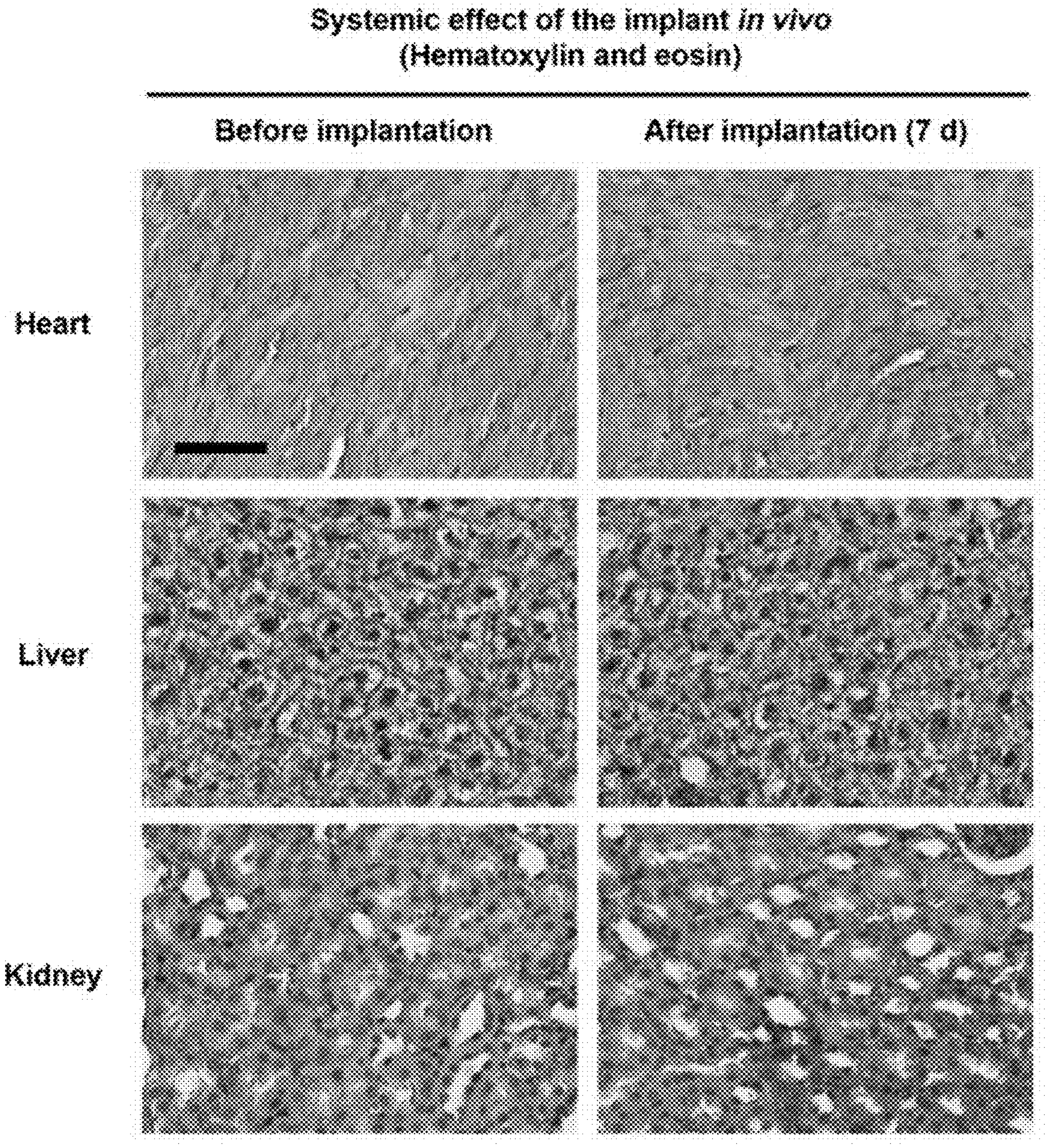
Figure 63:
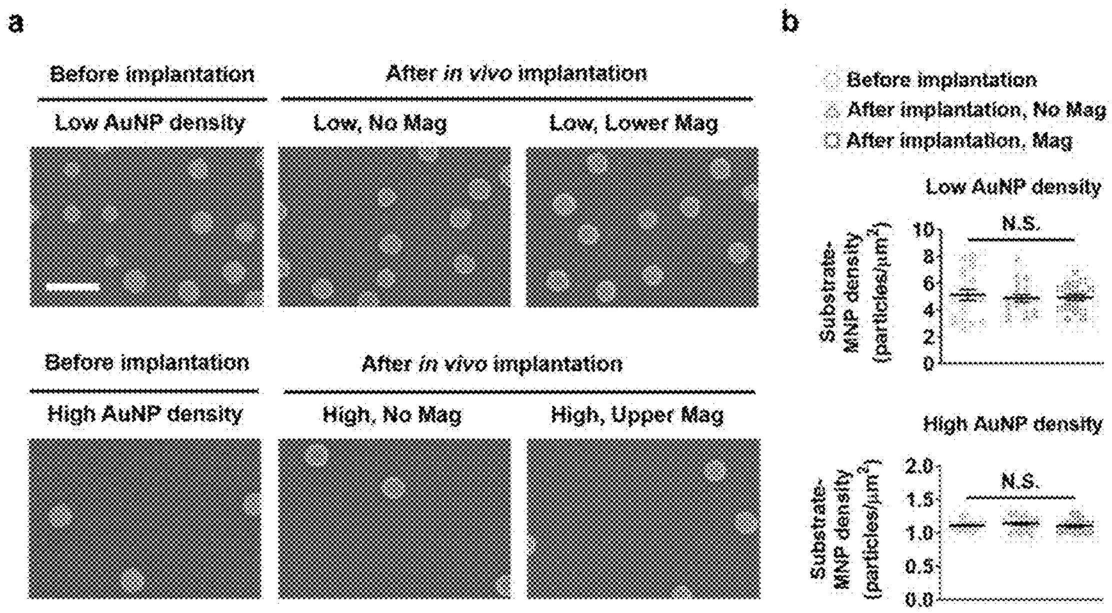

In addition, FIGS. 61 to 63 confirmed that the nanosatellite-substrate complex of the present invention exhibited no toxicity to the living body.

H&E staining and immunohistochemical staining for iNOS of surrounding subcutaneous and other tissues confirmed that the nanosatellite-substrate complex induced minimal toxicity and inflammatory response (FIGS. 60 and 62). This observation was made before and 7 days after implantation, and no difference was found between the tissues before and after transplantation.

In addition, as shown in FIG. 63, the shape of the nanosatellite-substrate complex before and after implantation was examined, and no change in the shape or density of the nanosatellite structure was observed even when no magnetic field was applied or when a magnetic field was applied after implantation.

Therefore, it was confirmed that the nanosatellite-substrate complex of the present invention is safe even when it is implanted into the human body.

2. Modulation of Diameter of Gold Nanoparticles and Distance Between Gold Nanoparticles Nanosatellite-substrate complexes prepared by modulating the diameter of gold nanoparticles and the distance between adjacent gold nanoparticles were implanted into the subcutaneous pockets of mice, and then an experiment on macrophage polarization was conducted. For subcutaneous implantation, the "7-3", "13-17" and "20-20" groups were used, and M2 stimulators were injected onto the surface of the substrate. In addition, in the "20-20" group, a permanent magnet was attached to the abdomen of the mouse, and two conditions were created by applying (+Anchor) or not applying (−Anchor) a magnetic field.

Figure 64:
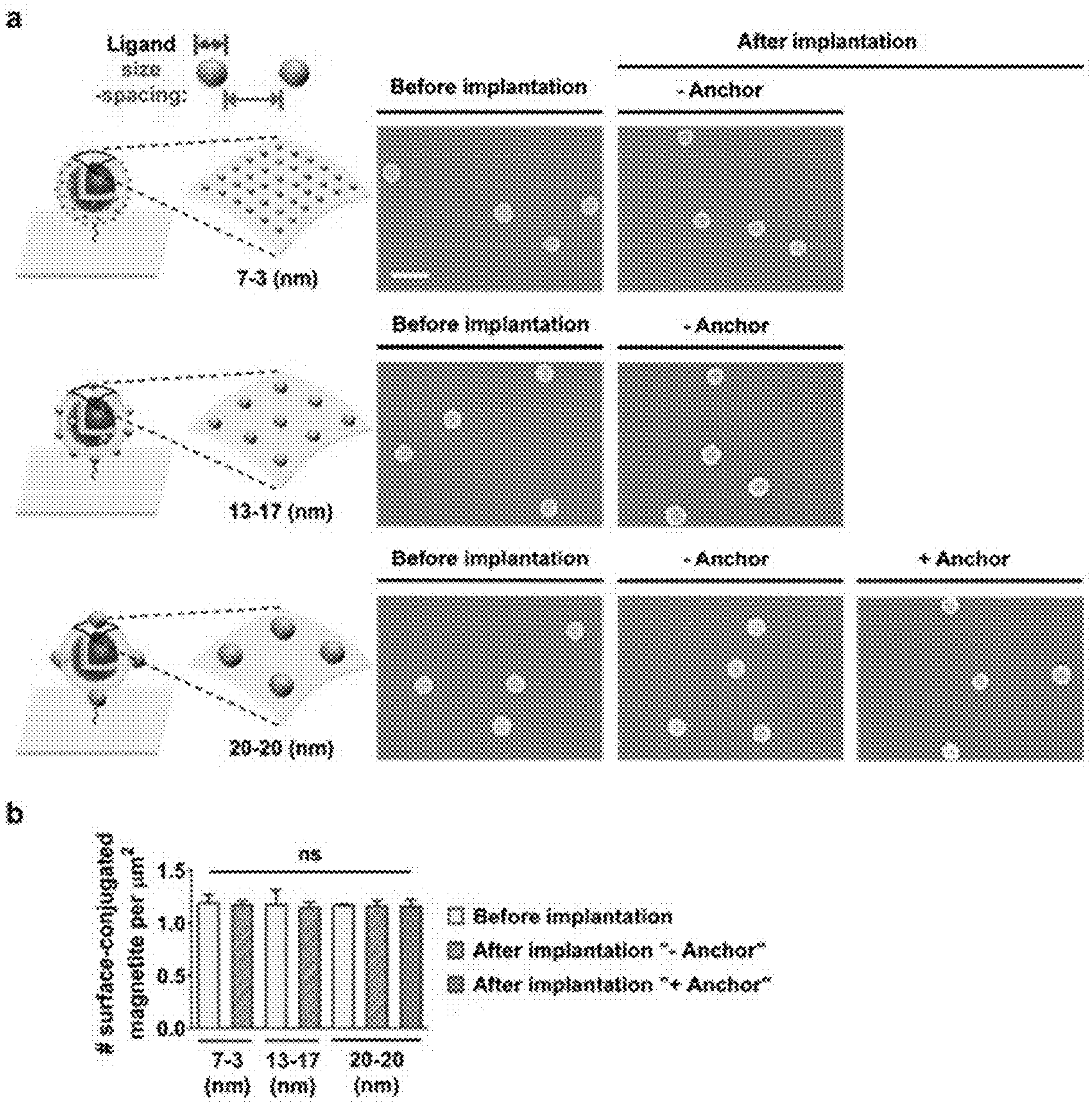
FIGS. 64 to 67 show the results of experiments conducted by in vivo implantation of nanosatellite-substrate complexes prepared by modulating the density of gold nanoparticles and the distance between adjacent gold nanoparticles.

FIG. 64 shows the results of observing the shape of the nanosatellite-substrate complex before and after implantation into the mice. It can be observed that there was no difference in the shape or density of the nanosatellite structure on the substrate between before and after implantation and regardless of whether the magnetic field was applied, indicating that that the nanosatellite-substrate complex is non-toxic and stable in vi vo.

Figure 65:
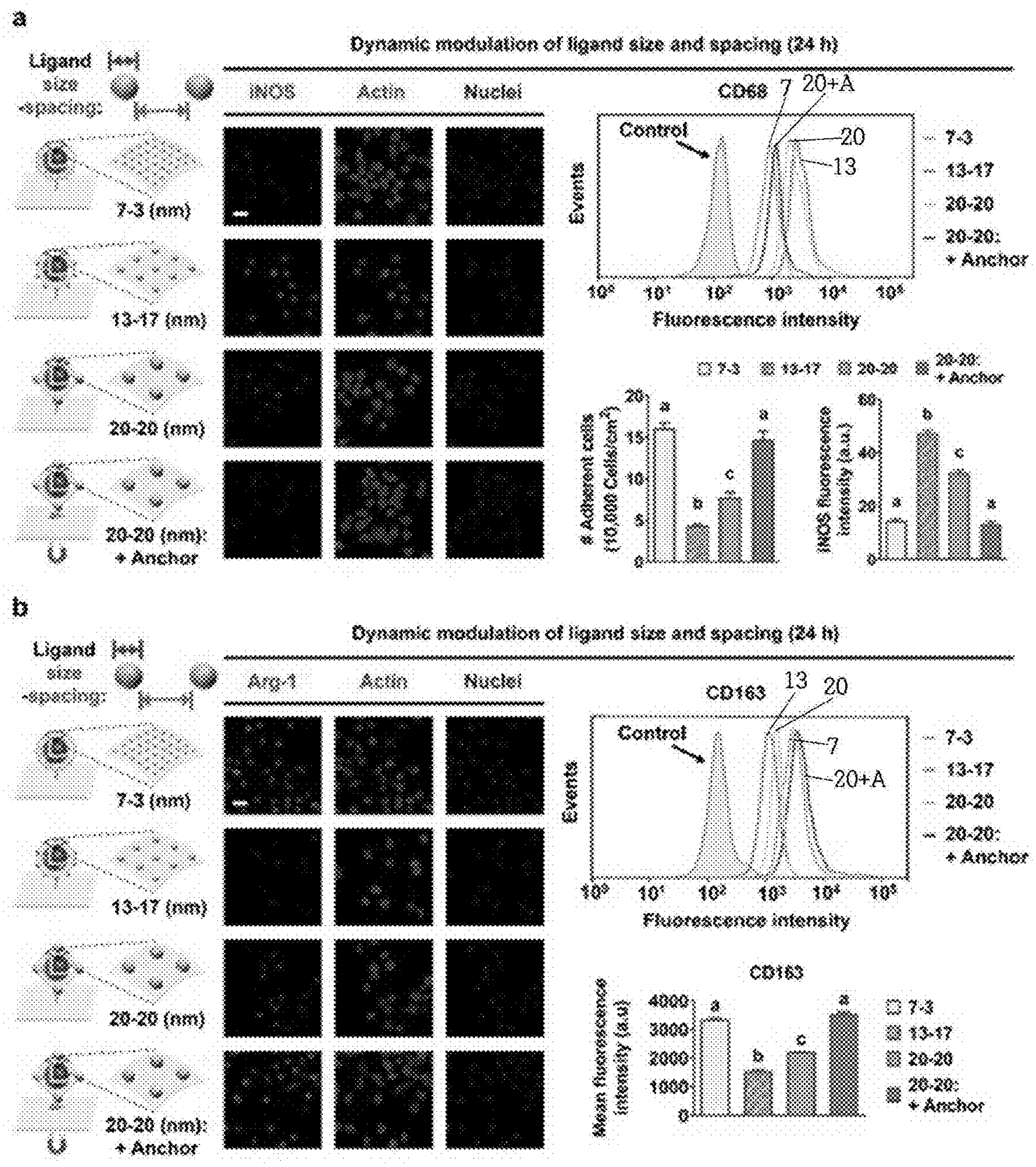
Figure 66:
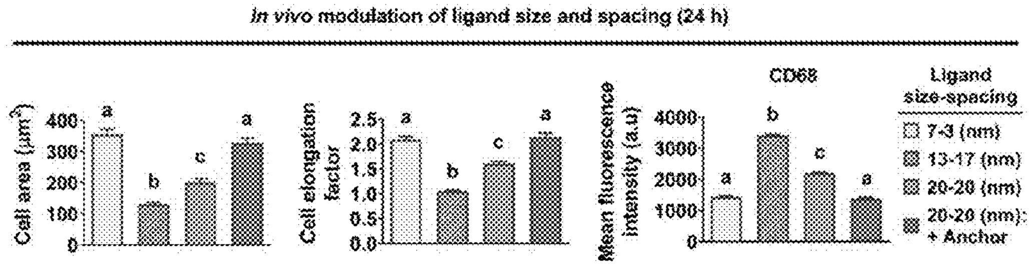

FIGS. 65 and 66 show the results of co-staining M1 marker (iNOS) and M2 marker (Arg-1) along with F-actin and nuclei to identify the host macrophages. It was shown that the adherent host cell number, spread area, and aspect-ratio shape in the "7-3" group and the "20-20" group (+Anchor) were higher than those in the other groups, but the expression level of iNOS was low.

In addition, flow cytometry histograms concordantly confirmed that inflammatory marker (CD68) was substantially more highly expressed in the "13-17" and "20-20" groups whereas anti-inflammatory marker (CD163) was considerably more highly expressed in the "7-3" and "20-20 (+Anchor)" groups.

Figure 67:
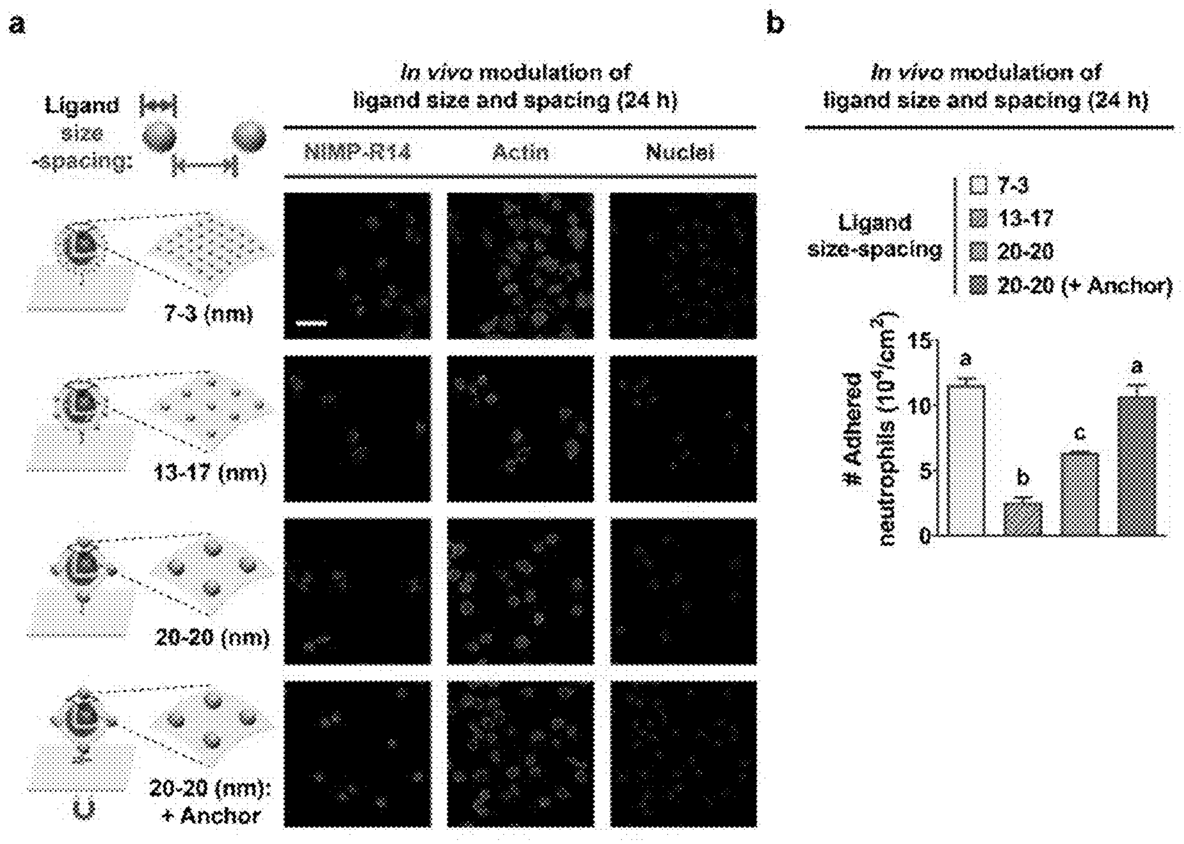

The present inventors additionally found host cells positive for NIMP-R14, thus indicating that host neutrophils were also recruited to the ligands by early host response (FIG. 67).

These results collectively substantiate that the pseudo-connected ligands efficiently stimulate macrophage adhesion formation to augment M2 polarization but restrain M1 polarization of macrophages. Strikingly, while the adhesion formation of macrophages was not extensively observed in the "20-20" group, magnetically induced ligand anchoring in the "20-20, +Anchor" group elevated the level of macrophage adhesion comparable to that of the pseudo-connected ligand. This suggests that recruited host cells perceived the anchored ligands as pseudo-connected, and thus stabilized integrin clustering and bridged the disconnected ligands in response.

From these results, it can be confirmed that the adhesion and polarization of macrophages can be stably regulated even in vivo by applying a magnetic field to the nanosatellite-substrate complex of the present invention.

As described above, according to the present invention, it is possible to provide a nanosatellite-substrate complex capable of regulating macrophage adhesion and polarization.

In addition, according to the present invention, it is possible to provide a method for preparing a nanosatellite-substrate complex capable of regulating macrophage adhesion and polarization.

In addition, according to the present invention, it is possible to provide a method of regulating macrophage adhesion and polarization using the nanosatellite-substrate complex.

While the present invention has been described with reference to the particular illustrative embodiments, it will be understood by those skilled in the art to which the present invention pertains that the present invention may be embodied in other specific forms without departing from the technical spirit or essential characteristics of the present invention. Therefore, the embodiments described above are considered to be illustrative in all respects and not restrictive. Furthermore, the scope of the present invention is defined by the appended claims rather than the detailed description, and it should be understood that all modifications or variations derived from the meanings and scope of the present invention and equivalents thereto are included in the scope of the present invention.

What is claimed is:

1. A nanosatellite-substrate complex for regulating macrophage adhesion and polarization comprising:
a substrate;
a core-shell-type magnetic nanoparticle disposed to be spaced apart from a first side of the substrate;
a plurality of gold nanoparticles connected to one side of the magnetic nanoparticle;
a plurality of first linkers connecting between the substrate and the plurality of gold nanoparticles;
a plurality of second linkers connecting between the plurality of gold nanoparticles and a plurality of ligands; and
the plurality of ligands connected to the plurality of gold nanoparticles via the plurality of second linkers,
wherein the plurality of gold nanoparticles is are connected to the plurality of ligands via the plurality of second linkers to form a nanoassembly,
the magnetic nanoparticle is conjugated to the nanoassembly to form a nanosatellite structure,
the nanoassembly comprises the plurality of gold nanoparticles, the plurality of second linkers connected to the plurality of gold nanoparticles, and the plurality of ligands connected to the plurality of second linkers, and
a plurality of nanoassemblies are comprised in the nanosatellite structure, and
wherein the plurality of the nanoassemblies are disposed adjacent to each other, and a distance between the plurality of gold nanoparticles in the plurality of nanoassemblies disposed adjacent to each other includes at least one of a first distance, a second distance and a third distance,
wherein the first distance is 2 nm to 4 nm, the second distance is 15 nm to 20 nm, and the third distance is 18 nm to 22 nm.

2. The nanosatellite-substrate complex of claim 1, wherein the magnetic nanoparticle is composed of:
a core composed of iron oxide; and
a shell disposed to cover the outer surface of the core and comprising silica.

3. The nanosatellite-substrate complex of claim 1, wherein the plurality of gold nanoparticles have at least one diameter selected from among a first average diameter, a second average diameter, and a third average diameter,
wherein the first average diameter is 3.5 nm to 10.5 nm, the second average diameter is 12 nm to 14 nm, and the third average diameter is 15 nm to 25 nm.

4. The nanosatellite-substrate complex of claim 1, wherein the plurality of nanoassemblies are disposed to completely cover the outer surface of the magnetic nanoparticle.

5. The nanosatellite-substrate complex of claim 1, wherein the magnetic particle has an average diameter of 150 nm to 250 nm, and comprises at least one of an amino group (—$HN_2$) and a thiol group (—SH) on a surface thereof.

6. The nanosatellite-substrate complex of claim 1, wherein the plurality of first linkers and the plurality of second linkers have a structure of the following Formula 1:

[Formula 1]

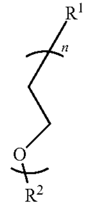

wherein $R^1$ is one of a thiol group (—SH) and an amine group (—$NH_2$), $R^2$ is one of a carboxyl group (—COOH), an amine group (—$NH_2$) and a succinimidyl ester group, and n is a number ranging from 113 to 450.

7. The nanosatellite-substrate complex of claim 1, wherein the plurality of ligands are cyclic RGD ligands.

8. The nanosatellite-substrate complex of claim 1, wherein a surface of the nanosatellite structure, which faces the substrate, is spaced apart from the substrate with the plurality of first linkers interposed therebetween, and the plurality of first linkers are elastic and a length thereof is reversibly changed by application of a magnetic field.

9. The nanosatellite-substrate complex of claim 1, wherein
the nanosatellite structure is disposed to be spaced apart from the first of the substrate,
the plurality of first linkers are compressed by applying a magnetic field to a second side of the substrate, opposite to the first side of the substrate, and
the nanosatellite structure moves in a direction toward the substrate to promote macrophage adhesion and M2 polarization.

10. The nanosatellite-substrate complex of claim 1, wherein
the nanosatellite structure is disposed to be spaced apart from one the first side of the substrate,
the plurality of first linkers are stretched by applying a magnetic field to an upper side of the nanosatellite structure, which is the first side of the substrate, and
the nanosatellite structure moves in a direction away from the substrate to inhibit macrophage adhesion and promote macrophage M1 polarization.

11. The nanosatellite-substrate complex of claim 1, wherein a density of the nanosatellite structure disposed on the substrate is 1.0 nanosatellite structure/$\mu m^2$ to 6 nanosatellite structures/$\mu m^2$.

12. A method for preparing the nanosatellite-substrate complex for regulating macrophage adhesion and polarization of claim 1, the method comprising:
coating a surface of iron oxide with a silica having at least one of an amino group and a thiol group to form magnetic particles;
providing gold nanoparticles on surfaces of the magnetic particles;
adding and dispersing the magnetic particles having the gold nanoparticles provided thereon in a solution containing a polymer linker to form a first linker and a second linker;
reacting the first linker with a substrate having amine groups formed thereon, so that the first linker is bound to at least a portion of the amine groups formed on the substrate and the magnetic particles having the gold nanoparticles provided thereon are conjugated to the substrate;

deactivating amine groups, which remain unbound to the first linker on the substrate, by treatment with a deactivating group; and conjugating a ligand to the second linker.

13. The method of claim 12, wherein the gold nanoparticles have any one diameter selected from among a first average diameter, a second average diameter and a third average diameter;

the first average diameter of the gold nanoparticles is 3.5 nm to 10.5 nm, and the gold nanoparticles having the first average diameter are formed by reacting first gold seed particles with amine groups on the surfaces of the magnetic particles to provide the gold seed particles on the magnetic particles, and adding and stirring the magnetic particles having the gold seed particles provided thereon in a gold-containing solution to grow the gold seed particles; or the second average diameter of the gold nanoparticles is 12 nm to 14 nm and the third average diameter thereof is 15 nm to 25 nm, and the gold nanoparticles having the second or third average diameter are provided on the magnetic particles by adding and stirring second gold seed particles in a gold-containing solution to grow the second gold seed particles, thereby forming gold nanoparticles, and reacting the gold nanoparticles, formed by growing the second gold seed particles, with amine groups on the surfaces of the magnetic particles.

14. The method of claim 13, wherein the gold-containing solution comprises a first solution containing sodium citrate and a second solution containing chloroauric acid, the first solution and the second solution are sequentially added, and the average diameter of the gold nanoparticles is controlled by controlling the number of times the first solution and the second solution are added.

15. A method of regulating macrophage adhesion and polarization using a nanosatellite-substrate complex, the method comprising regulating macrophage adhesion and polarization by applying a magnetic field to the nanosatellite-substrate complex according to claim 1.

16. The method of claim 15, wherein the magnetic field is applied from outside the body to remotely control the nanosatellite-substrate complex in the body.

17. The method of claim 15, wherein the magnetic field has a strength of 100 mT to 500 mT.

18. The method of claim 15, wherein the nanosatellite structure is provided to be spaced apart from one side of the substrate, a plurality of the nanoassemblies are provided adjacent to each other in the nanosatellite structure, the gold nanoparticles have an average diameter of 3.5 nm to 10.5 nm, a distance between the gold nanoparticles in the nanoassemblies provided adjacent to each other is 2 nm to 4 nm, the first linker is stretched by applying a magnetic field to an upper side of the nanosatellite structure, which is one side of the substrate, and the nanosatellite structure moves in a direction away from the substrate to inhibit macrophage adhesion and promote macrophage M1 polarization.

19. The method of claim 15, wherein the nanosatellite structure is provided to be spaced apart from one side of the substrate, a plurality of the nanoassemblies are provided adjacent to each other in the nanosatellite structure, the gold nanoparticles have an average diameter of 12 nm to 14 nm, a distance between the gold nanoparticles in the nanoassemblies provided adjacent to each other is 15 nm to 20 nm, the first linker is compressed by applying a magnetic field to the other side of the substrate, and the nanosatellite structure moves in a direction toward the substrate to promote macrophage adhesion and M2 polarization.

* * * * *